United States Patent
Cimica

(10) Patent No.: US 11,179,460 B2
(45) Date of Patent:

(56) References Cited

OTHER PUBLICATIONS

Dai, Lianpan et al., "Structures of the Zika Virus Envelope Protein and Its Complex with a Flavivirus Broadly Protective Antibody," Cell Host & Microbe, vol. 19, No. 5, May 11, 2016, pp. 696-704.
Billaud, Jean-Noel et al., "Combinatorial Approach to Hepadnavirus-Like Particle Vaccine Design," Journal of Virology, vol. 79, No. 21, Nov. 2005, pp. 13656-13666.
Brown, W. Clay et al., "Extended Surface for Membrane Association in Zika Virus NS1 Structure," Nature Structural & Molecular Biology, vol. 23, No. 9, Sep. 2016, pp. 865-867.
Sirohi, Devika et al., "The 3.8 Å resolution cryo-EM structure of Zika virus," Science, vol. 352, No. 6284, Apr. 22, 2016, p. 467-470.
Shang, Zifang et al., "Crystal Structure of the Capsid Protein from Zika Virus," Journal of Molecular Biology, vol. 430, No. 7, Mar. 30, 2018, pp. 948-962.
Zlatev, Ivan et al., "Solid-Phase Chemical Synthesis of 5'-Triphosphate DNA, RNA, and Chemically Modified Oligonucleotides," Current Protocols in Nucleic Acid Chemistry, Chapter 1, Unit 1.28, Sep. 2012. doi: 10.1002/0471142700.nc0128s50. PMID: 22956453.
Shivalingam, Arun et al., "Synthesis of chemically modified DNA," Biochemical Society Transactions, vol. 44, No. 3, Jun. 15, 2016, pp. 709-715. doi: 10.1042/BST20160051.
Richner, Justin M. et al., "Modified mRNA vaccines protect against Zika virus infection," Cell, vol. 168, No. 6, Mar. 9, 2017, pp. 1114-1125.
Betancourt, Dillon et al., "Cutting Edge: Innate Immune Augmenting Vesicular Stomatitis Virus Expressing Zika Mirus Proteins Confers Protective Immunity," Journal of Immunology, vol. 198, No. 8, Apr. 15, 2017, pp. 3023-3028.
Falugi, Fabiana et al., "Rationally designed strings of promiscuous CD4+ T cell epitopes provide help to Haemophilus influenzae type b oligosaccharide: a model for new conjugate vaccines," European Journal of Immunology, vol. 31, No. 12, Dec. 2001, pp. 3816-3824.
Diethelm-Okita, Brenda M. et al., "Universal Epitopes for Human CD4+ Cells on Tetanus and Diphtheria Toxins," The Journal of Infectious Diseases, vol. 181, No. 3, Mar. 2000, pp. 1001-1009.
Alexander, Jeff et al., "Linear Padre T Helper Epitope and Carbohydrate B Cell Epitope Conjugates Induce Specific High Titer IgG Antibody Responses," Journal of Immunology, vol. 164, No. 3, Feb. 1, 2000, pp. 1625-1633.
Dakappagari, Naveen K. et al., "A Chimeric Multi-Human Epidermal Growth Factor Receptor-2 B Cell Epitope Peptide Vaccine Mediates Superior Antitumor Responses," Journal of Immunology, vol. 170, No. 8, Apr. 15, 2003, pp. 4242-4253.
Pierson, Theodore C. et al., "Zika virus: immunity and vaccine development," Cell, vol. 167, No. 3, Oct. 20, 2016, pp. 625-631.
Kostyuchenko, Victor A. et al., "Structure of the thermally stable Zika virus," Nature, vol. 533, No. 7603, May 19, 2016, pp. 425-428.
Zhao, Haiyan et al., "Structural basis of Zika virus specific antibody protection," Cell, vol. 166, No. 4, Aug. 11, 2016, pp. 1016-1027.
Fibriansah, Guntur et al., "The development of therapeutic antibodies against dengue virus," Antiviral Research, vol. 128, Apr. 2016, pp. 7-19.
Priyamvada, Lalita et al., "Human antibody responses after dengue virus infection are highly cross-reactive to Zika virus," PNAS USA, vol. 113, No. 28, Jul. 12, 2016, pp. 7852-7857.
Dejnirattisai, Wanwisa et al., "Dengue virus sero-cross-reactivity drives antibody-dependent enhancement of infection with zika virus," Nature Immunology, vol. 17, No. 9, Sep. 2016, pp. 1102-1108.
Tan, Ming et al., "Subviral particle as vaccine and vaccine platform," Current Opinion in Virology, vol. 6, Jun. 2014, pp. 24-33.
Roose, Kenny et al., "Hepatitis B core-based virus-like particles to present heterologous epitopes," Expert Review of Vaccines, vol. 12, No. 2, Feb. 2013, pp. 183-198. DOI: 10.1586/erv.12.150.
Schickli, Jeanne H. et al., "Palivizumab epitope-displaying virus-like particles protect rodents from RSV challenge," The Journal of Clinical Investigation, vol. 125, No. 4, Apr. 2015, pp. 1637-1647.
Whitacre, David C. et al., "Use of hepadnavirus core proteins as vaccine platforms," Expert Review of Vaccines, vol. 8, No. 11, Nov. 2009, pp. 1565-1573.
Rossi, Shannan L. et al., "Characterization of a Novel Murine Model to Study Zika Virus," The American Society of Tropical Medicine and Hygiene, vol. 94, No. 6, 2016, pp. 1362-1369.
Aliota, Matthew T. et al., "Characterization of Lethal Zika Virus Infection in AG129 Mice," PLoS Neglected Tropical Diseases, vol. 10, No. 4: e0004682, Apr. 19, 2016, pp. 1-11.
Kawiecki, Anna B. et al., "Zika Virus-Induced Antibody Response Enhances Dengue Virus Serotype 2 Replication In Vitro," The Journal of Infectious Diseases, vol. 214, No. 9, Nov. 1, 2016, pp. 1357-1360.
Lanciotti, Robert S. et al., "Genetic and Serologic Properties of Zika Virus Associated with an Epidemic, Yap State, Micronesia, 2007," Emerging Infectious Diseases, vol. 14, No. 8, Sep. 2008, pp. 1232-1239.
Boigard, Helene et al., "Zika virus-like particle (VLP) based vaccine," PLoS Neglected Tropical Diseases, vol. 11, No. 5: e0005608, May 8, 2017, pp. 1-20.
Jain, Nishant K. et al., "Formulation and stabilization of recombinant protein based virus-like particle vaccines," Advanced Drug Delivery Reviews, vol. 93, Oct. 1, 2015, pp. 42-55.
Invitation to Respond to Written Opinion, dated Jul. 5, 2021, issued in corresponding Singapore Application No. 11201912454S.
Search Report, dated Jul. 2, 2021, issued in corresponding Singapore Application No. 11201912454S.
First Written Opinion, dated Jul. 2, 2021, issued in corresponding Singapore Application No. 11201912454S.
Ameiss, Keith et all., "Delivery of Woodchuck Hepatitis Virus-like Particle Presented Influenza M2e by Recombinant Attenuated Salmonella Displaying a Delayed Lysis Phenotype," Vaccine, vol. 28, No. 41, 2010, pp. 6704-6713.
Cox, Brian D. et al., "Predicting Zika virus structural biology: Challenges and opportunities for intervention," Antiviral Chemistry and Chemotherapy, vol. 24, No. 3-4, 2015, pp. 118-126.
LaRocca, Rafael A. et al., "Vaccine protection against Zika virus from Brazil," Nature, vol. 536, No. 7617, 2016, pp. 474-478.

* cited by examiner

Serum WHcAg CD Loop

Fluorescence    Bright Field

Serum WHcAg CTRL

Fluorescence    Bright Field

VIRUS-LIKE PARTICLES COMPRISING ZIKA ANTIGEN

CROSS-REFERENCE TO RELATED APPLICATION

This application is a § 371 national stage application of International Application No. PCT/US2018/039079, filed Jun. 22, 2018, which claims the priority benefit under 35 U.S.C. § 119(e) of U.S. Provisional Patent Application No. 62/524,440, filed Jun. 23, 2017, the disclosure of which is incorporated herein by reference in its entirety. The entire disclosure of each of the aforesaid applications is incorporated by reference in the present application.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 52049A_Seqlisting.txt; Size-123,456 bytes, created: Jun. 22, 2018.

FIELD OF THE INVENTION

This invention is related to improved tools for detection of Zika Virus (ZIKV), ZIKV vaccines, and ZIKV diagnostics.

BACKGROUND

Zika virus (ZIKV) is an arbovirus belonging to the Flavivirus genus. ZIKV was first isolated from an infected sentinel monkey in the Zika forest in Uganda (1947), and later in mosquitos [1, 2] and humans in 1954 [3]. No outbreaks were described until 2007 when a ZIKV epidemic on the Island of Yap in the Federated States of Micronesia showed that the virus had the propensity to cause serious disease [4, 5]. Subsequently, ZIKV spread to French Polynesia and Pacific Islands (2013-2014), and recently to the Americas causing very large outbreaks in more than twenty countries including Brazil, Mexico and the Caribbean Islands (2015-present). There is evidence that ZIKV transmission can also occur sexually [6, 7], by blood transfusion and possibly via placenta to infect the fetus [8].

ZIKV is transmitted by mosquitoes of the widely distributed species *Aedes aegypti* and *Aedes albopictus* [4, 5]. According to the Centers for Disease Control (CDC), *Aedes* mosquito species are distributed in many territories of the United States harboring either subtropical or temperate climates. Indeed, ZIKV has caused multiple local infections in the US and US territories, including Puerto Rico, Florida and Texas [9, 10]. ZIKV may continue to spread globally and be introduced in Europe and Australia, and is likely to reemerge in Africa and Asia. ZIKV infection is asymptomatic in a majority (approximately 80%) of people exposed to the virus. Symptoms of infection are similar to other arbovirus diseases, such as Dengue virus (DENV) and Chikungunya Virus (CHIKV), and include fever, maculopapular rash, conjunctivitis, and arthralgia, confounding accurate diagnosis. Importantly, there is a strong association of ZIKV with the autoimmune disease, Guillain-Barré Syndrome (GBS), and congenital malformations resulting in Microcephaly [4, 11].

To date, no prophylactic or therapeutic treatment is commercially available and licensed for ZIKV, despite intensive efforts in this direction.

SUMMARY

The present invention includes a novel ZIKV virus like particle (VLP) and materials and methods for making and using such particles, including formulations and uses as a vaccine, a prophylactic, therapeutic, and diagnostic.

The development of a safe and effective vaccine to protect against ZIKV infection is a high priority objective to reduce the incidence and spread of the severe forms of the disease. An urgent need for the vaccine is also underlined by the impact of the infection on pregnant women and the still unknown implications to men who may become infected.

An ideal vaccine candidate, in addition to having a high safety profile, should also be cost effective and economically viable with ease of large scale manufacture. Live virus vaccines and inactivated virus vaccines are expensive to manufacture due the requirement of highly stringent processes and containment facilities (BSL2 or BSL3), using sophisticated biological production systems (e.g., mammalian cells, eggs). An important caveat with an attenuated vaccine is the safety profile, particularly due to the potential for reversions that may reduce/eliminate attenuation. In the context of a virus like ZIKV, especially if required to be administered to pregnant women, this will be a critical concern.

In the case of inactivated whole virus vaccines, often the inactivation methodologies render epitopes ineffective. Epitope stability is important to the production of completely neutralizing antibodies or protective antibodies.

With the unresolved issue of the role of non-neutralizing and cross-reacting Dengue antibodies enhancing ZIKV infection, similar phenomena may be anticipated in the case of non-neutralizing or partially neutralizing cross-reacting ZIKV antibodies. With the prevalence of diverse strains of ZIKV, and pending information on effective cross-protection between diverse strains, a VLP strategy engineered using highly conserved regions of ZIKV surface glycoproteins, as provided herein, provides significant advantages. This approach will maintain the ZIKV epitope architecture while increasing the possibility of cross-protection across multiple ZIKV strains and cost-effective scale-up. During the last decade, advances in VLP production, purification, and adjuvant optimization led to several licensed vaccines for viral diseases [12] such as human papilloma virus (HPV), hepatitis B virus (HBV), hepatitis E virus (HEV), and influenza. VLPs are more efficient for stimulating the immune system with respect to the subunit proteins because they have the ability to mimic the native morphology of the target virion and they display a repetitive array of epitopes in high concentration. In addition, VLPs are safe due to the absence of replicating viral genetic material [12].

In some aspects, the VLPs disclosed herein are able to cross-protect across different strains of ZIKV. Contrary to other vaccination strategies such as live attenuated vaccines, a VLP strategy as disclosed herein possesses a higher safety profile, particularly for high risk populations such as immunocompromised individuals and pregnant women. In contrast to purified protein vaccines, VLPs of the disclosure express the immunological entity in higher concentration, in an appropriate confirmation (folding) that expresses the epitopes effectively, and with a higher stability profile. From a product development perspective, the technology disclosed herein will also lend itself to facilitated scale-up with defined quality control strategies for large scale production.

Accordingly, in some aspects the invention includes isolated peptides suitable for making Zika vaccines or Zika antibodies or for detecting Zika antibodies. For example, the invention includes an isolated peptide or protein comprising or consisting of an amino acid sequence that is at least 80% identical to a sequence as set out in any one or more of SEQ ID NOs: 2-11, 22-33, 46-47, or 50-51. Genera of peptides with higher minimum percent identity, including 85%, 86%0, 87%, 88%, 89%, 90%0, 91%, 92%, 93%, 94%, 95%, 96%, 97%, 98%, 99% minimum identity to a reference sequence also are contemplated. In some embodiments, the isolated peptide or protein comprises or consists of an amino acid sequence that is 100% identical to a sequence as set out in any one or more of SEQ ID NOs: 2-11, 22-33, 46-47, or 50-51, or an immunogenic fragment thereof. In some aspects, the disclosure provides an isolated peptide comprising or consisting of an amino acid sequence that is at least 80% identical to a sequence as set out in any one or more of SEQ ID NOs: 2-11. In some embodiments, the isolated peptide comprises or consists of an amino acid sequence that is 100% identical to a sequence as set out in any one or more of SEQ ID NOs: 2-11. In some aspects, the disclosure provides an isolated peptide comprising or consisting of an amino acid sequence that is at least 80% identical to a sequence as set out in any one or more of SEQ ID NOs: 22-33. In some embodiments, the isolated peptide comprises or consists of an amino acid sequence that is 100% identical to a sequence as set out in any one or more of SEQ ID NOs: 22-33. In some aspects, the disclosure provides an isolated peptide comprising or consisting of an amino acid sequence that is at least 80% identical to a sequence as set out in any one or more of SEQ ID NOs: 46-47. In some embodiments, the isolated peptide comprises or consists of an amino acid sequence that is 100% identical to a sequence as set out in any one or more of SEQ ID NOs: 46-47. In some aspects, an isolated peptide is provided comprising or consisting of an amino acid sequence that is at least 80% identical to a sequence as set out in any one or more of SEQ ID NOs: 50-51. In some embodiments, the isolated peptide comprises or consists of an amino acid sequence that is 100% identical to a sequence as set out in any one or more of SEQ ID NOs: 50-51.

In related aspects, the invention includes a chimeric peptide comprising a peptide derived from Zika as described herein, including those of the preceding paragraph, linked to a heterologous peptide or protein having an amino acid sequence that is at least 90% identical to a Woodchuck Hepatitis core Antigen protein (WHcAg) comprising or consisting of an amino acid sequence as set out in SEQ ID NO: 1, or comprising or consisting of at least one fragment of SEQ ID NO: 1. In some variations, the Zika-derived peptide portion of the chimeric peptide is inserted within the WHcAg-derived portion. Higher minimum percent identities also are contemplated, as described in the preceding paragraph. In some embodiments, the chimeric peptide further includes at least one peptide linker of 1-10 amino acids linking the sequence that is at least 80% identical to any one or more of SEQ ID NOs: 2-11 or 22-33 or 46-47 or 50-51 to the sequence that is at least 90% identical to a WHcAg protein. In some embodiments, the chimeric peptide comprises or consists of an amino acid sequence at least 90% or at least 95% identical to any one of SEQ ID NOs: 12-21, 34-45, 48-49, and 52-53.

For example, the invention includes a chimeric peptide comprising a Zika-derived peptide as described herein linked to a heterologous peptide having an amino acid sequence that is at least 90% identical to a Woodchuck Hepatitis core Antigen protein (WHcAg) comprising or consisting of an amino acid sequence as set out in SEQ ID NO: 1, wherein the Zika-derived peptide is inserted into the WHcAg-derived peptide at a position between amino acids 77 and 82 of SEQ ID NO: 1.

In related aspects, the invention includes a polynucleotide comprising a nucleotide sequence encoding any of the polypeptides described herein. For example, the invention includes a polynucleotide that comprises a nucleotide sequence that encodes a chimeric peptide described herein. Polynucleotides that are DNA, RNA, and that comprises synthetic or modified nucleotides are contemplated. In some embodiments, the polynucleotide comprises a nucleotide sequence at least 90% identical to or at least 95% identical to any one of SEQ ID NOs: 65-74, 87-98, 101-102, and 105-106.

The invention further includes, in some aspects, a vector comprising a polynucleotide as disclosed herein. In some variations, the vector comprises an expression vector comprising a polynucleotide of the disclosure operably linked to an expression control sequence. Vectors suitable for expression in all varieties of host cells are contemplated, including prokaryotic expression vectors and eukaryotic expression vectors. Exemplary eukaryotic expression vectors include vectors for expression in mammalian cells, insect cells, plant cells, avian cells, amphibian cells, and fungal cells, including yeast cells.

In further aspects, the invention includes a recombinant host cell comprising a vector or expression vector as disclosed herein. In some embodiments, the host cell is (a) a eukaryotic cell selected from the group consisting of mammalian, fungal (e.g., yeast), insect, plant, amphibian and avian cells; or (b) a prokaryotic cell.

The invention also includes a composition comprising a vector as described herein in a pharmaceutically acceptable carrier, diluent, stabilizer, preservative, or adjuvant.

In some aspects, the invention includes a virus-like particle (VLP) comprising or consisting essentially of one or more chimeric peptides or proteins described herein. In further aspects, the invention includes an article comprising a chimeric peptide or protein as described herein or a VLP as described herein attached to a solid support. In some embodiments, the solid support is a microbead, an assay plate, a test strip, or a filter. In some variations, the article further includes a distinct peptide attached to the article, optimally at a spatially distinct location, that can serve as a positive or negative control in assays described herein. In still other variations, the article is packaged as part of a kit with at least one assay reagent, such as an immunoassay reagent.

The invention also includes a composition comprising a peptide or protein described herein, or a chimeric peptide or protein described herein, and a pharmaceutically acceptable diluent, adjuvant, excipient, stabilizer, preservative, or carrier. In some variations, the disclosure provides an antigenic composition comprising a VLP as disclosed herein, wherein the VLP is present in the composition at a concentration of about 0.1-2000 μg/ml of core antigen, in a pharmaceutically acceptable carrier, diluent, stabilizer, preservative, or adjuvant.

In still additional variations, the invention includes an antigenic composition comprising two or more different polypeptides, chimeric polypeptides, or VLP's described herein. For instance, the invention includes first and second VLP described herein, wherein the first and second VLP comprise different sequences independently selected from amino acid sequences at least 80% identical to SEQ ID NOs: 2-11, 22-33, 46-47, and 50-51. For embodiments of this nature, ordinals such as "first" or "second" are intended simply to differentiate one from another, and are not intended to imply an order. Such compositions optionally further includes a pharmaceutically acceptable diluent, adjuvant, excipient, stabilizer, preservative, or carrier.

In a related embodiment, the invention is an antigenic composition comprising first, second, and third VLP as described herein. For instance, the first, second, and third VLP comprise different sequences independently selected from amino acid sequences at least 80% identical to SEQ ID NOs: 2-11, 22-33, 46-47, and 50-51.

In another related embodiment, the invention is an antigenic composition comprising first, second, third, fourth, fifth, sixth, and seventh VLP as described herein. For example, the first, second, third, fourth, fifth, sixth, and seventh VLP comprise different sequences independently selected from SEQ ID NOs: 2-11, 22-33, 46-47, and 50-51.

The invention also includes a kit comprising a VLP as described herein, or comprises an article of manufacture as described herein, packaged with at least one reagent useful for performing an immunoassay. Exemplary suitable reagents include an enzyme substrate, a detection antibody, positive and negative control reagents, substrate/s detection solution, and washing, blocking, and diluent buffer. In some embodiments, the kit includes a specific apparatus used for the execution of the protocol and for the detection.

The invention further includes an antigenic composition comprising a peptide, a chimeric peptide or chimeric protein, or a VLP as described herein in a pharmaceutically acceptable carrier, diluent, stabilizer, preservative, or adjuvant, wherein the composition is capable of generating an immune response to a Zika virus. An exemplary immune response includes antibody generation or a protective immune response in a mammalian subject. Desirably, the antibody response generated by the composition is improved relative to or compared to an immune response achieved with live Zika virus or Zika Envelope (E) recombinant protein. In some variations, the antibody response is a protective and functional against Zika virus by neutralizing activity, and/or antibody dependent cell-mediated cytotoxicity (ADCC), and/or antibody dependent cell-mediated phagocytosis (ADCP), and/or complement-dependent cytotoxicity (CDC), and/or T cell response (e.g. CD4+ and CD8+) and/or other protective immune mechanisms.

In still additional embodiments, the invention includes a vaccine comprising a peptide, chimeric peptide, chimeric protein, VLP, or antigenic composition as described herein and an adjuvant. In some embodiments, the adjuvant is a polymeric particle, cholera toxin, or imidazoquinoline. In further embodiments, the adjuvant formulations include the classical aluminum-based adjuvants, and novel classes of adjuvants such as liposomes (e.g., CAF01), agonists of pathogen recognition receptors (e.g. Immune stimulating complexes (ISCOMs), Lipid A analogs (MPL, RC-529, and GLA), double stranded RNA analogs (e.g. Poly I:C and Poly ICLC), cytidine monophosphate guanosine oligodeoxynucleotide (e.g. CpG, CpG ODN), flagellin, imidazoquinoline (Imiquimod and Resiquimod), polymeric particles (e.g. Chitosan), emulsions (e.g. squalene oil-based), cytokines (e.g. Interleukin-12), bacterial toxins (e.g Cholera Toxin (CT) or *Escherichia coli* enterotoxin (LT)), Quil A and other saponins known in the art, and the plant polysaccharide inulin [12].

The invention also includes methods of making and methods of using any of the foregoing compounds, compositions, articles of manufacture, apparatuses, and/or materials. Furthermore, it should be understood that aspects of the inventions that are described herein as methods can alternatively be described as "uses" of the compounds, compositions, articles, apparatuses and/or materials. All equivalent "uses" are also contemplated as aspects of the invention.

In some variations, the invention includes a method of producing an immune response to a Zika virus in a subject, the method comprising administering to the subject an effective amount of an antigenic composition or a vaccine as described herein, thereby producing (causing the subject's immune system to generate) an immune response to a Zika virus in the subject. In related variations, the disclosure provides an antigenic composition or vaccine for use in producing an immune response to a Zika virus in a subject characterized in that producing the immune response comprises administering to the subject an effective amount of an antigenic composition or a vaccine as described herein, thereby producing (causing the subject's immune system to generate) an immune response to a Zika virus in the subject.

In some variations, the invention includes a method of treating a Zika virus infection in a subject in need thereof, the method comprising administering to the subject an effective amount of an antigenic composition described herein, thereby treating a Zika virus infection in the subject. In related variations, the disclosure provides an antigenic composition for use in treating a subject in need thereof, characterized in that the treating comprises administering to the subject an effective amount of an antigenic composition described herein, thereby treating a Zika virus infection in the subject.

In still additional variations, the invention includes a method of preventing a disease or disorder caused by a Zika virus infection in a subject, the method comprising administering to the subject an effective amount of an antigenic composition or a vaccine as described herein, in an amount effective to prevent a disease or disorder caused by a Zika virus infection in the subject. In related variations, the disclosure provides an antigenic composition or a vaccine for use in preventing a disease or disorder caused by a Zika virus infection in a subject, characterized in that the use comprises administering to the subject an effective amount of an antigenic composition or a vaccine as described herein, in an amount effective to prevent a disease or disorder caused by a Zika virus infection in the subject.

The invention also includes a method of protecting a subject from developing one or more symptoms of Zika virus infection, the method comprising administering to the subject a vaccine composition as described herein, in an amount effective to protect the subject from developing one or more symptoms of Zika virus infection. In related variations, the method is effective to reduce the number, severity, or duration of symptoms of a Zika virus infection. In some embodiments, the reduction in symptoms is measured as a reduction in viral load or viral copy number in the subject. In further aspects, the disclosure provides a vaccine composition for use in protecting a subject from developing symptoms of Zika virus infection, characterized in that the protecting comprises administering to the subject a vaccine composition as described herein, in an amount effective to protect the subject from developing symptoms of Zika virus infection.

In still another related embodiment, the invention includes a method of immunizing a mammalian subject against a Zika virus infection comprising administering to the subject an effective amount of an antigenic composition described herein or a vaccine described herein. In some aspects, the disclosure provides an antigenic composition or a vaccine of the disclosure for use in immunizing a mammalian subject against a Zika virus infection, characterized in that the immunizing comprises administering to the subject an effective amount of an antigenic composition described herein or a vaccine described herein.

In some aspects, the disclosure provides a method of protecting a subject from sexual transmission of Zika virus, comprising administering to the subject an effective amount of an antigenic composition or vaccine of the disclosure, thereby protecting the subject from sexual transmission of Zika virus. In some aspects, the disclosure provides an antigenic composition or a vaccine for use in protecting a subject from sexual transmission of Zika virus, characterized in that the protecting comprises administering to the subject an effective amount of an antigenic composition or vaccine of the disclosure, thereby protecting the subject from sexual transmission of Zika virus. In some embodiments, the administering is mucosal administration. In further embodiments, the mucosal administration is nasal, vaginal, rectal, or oral.

The materials and methods described herein also are useful for quantifying or detecting a Zika immune response after infection and/or vaccination. For instance, the invention includes a method of detecting or measuring antibodies to Zika virus in a biological sample comprising:
 a) contacting a VLP as described herein with a biological sample under conditions suitable for the formation of an antigen-antibody complex; and
 b) measuring or detecting antibodies to Zika virus by detecting or measuring an antigen-antibody complex formed between antibodies in the biological sample and the VLP.

The invention further includes a method of detecting a Zika virus infection comprising steps of:
 a) contacting the VLP as described herein with a biological sample from a mammalian subject under conditions suitable for the formation of an antigen-antibody complex; and
 b) detecting the antigen-antibody complex formed between the VLP and antibodies in the biological sample, thereby detecting the Zika virus infection.

In some variations, the foregoing method further comprises a step of detecting the Zika virus in the biological sample, wherein presence of the Zika virus indicates a current Zika virus infection.

The invention also includes a method for screening antibodies comprising steps of:
 a) measuring binding of an antibody or fragment thereof to a VLP as described herein;
 b) measuring binding of the antibody or fragment thereof to a Woodchuck Hepatitis core Antigen protein (WHcAg) VLP or protein; and
 c) determining that the antibody or fragment thereof is an anti-Zika antibody when the antibody or fragment thereof binds to the VLP but not the WHcAg.
Such a method is particularly useful for evaluating antibodies produced following an immunization with VLP described herein and/or Zika virus infection.

In any of the foregoing methods, some variations involving using the VLP in solution or suspension. In other variations, the VLP is attached to a solid support, such as any of a microbead, an assay plate, a test strip, or a filter.

The invention also includes methods of making the VLP described herein. For instance, the invention includes a method of producing a VLP comprising introducing into a host cell the vector of claim 6 under conditions such that the cell produces the VLP. In some variations, the host cell is a eukaryotic cell, such as a mammalian cell, a fungal or yeast cell, an insect cell, a plant cell, an amphibian cell, or an avian cell. In still other variations, the cell is a prokaryotic cell, such as a bacterial cell. An exemplary yeast host cell is a *Pichia pastoris* cell (e.g., *Komagataella phaffii* Kurtzman (ATCC® 76273™)). In some variations, the vector is introduced into the host cell via transformation, transfection, transduction, or electroporation. In some variations, the cells are cultured at temperatures ranging from 25° C. to 37° C. in an incubator or fermenter or shaker, in continuous agitation and oxygenation. Optionally, the VLP produced according to such a method is purified from the host cell or a culture media of the host cell. Exemplary suitable procedures for VLP purification include precipitation, ultracentrifugation, density gradient ultracentrifugation, ultrafiltration such as tangential flow filtration (TFF) and other methods, chromatography, or a combination thereof.

The invention also includes a VLP produced by any of the foregoing methods.

Reference throughout this specification to "one embodiment", "some embodiments" or "an embodiment" means that a particular feature, structure or characteristic described in connection with the embodiment is included in at least one embodiment of the present disclosure. The particular features, structures, or characteristics described herein may be combined in any suitable manner, and all such combinations are contemplated as aspects of the invention.

Unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

The headings herein are for the convenience of the reader and not intended to be limiting. Additional aspects, embodiments, and variations of the invention will be apparent from the Detailed Description and/or Drawing and/or claims.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office or other entity or individual, the Applicant reserves the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIGS. 3A and 3B depict the structural vaccinology strategy that was applied for developing WHcAg-ZIKV chimeric VLPs using the Envelope protein Domain III (EDIII). In FIG. 3B the EDIII sub-structural domain CD Loop is included for composition of the WHcAg-ZIKV chimeric VLP.

FIG. 6A demonstrates WHcAg production and purification form *Pichia* culture, WHcAg VLPs are detected using the commercially available monoclonal antibody HepBcAg. FIGS. 6B and 6C show WHcAg-ZIKV chimeric VLPs antigenicity using commercially available monoclonal antibodies such as ZV-2 and ZV-54 specific for ZIKV EDIII.

FIG. 7 illustrates dot blot analysis for WHcAg-ZIKV chimeric VLPs antigenicity using anti-Zika virus antibody for mouse serum, prME VLPs and ZIKV E recombinant protein are used as a positive controls for the assay.

FIG. 10 shows immunofluorescence microscopy experiment demonstrating that serum form immunized mice with WHcAg CD loop VLP vaccine candidate induces antibodies able to recognize Zika virus in infected Vero cell in culture (left panel); the serum from the placebo control is used as a negative control in such experiment (right panel).

FIG. 11A shows antibody dependent cell-mediated cytotoxicity (ADCC) assay: mouse serum immunized with WHcAg CD loop VLPs exert protective activity of antibodies against Zika Virus; the serum from animals immunized with placebo control WHcAg CTRL is included as a negative control and serum from an animal immunized with live Zika virus (#426) is used as an additional control. FIG. 11B illustrates complement dependent cytotoxicity (CDC) assay: WHcAg CD loop VLPs induces CDC activity in mice immunized with such vaccine candidate in respect placebo controls (WHcAg CTRL) and an animal immunized with live Zika virus (#426).

FIG. 13 is a depiction of a test strip of the invention and of detection of Zika virus infection using viral epitopes expressed in VLPs using a Lateral Flow Immunoassay (LFIA) system (see Example 5).

DETAILED DESCRIPTION

Figure 1:
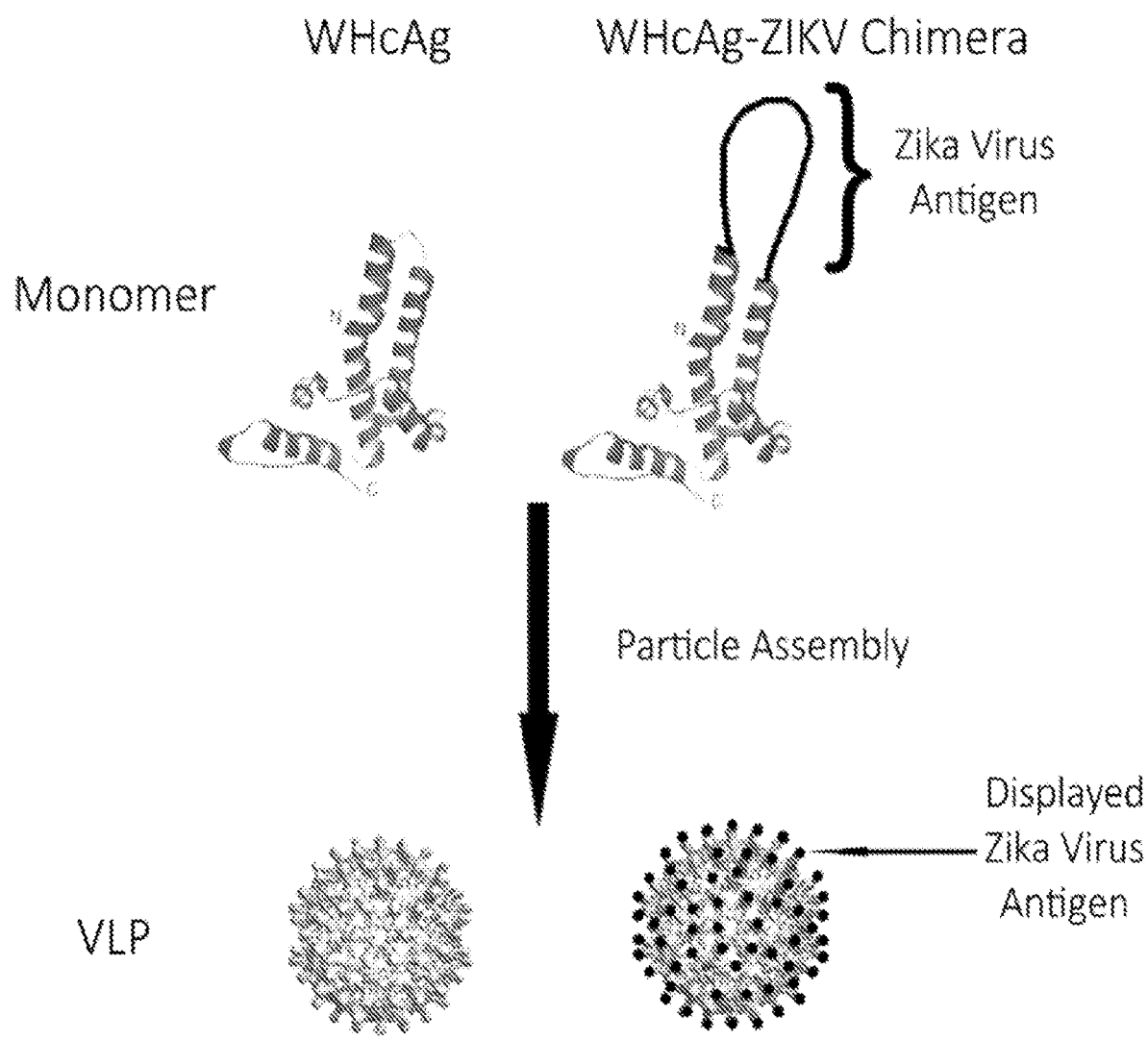
FIG. 1 depicts elements of the WHcAg VLP system as disclosed herein for epitope delivery. The depictions on the left show a WHcAg core antigen peptide and VLP comprised of such peptides. The images on the right show a chimeric peptide of the invention and a VLP comprised of such peptides. The dark black portions depict the displayed ZIKV epitope.

The morphology of VLPs is pivotal for their strong immune-stimulatory activity: i) VLPs are more efficiently recognized by antigen presenting cells (APCs); ii) VLPs are trafficked from the site of injection to the lymph nodes; iii) the VLP structure presents a repetitive arrangement of antigens that stimulates B-cells for the humoral immune response, and T-cells for cell mediated immune response [13, 14].

The majority of FDA approved VLP-based vaccines are currently manufactured in yeast due to ease of scalability. Aspects of the present invention are directed to a ZIKV VLP (ZIK-VLP)-based vaccine and uses of it. In some embodiments, the VLP is produced using a yeast expression system, applying structural vaccinology for the optimization of VLP immunogenicity: antigen determinants are selectively engineered for achieving high level of immunogenicity, ZIKV specificity, and enhanced inter-strain protection [15, 16].

Terms used herein generally have the meaning that scientists in the field would ascribe to them. The following definitions will assist understanding of the invention.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

"Conservative amino acid substitution" refers to the interchange of a residue having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "nucleic acid" refers to a single or double-stranded polymer of deoxyribonucleotide or ribonucleotide bases read from the 5' to the 3' end.

The term "encoding" refers to a polynucleotide sequence encoding one or more amino acids. The term does not require a start or stop codon. An amino acid sequence can be encoded in any one of six different reading frames provided by a double-stranded polynucleotide sequence. In some variations, encoding sequences further include a start and/or a stop codon.

A "vector" refers to a polynucleotide, which when independent of the host chromosome, is capable of replication in a host organism. Examples of vectors include plasmids. Vectors typically have an origin of replication. Vectors can comprise, e.g., transcription and translation terminators, transcription and translation initiation sequences, and promoters useful for regulation of the expression of the particular nucleic acid.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified and that retains the modification, such as a daughter cell. Thus, for example, recombinant cells express genes that are not found within the native (nonrecombinant) form of the cell or express native genes that are otherwise abnormally expressed, under-expressed or not expressed at all.

The terms "identical" or percent "identity," in the context of two or more nucleic acids or polypeptide sequences, refer to two or more sequences or subsequences that are the same. "Substantially identical" refers to two or more nucleic acids or polypeptide sequences having a specified percentage (or specified minimum percentage) of amino acid residues or nucleotides that are the same (i.e., (at least) 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the sequence comparison algorithms below or by manual alignment and visual inspection. This definition also refers to the complement of a test sequence. Optionally, the identity or substantial identity exists over a region that is at least about 50 nucleotides in length, or more preferably over a region that is 100 to 500 or 1000 or more nucleotides or amino acids in length.

A "non-native amino acid" in a protein sequence refers to any amino acid other than the amino acid that occurs in the corresponding position in an alignment with a naturally-occurring polypeptide with the lowest smallest sum probability where the comparison window is the length of the monomer domain queried and when compared to a naturally-occurring sequence in the non-redundant ("nr") database of Genbank using BLAST 2.0. BLAST 2.0 is described in the art [17], respectively. Software for performing BLAST analyses is publicly available through the National Center for Biotechnology Information (available on the world wide web at ncbi.nlm.nih.gov/).

As used herein, the terms "virus-like particle" and "VLP" refer to a structure that resembles a virus. VLPs of the present disclosure lack a viral genome and are therefore noninfectious. Preferred VLPs of the present disclosure are derived from Woodchuck Hepatitis core Antigen (WHcAg) and thus have a VLP structure or arrangement similar to WHcAg VLPs. Virus-like particles show improved efficiency in stimulating the immune system because they resemble the morphology of a virion displaying a densely repetitive array of epitopes in a limited space. Furthermore, VLPs are very safe candidates for vaccine development due to their lack of replicating viral genetic material rendering them unable to cause viral disease. During the last decade, advancement in VLP production, purification, and adjuvant optimization has led to the licensing of several VLP-based vaccines for the prevention of infectious diseases [12] such as human papilloma virus (HPV), hepatitis B virus (HBV), hepatitis E virus (HEV), and influenza. Furthermore, several clinical trials are currently ongoing for VLP vaccines against influenza, norovirus, and chikungunya virus (CHIK) (available on the world wide web at clinicaltrials.gov/).

The term "Woodchuck Hepatitis Virus" is used interchangeably herein with the term "Woodchuck Hepadnavirus" and refers to the virus species that expresses the core Antigen protein used as a platform for recombinant VLPs.

The term "chimeric" refers to a fusion of polypeptide and/or peptides sequences. "Chimeric" as used in reference to a Woodchuck Hepatitis core Antigen (WHcAg) refers to a fusion protein of the WHcAg and an unrelated antigen (e.g., a viral peptide and variants thereof). For instance, in some embodiments, the term "chimeric peptide" or "chimeric protein" refers to a fusion protein comprising both a WHcAg component (full length, or partial) and a Zika peptide or a fragment thereof. As described herein, some fusions take the form of insertions, where a Zika sequence is inserted within a WHcAg sequence.

The term "heterologous" with respect to a nucleic acid, or a polypeptide component, indicates that the component occurs where it is not normally found in nature (e.g., relative to an adjacent component) and/or that it originates from a different source or species.

An "effective amount" or a "sufficient amount" of a substance is that amount necessary to effect beneficial or desired results, including clinical results, and, as such, an "effective amount" depends upon the context in which it is being applied. In the context of administering an antigenic composition, an effective amount contains sufficient antigen (e.g., a VLP comprising a chimeric peptide of the disclosure) to elicit an immune response. An effective amount can be administered in one or more doses. Efficacy can be shown in an experimental or clinical trial, for example, by comparing results achieved with a substance of interest compared to an experimental control.

The term "dose" as used herein in reference to an antigenic composition refers to a measured portion of the antigenic composition taken by (administered to or received by) a subject at any one time.

The term "about" as used herein in reference to a value, encompasses from 90% to 110% of that value (e.g., about 200 µg VLP refers to 180 µg to 220 µg VLP).

The term "vaccination" as used herein refers to the introduction of vaccine into a body of an organism.

A "subject" is a living multi-cellular vertebrate organism. In the context of this disclosure, the subject can be an experimental subject, such as a non-human mammal (e.g., a mouse, a rat, or a non-human primate). Alternatively, the subject can be a human subject.

An "antigenic composition" is a composition of matter suitable for administration to a human or animal subject (e.g., in an experimental or clinical setting) that is capable of eliciting a specific immune response, e.g., against a pathogen, such as Zika virus.

As such, an antigenic composition includes one or more antigens (for example, peptide antigens) or antigenic epitopes. An antigenic composition can also include one or more additional components capable of eliciting or enhancing an immune response, such as an excipient, carrier, and/or adjuvant. In certain instances, antigenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., virus) following exposure of the subject to the pathogen. In the context of this disclosure, the term antigenic composition will be understood to encompass compositions that are intended for administration to a subject or population of subjects for the purpose of eliciting a protective or palliative immune response against a virus.

"Adjuvant" refers to a substance which, when added to a composition comprising an antigen, nonspecifically enhances or potentiates an immune response to the antigen in the recipient upon exposure. Common adjuvants include suspensions of minerals (alum, aluminum hydroxide, aluminum phosphate) onto which an antigen is adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Pattern Recognition Receptor (PRR) agonists (e.g. NALP3. RIG-I-like receptors (RIG-I and MDA5), and Toll-like Receptor agonists (particularly, TLR2, TLR3, TLR4, TLR7/8 and TLR9 agonists)), and various combinations of such components [12].

An "immune response" is a response of a cell of the immune system, such as a B cell, T cell, or monocyte, to a stimulus, such as a pathogen or antigen (e.g., formulated as an antigenic composition or a vaccine). An immune response can be a B cell response, which results in the production of specific antibodies, such as antigen specific neutralizing antibodies. An immune response can also be a T cell response, such as a $CD4^+$ response or a $CD8^+$ response. B cell and T cell responses are aspects of a "cellular" immune response. An immune response can also be a "humoral" immune response, which is mediated by antibodies. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by viral and immune assays using a serum sample from an immunized subject for testing the ability of serum antibodies for inhibition of viral replication, such as: plaque reduction neutralization test (PRNT), ELISA-neutralization assay, antibody dependent cell-mediated cytotoxicity assay (ADCC), complement-dependent cytotoxicity (CDC), antibody dependent cell-mediated phagocytosis (ADCP). In addition, vaccine efficacy can be tested by measuring the T cell response CD4+ and CD8+ after immunization, using flow cytometry (FACS) analysis or ELISpot assay. The protective immune response can be tested by measuring resistance to pathogen challenge in vivo in an animal model. In humans, a protective immune response can be demonstrated in a population study, comparing measurements of infection, symptoms, morbidity, mortality, etc. in treated subjects compared to untreated controls. Exposure of a subject to an immunogenic stimulus, such as a pathogen or antigen (e.g., formulated as an antigenic composition or vaccine), elicits a primary immune response specific for the stimulus, that is, the exposure "primes" the immune response. A subsequent exposure, e.g., by immunization, to the stimulus can increase or "boost" the magnitude (or duration, or both) of the specific immune response. Thus, "boosting" a preexisting immune response by administering an antigenic composition increases the magnitude of an antigen (or pathogen) specific response, (e.g., by increasing antibody titer and/or affinity, by increasing the frequency of antigen specific B or T cells, by inducing maturation effector function, or a combination thereof).

An "improved" antibody response is measured by a difference such as: protection from Zika Virus replication and viremia; neutralizing antibody titer; antibody dependent cell-mediated cytotoxicity (ADCC); complement dependent cytotoxicity (CDC), antibody dependent cell-mediated phagocytosis (ADCP); stimulation of B cell immune memory; activation of immune cells such as B cells, T cell and Antigen Presenting Cells (APC); protection from disease symptoms such as fever, pain, weight loss; weakness, maculopapular rash, Zika Congenital Syndrome (microcephaly), Guillain-Barré Syndrome. Such differences are measured in a population study in which treated subjects are compared with untreated control subjects.

The phrase "specifically (or selectively) binds," when referring to the interaction between an antibody or fragment thereof and a VLP, a peptide, a chimeric protein, or a chimeric peptide as disclosed herein, refers to a binding reaction that can be determinative of the presence of the polypeptide in a heterogeneous population of proteins (e.g., a cell or tissue lysate) and other biologics. Thus, under standard conditions used in antibody binding assays, the specified VLP, peptide, or chimeric peptide binds to a particular target antibody or fragment thereof above background (e.g., 2×, 5×, 10× or more above background) and does not bind in a significant amount to other molecules present in the sample. Of particular interest herein are antibodies that recognize Zika virus but not Dengue virus or other flaviviruses.

As used herein, an "expression vector" is a DNA construct that contains a structural gene operably linked to an expression control sequence so that the structural gene can be expressed when the expression vector is transformed into an appropriate host cell. Two DNA sequences are said to be "operably linked" if the biological activity of one region will affect the other region and also if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that desired DNA sequence. As described herein, vectors suitable for expression in all varieties of host cells are contemplated, including prokaryotic expression vectors and eukaryotic expression vectors. Exemplary eukaryotic expression vectors include vectors for expression in mammalian cells, avian cells, insect cells, amphibian cells, plant cells, and fungal cells, including yeast cells.

Conventional or known techniques of molecular biology (including recombinant techniques), microbiology, cell biology, biochemistry and immunology can be used to implement many elements of the invention. Such techniques are not always described herein in detail because they are known and/or are explained fully in the literature, such as, Molecular Cloning: A Laboratory Manual, second edition (Sambrook et al., 1989); Current Protocols in Molecular Biology (Ausubel et al., eds., 1987); PCR: The Polymerase Chain Reaction, (Mullis et al., eds., 1994); Culture of Animal Cells: A Manual of Basic Technique (Freshney, 1987); Harlow et al., Antibodies: A Laboratory Manual (Harlow et al., 1988); and Current Protocols in Immunology (Coligan et al., eds., 1991).

As used in this specification and the appended claims, the singular forms "a," "an," and "the" include plural reference unless the context clearly dictates otherwise.

Zika Virus

Zika virus (ZIKV), a Flaviviridae family member, is a single-stranded, positive-sense RNA virus with an approximate 10.7 Kb genome encoding a single polyprotein that is cleaved into three structural proteins (C, prM/M, and E) and seven non-structural proteins (NS1, NS2A, NS2B, NS3, NS4A, NS4B, and NS5) by viral and host proteases [4, which is incorporated by reference herein in its entirety]. The overall structure of ZIKV soluble envelope (E) protein resembles previously reported flavivirus E protein structures and has three distinct domains: a central b-barrel (domain I or domain 1), an elongated finger-like structure (domain II or domain 2), and a C-terminal immunoglobulin-like module (domain III or domain 3) [18]).

Chimeric Peptide Constructs

Some aspects of the invention comprise chimeric peptide or protein constructs having at least one portion comprised of, or derived from, a rodent hepadnavirus core antigen attached to at least one portion comprised of, or derived from, a Zika virus protein antigen. In some embodiments, the portions are joined by peptide bonds to form a chimeric polypeptide, as described below in greater detail.

A. Rodent Hepadnavirus Core Antigens

In some aspects, the chimeric hepadnavirus portion of the chimeric construct is engineered from a rodent hepadnavirus core antigen amino acid sequence. For instance, one or more endogenous B cell epitopes from the native core antigen amino acid sequence are effectively removed. Hepadnavirus core antigens are generally described in U.S. Patent Application Publication No. 2016/0022801, which is incorporated by reference herein in its entirety.

Exemplary rodent hepadnavirus core antigens suitable for this component/portion of the chimeric construct include woodchuck (WHcAg), ground squirrel (GScAg), arctic ground squirrel (AGScAg) and human (HBcAg) hepadnavirus core antigens. An exemplary amino acid sequence of woodchuck hepadnavirus core antigen is set out in SEQ ID NO: 1, and is also available as GenBank accession number NP_671816. Rodent hepadnavirus core antigens have a number of properties that make them particularly useful for making the chimeric constructs described herein. For instance, they will self-aggregate/assemble into a multimeric complex or VLP. The basic subunit of the core particle is a 21 kDa protein monomer (schematically depicted in FIG. 1, top left) that spontaneously assembles into a 240 subunit particulate structure of about 34 nm in diameter (FIG. 1, bottom left). The tertiary and quaternary structures of hepadnavirus core particles have been elucidated [19, incorporated herein by reference]. The immunodominant B cell epitope on WHcAg is localized around amino acids 76-82 of SEQ ID NO: 1 [20] forming a loop connecting adjacent alpha-helices. This observation is consistent with the finding that a heterologous antigen inserted within the 76-82 loop region of HBcAg was significantly more antigenic and immunogenic than the antigen inserted at the N- or C-termini and, importantly, more immunogenic than the antigen in the context of its native protein [20].

In some embodiments, the chimeric constructs of the invention are comprised of a hepadnavirus portion that is based on a woodchuck hepadnavirus core antigen. For example, the portion used, when aligned with SEQ ID NO:1, has an amino acid sequence that is at least 90% (e.g., at least 90%, 91%, 92%, 93%, 94%, 95%, 96%, 97%, 98%, or 99% identical) to SEQ ID NO:1. The amino acid variation, relative to wildtype, can be any variation that does not destroy the self-assembling properties of the wildtype protein. In some variations, the variation does not increase antigenicity of the protein, compared to wildtype. In some variations, the changed amino acids are conservative substitution variants. Sequence variation can also be expressed as a limited number (e.g., 1, 2, 3, 4, 5, 6, 7, 8, 9, or 10) amino acid sequence differences between the wildtype sequence and the aligned sequence used in the present invention.

As described below, the chimeric construct preferably comprises a Zika peptide or polypeptide sequence insert that disrupts and/or replaces the B cell epitope region of the core antigen sequence. For purposes of sequence identity analysis in the preceding paragraphs, the changes to the B cell epitope and the Zika insert are ignored.

B. Zika-Derived Peptides

A peptide or protein identical to or derived from a Zika virus amino acid sequence is used in the chimeric constructs of the invention. The Zika portion has been chosen for its immunogenicity properties. In preferred variations, the Zika portion comprises, or is derived from, a Zika Virus Envelope (E), NS1, prM, or C protein. In some variations, the Zika portion comprises, or is derived from, domain 3 of a Zika Virus E protein. An exemplary domain 3 sequence is set forth in SEQ ID NO: 2. The use of peptides with sequence variation is contemplated, so long as the peptide still comprises sequence that acts as an epitope that will generate an immune response that recognizes wildtype Zika protein or wildtype Zika virus. For instance, the peptide or protein used comprises an amino acid sequence that is at least 90% (e.g., at least 90%, 91%, 92%, 93%, 94%, 95%, 96%, 97%, 98%, or 99% identical) to SEQ ID NO: 2. Sequence variation can also be expressed as a limited number (e.g., 1, 2, 3, 4, 5, 6, 7, 8, 9, or 10) amino acid sequence differences between the wildtype sequence and the aligned sequence used in the present invention. In some variations, the Zika portion comprises, or is derived from, NS1. An exemplary NS1 sequence is set forth in SEQ ID NO: 22. The use of peptides with sequence variation is contemplated, so long as the peptide still comprises sequence that acts as an epitope that will generate an immune response that recognizes wildtype Zika NS1 protein or wildtype Zika virus. For instance, the peptide used comprises an amino acid sequence that is at least 90% (e.g., at least 90%, 91%, 92%, 93%, 94%, 95%, 96%, 97%, 98%, or 99% identical) to SEQ ID NO: 22. Sequence variation can also be expressed as a limited number (e.g., 1, 2, 3, 4, 5, 6, 7, 8, 9, or 10) amino acid sequence differences between the wildtype sequence and the aligned sequence used in the present invention. In some variations, the Zika portion comprises, or is derived from, prM/M protein. An exemplary prM/M protein sequence is set forth in SEQ ID NO: 46. The use of peptides with sequence variation is contemplated, so long as the peptide still comprises sequence that acts as an epitope that will generate an immune response that recognizes wildtype Zika prM/M protein or wildtype Zika virus. For instance, the peptide used comprises an amino acid sequence that is at least 90% (e.g., at least 90%, 91%, 92%, 93%, 94%, 95%, 96%, 97%, 98%, or 99% identical) to SEQ ID NO: 46. Sequence variation can also be expressed as a limited number (e.g., 1, 2, 3, 4, 5, 6, 7, 8, 9, or 10) amino acid sequence differences between the wildtype sequence and the aligned sequence used in the present invention.

In some embodiments, the peptide derived from Zika is a polypeptide of from 4 to 200 amino acids in length. In some embodiments, the peptide is from 5 to 150 amino acids in length, or from 5 to 100 amino acids in length, or from 5 to 55 amino acids in length, preferably 10 to 50 amino acids in length, preferably 15 to 45 amino acids in length, or preferably 20 to 40 amino acids in length. In some embodiments, the length of the peptide is within any range having a lower limit of 4, 5, 6, 7, 8, 9, 10, 11, 12, 13, 14, 15, 16, 17, 18, 19 or 20 amino acids and an independently selected upper limit of 200, 195, 190, 185, 180, 175, 170, 165, 160, 155, 150, 145, 140, 135, 130, 125, 120, 115, 110, 105, 100, 95, 90, 85, 80, 75, 70, 65, 60, 55, 50, 45, 40, 35, 30, 25 or 20 amino acids in length, provided that the lower limit is less than the upper limit. All integer lengths from 4-200 amino acids are specifically contemplated.

In some embodiments, the peptide derived from Zika is itself a fusion protein comprising fragments of two, three, four or five different Zika peptides. In various embodiments, the peptide comprises or consists of an amino acid sequence that is at least 80% identical to a sequence as set out in any one or more of SEQ ID NOs: 2-11, 22-33, 46-47, or 50-51. In further embodiments, the peptide is 100% identical to a sequence as set out in any one or more of SEQ ID NOs: 2-11, 22-33, 46-47, or 50-51.

As described more fully below, the core antigen used herein is modified to include one or more Zika virus epitopes.

C. Combinatorial Technology

In some embodiments, the peptide derived from Zika is inserted into the peptide derived from the Hepadnavirus core protein (schematically depicted in FIG. 1, right top) at a location that preserves the self-assembly properties of the core protein and that presents the peptide or protein derived from Zika in an antigenic manner (FIG. 1, right bottom).

Several groups working with the HBcAg or with other VLP technologies (e.g., the L1 protein of the human papillomavirus and Qβ phage) have opted to chemically link the foreign epitopes to the VLPs rather than inserting the epitopes into the particles by recombinant methods. Such embodiments are contemplated as one aspect of the invention. The chemically conjugation approach for linking heterologous antigens has been circumvented by identification of suitable insertions sites for chimeric proteins, identifiable, e.g., by combinatorial technology. (See [21]). Such techniques were used to determine 17 different insertion sites and 28 modifications of the WHcAg C-terminus that together favor assembly of chimeric particles, as well as the identification of a number of additional improvements (see, e.g., U.S. Pat. Nos. 7,144,712; 7,320,795; and 7,883,843, all incorporated herein by reference). ELISA-based screening systems have been developed that measure expression levels, VLP assembly, and insert antigenicity using crude bacterial lysates, avoiding the need to employ labor-intensive purification steps for VLPs that do not express and/or assemble well.

A number of insertion sites inside the loop region (positions 76-82), as well as outside the loop region are tolerated by WHcAg. In some embodiments, the peptides or proteins are inserted directly or optionally with linker(s) at one or both ends of the Zika peptide. For example, the chimeric peptides or proteins set out in SEQ ID NOs: 12-21, 34-45, 48-49, and 52-53 contain portions that originate from the WHcAg (the non-underlined sequences in each of SEQ ID NOs: 12-21, 34-45, 48-49, and 52-53) and portions that are the peptide derived from Zika (the underlined sequences in SEQ ID NOs: 12-21, 34-45, 48-49, and 52-53).

Figure 3:
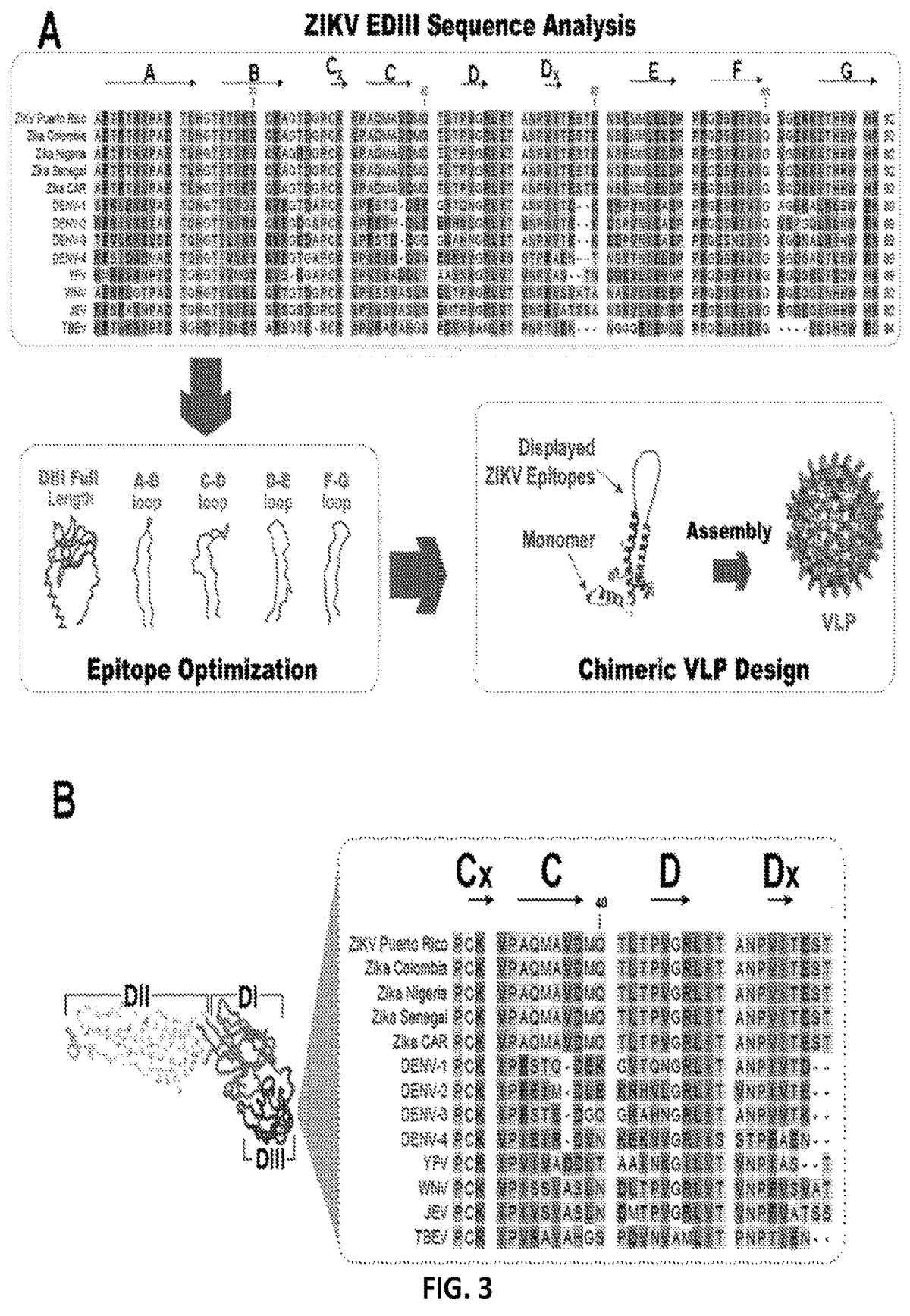

SEQ ID NOs: 2-11 were obtained via structure analysis of Envelope (E) protein (see Examples and FIG. 3). The sequences were selected for their adaptability with the scaffolding system, i.e., the Woodchuck Hepatitis core Antigen (WHcAg) protein (Table 1). Specifically, SEQ ID NOs: 2-7 were generated from the Envelope Domain 3 with amino acid sequence very specific for Zika Virus. SEQ ID NO: 8 was generated from Fusion Loop Domain that shares very similar amino acid sequence between flavivirus (e.g., Dengue Virus, Yellow Fever Virus, West Nile Virus). SEQ ID NOs: 9 and 10 were generated from Envelope Domain 2 with amino acid sequence very specific for Zika Virus. Finally, SEQ ID NO: 11 was generated from Envelope Domain 1 with amino acid sequence very specific for Zika Virus.

TABLE 1

| SEQUENCE ID NO | VIRUS-LIKE PARTICLE PROTEIN | AMINO ACID SEQUENCE |
|---|---|---|
| 1 | Woodchuck Hepatitis Core Antigen (WHcAg) | MDIDPYKEFGSSYQLLNFLPLDFFPDLN ALVDTATALYEEELTGREHCSPHHTAIR QALVCWDELTKLIAWMSSNITSEQVRTI IVNHVNDTWGLKVRQSLWFHLSCLTFGQ HTVQEFLVSFGVWIRTPAPYRPPNAPIL STLPEHTVIRRRGGARASRSPRRRTPSP RRRRSQSPRRRRSQSPSANC |
|  | ZIKV E ENVELOPE ANTIGEN |  |
| 2 | Envelope domain 3 full length | HLKCRLKMDKLRLKGVSYSLCTAAFTFT KIPAETLHGTVTVEVQYAGTDGPCKVPA QMAVDMQTLTPVGRLITANPVITESTEN SKMMLELDPPFGDSYIVIGVGEKKITHH WHRSGSTIGKAFEATVRGAKRMAV |
| 3 | Envelope domain 3 G (EDIII) G loop-truncated | AFTFTKIPAETLHGTVTVELQYAGTDGP CKVPAQMAVDMQTLTPVGRLITANPVIT ESTENSKMMLELDPPFGDSYIVIG |
| 4 | Envelope domain 3, A-B loop | AFTFTKIPAETLHGTVTVELQYA |
| 5 | Envelope domain 3, CXCDDX loop (CD loop) | PCKVPAQMAVDMQTLTPVGRLITANPVI T |
| 6 | Envelope domain 3, DX-E loop | RLITANPVITESTENSKMMLELDP |
| 7 | Envelope domain 3, F-G loop | GDSYIVIGVGEKKITHHWHR |
| 8 | Envelope fusion loop | DRGWGNGCGLFGK |
| 9 | Envelope domain 2 (ED2) sequence A-E | TTTVSNMAEVRSYCYEASISDMASDSRC PTQGEAYLDKQSDTQYVCKRTLVDRGWG NGCGLFGKGSLVTCAKFACSKKMTGKSI QPENLEYR |
| 10 | Envelope domain 2 sequence B-D | EASISDMASDSRCPTQGEAYLDKQSDTQ YVCKRTLVDRGWGNGCGLFGKGSLVTCA KFACS |
| 11 | Envelope domain 1 glycan loop | MTGKSIQPENLEYRIMLSVHGSQHSGMI VNDTGHETDENRAKVEITPNSPRAEATL GGFGSLGLDCEPRTGLDFSDLYYLTM |

Table 2 depicts chimeric peptide sequences that comprise the Woodchuck Hepatitis core Antigen (WHcAg) sequence (SEQ ID NO: 1) together with each of SEQ ID NOs: 2-11 inserted (double underline) in the region of amino acids 77 and 82 of SEQ ID NO: 1. Amino acids in bold and italics indicate linker sequence.

TABLE 2

| SEQ ID NO | WHcAg (SEQ ID NO: 1) PLUS SEQ ID NO: | AMINO ACID SEQUENCE OF CHIMERIC PEPTIDE WITH ZIKV ENVELOPE (E) ANTIGEN |
|---|---|---|
| 12 | 2 | MDIDPYKEFGSSYQLLNFLPLDFFPDLNALVDTATALYEEELTGRE HCSPHHTAIRQALVCWDELTKLIAWMSSNI*GGGGT*<u>HLKCRLKMDKL RLKGVSYSLCTAAFTFTKIPAETLHGTVTVEVQYAGTDGPCKVPAQ MAVDMQTLTPVGRLITANPVITESTENSKMMLELDPPFGDSYIVIG VGEKKITHHWHRSGSTIGKAFEATVRGAKRMAV</u>*GGGG*TIIVNHVND TWGLKVRQSLWFHLSCLTFGQHTVQEFLVSFGVWIRTPAPYRPPNA PILSTLPEHTVIRRRGGARASRSPRRRTPSPRRRRSQSPRRRRSQS PSANC |
| 13 | 3 | MDIDPYKEFGSSYQLLNFLPLDFFPDLNALVDTATALYEEELTGRE HCSPHHTAIRQALVCWDELTKLIAWMSSNI<u>AFTFTKIPAETLHGTV TVELQYAGTDGPCKVPAQMAVDMQTLTPVGRLITANPVITESTENS KMMLELDPPFGDSYIVIG</u>TIIVNHVNDTWGLKVRQSLWFHLSCLTF GQHTVQEFLVSFGVWIRTPAPYRPPNAPILSTLPEHTVIRRRGGAR ASRSPRRRTPSPRRRRSQSPRRRRSQSPSANC |
| 14 | 4 | MDIDPYKEFGSSYQLLNFLPLDFFPDLNALVDTATALYEEELTGRE HCSPHHTAIRQALVCWDELTKLIAWMSSNI<u>AFTFTKIPAETLHGTV TVELQYA</u>TIIVNHVNDTWGLKVRQSLWFHLSCLTFGQHTVQEFLVS FGVWIRTPAPYRPPNAPILSTLPEHTVIRRRGGARASRSPRRRTPS PRRRRSQSPRRRRSQSPSANC |
| 15 | 5 | MDIDPYKEFGSSYQLLNFLPLDFFPDLNALVDTATALYEEELTGRE HCSPHHTAIRQALVCWDELTKLIAWMSSNI<u>PCKVPAQMAVDMQTLT PVGRLITANPVIT</u>TIIVNHVNDTWGLKVRQSLWFHLSCLTFGQHTV QEFLVSFGVWIRTPAPYRPPNAPILSTLPEHTVIRRRGGARASRSP RRRTPSPRRRRSQSPRRRRSQSPSANC |
| 16 | 6 | MDIDPYKEFGSSYQLLNFLPLDFFPDLNALVDTATALYEEELTGRE HCSPHHTAIRQALVCWDELTKLIAWMSSNI<u>RLITANPVITESTENS KMMLELDP</u>TIIVNHVNDTWGLKVRQSLWFHLSCLTFGQHTVQEFLV SFGVWIRTPAPYRPPNAPILSTLPEHTVIRRRGGARASRSPRRRTP SPRRRRSQSPRRRRSQSPSANC |
| 17 | 7 | MDIDPYKEFGSSYQLLNFLPLDFFPDLNALVDTATALYEEELTGRE HCSPHHTAIRQALVCWDELTKLIAWMSSNI<u>GDSYIVIGVGEKKITH HWHR</u>TIIVNHVNDTWGLKVRQSLWFHLSCLTFGQHTVQEFLVSFGV WIRTPAPYRPPNAPILSTLPEHTVIRRRGGARASRSPRRRTPSPRR RRSQSPRRRRSQSPSANC |
| 18 | 8 | MDIDPYKEFGSSYQLLNFLPLDFFPDLNALVDTATALYEEELTGRE HCSPHHTAIRQALVCWDELTKLIAWMSSNI*GGT*<u>DRGWGNGCGLFGK</u> *GG*TIIVNHVNDTWGLKVRQSLWFHLSCLTFGQHTVQEFLVSFGVWI RTPAPYRPPNAPILSTLPEHTVIRRRGGARASRSPRRRTPSPRRRR SQSPRRRRSQSPSANC |
| 19 | 9 | MDIDPYKEFGSSYQLLNFLPLDFFPDLNALVDTATALYEEELTGRE HCSPHHTAIRQALVCWDELTKLIAWMSSNI*GG*<u>TTTVSNMAEVRSYC YEASISDMASDSRCPTQGEAYLDKQSDTQYVCKRTLVDRGWGNGCG LFGKGSLVTCAKFACSKKMTGKSIQPENLEYR</u>*GG*TIIVNHVNDTWG LKVRQSLWFHLSCLTFGQHTVQEFLVSFGVWIRTPAPYRPPNAPIL STLPEHTVIRRRGGARASRSPRRRTPSPRRRRSQSPRRRRSQSPSA NC |
| 20 | 10 | MDIDPYKEFGSSYQLLNFLPLDFFPDLNALVDTATALYEEELTGRE HCSPHHTAIRQALVCWDELTKLIAWMSSNI*GG*<u>EASISDMASDSRCP TQGEAYLDKQSDTQYVCKRTLVDRGWGNGCGLFGKGSLVTCAKFAC S</u>*GG*TIIVNHVNDTWGLKVRQSLWFHLSCLTFGQHTVQEFLVSFGVW IRTPAPYRPPNAPILSTLPEHTVIRRRGGARASRSPRRRTPSPRRR RSQSPRRRRSQSPSANC |
| 21 | 11 | MDIDPYKEFGSSYQLLNFLPLDFFPDLNALVDTATALYEEELTGRE HCSPHHTAIRQALVCWDELTKLIAWMSSNI*GG*<u>MTGKSIQPENLEYR IMLSVHGSQHSGMIVNDTGHETDENRAKVEITPNSPRAEATLGGFG SLGLDCEPRTGLDFSDLYYLTM</u>*GG*TIIVNHVNDTWGLKVRQSLWFH LSCLTFGQHTVQEFLVSFGVWIRTPAPYRPPNAPILSTLPEHTVIR RRGGARASRSPRRRTPSPRRRRSQSPRRRRSQSPSANC |

Sequence ID NOs: 22-33 were obtained via structure analysis of NS1. The sequences were selected for their adaptability with the scaffolding system, i.e., the Woodchuck Hepatitis core Antigen (WHcAg) protein (Table 3). Structural information of the Zika Virus NS1 Protein was obtained from published scientific literature [22].

TABLE 3

| SEQ ID NO | ZIKV NS1 antigen | AMINO ACID SEQUENCE |
|---|---|---|
| 22 | NS1 Beta 1-2 | DVGCSVDFSKKETRCGT |
| 23 | NS1 Beta 3-4 | DRYKYHPDSPRRLAAAVKQAWEDGICGISSVSR |
| 24 | NS1 Alpha 2-Beta 5 | MENIMWRSVEGELNAILEENGVQLTVVVGSV |
| 25 | NS1 Beta 4-5-6 | CGISSVSRMENIMWRSVEGELNAILEENGVQLTVVVGSV KNPMWRGPQRLPVPVNELPHGWKAWGKSYFVRAAKTNNS FVVDGDTLKEC |
| 26 | NS1 Intertwined Loop-Beta 6 | KNPMWRGPQRLPVPVNELPHGWKAWGKSYFVRAAKTNNS FVVDG |
| 27 | NS1 Beta 7-8-9 | DTLKECPLKHRAWNSFLVEDHGFGVFHTSVWLKVREDYSLE |
| 28 | NS1 Beta 10-11-12-13 | CDPAVIGTAVKGKEAVHSDLGYWIESEKNDTWRLKRAHL IEMKTC |
| 29 | NS1 Beta 12-13 | GYWIESEKNDTWRLKRAHLI |
| 30 | NS1 Spaghetti Loop-Beta 14 | RAHLIEMKTCEWPKSHTLWTDGIEESDLIIPKSLAGPLS HHNTREGYRTQMKGPWHSEELEIR |
| 31 | NS1 Beta 14-15-16-17 | LEIRFEECPGTKVHVEETCGTRGPSLRSTTASGRVIEEW CCRECTMPPLSFRAK |
| 32 | NS1 Beta 15-16-17-18 | CPGTKVHVEETCGTRGPSLRSTTASGRVIEEWCCRECTM PPLSFRAKDGC |
| 33 | NS1 Beta 14-15-16-17-18-19-C terminus | MKGPWHSEELEIRFEECPGTKVHVEETCGTRGPSLRSTT ASGRVIEEWCCRECTMPPLSFRAKDGCWYGMEIRPRKEP ESNLVRSMVTA |

Table 4 depicts chimeric peptide sequences that comprise the Woodchuck Hepatitis core Antigen (WHcAg) sequence (Sequence ID NO: 1) together with each of Sequence ID NOs: 22-33 inserted (double underline) in the region of amino acids 77 and 82 of Sequence ID NO: 1. Amino acids in bold and italics indicate linker sequence.

TABLE 4

| SEQ ID NO | WHcAg (SEQ. ID NO: 1) PLUS SEQ. ID NO: | AMINO ACID SEQUENCE OF CHIMERIC PROTEIN WITH ZIKV NS1 ANTIGEN |
|---|---|---|
| 34 | 22 | MDIDPYKEFGSSYQLLNFLPLDFFPDLNALVDTATALYEEELTGREHCS PHHTAIRQALVCWDELTKLIAWMSSNI*GGGGT*DVGCSVDFSKKETRCGT *GGGG*TIIVNHVNDTWGLKVRQSLWFHLSCLTFGQHTVQEFLVSFGVWIR TPAPYRPPNAPILSTLPEHTVIRRGGARASRSPRRRTPSPRRRRSQSP RRRRSQSPSANC |
| 35 | 23 | MDIDPYKEFGSSYQLLNFLPLDFFPDLNALVDTATALYEEELTGREHCS PHHTAIRQALVCWDELTKLIAWMSSNI*GGGGT*DRYKYHPDSPRRLAAAV KQAWEDGICGISSVSR*GGGG*TIIVNHVNDTWGLKVRQSLWFHLSCLTFG QHTVQEFLVSFGVWIRTPAPYRPPNAPILSTLPEHTVIRRGGARASRS PRRRTPSPRRRRSQSPRRRRSQSPSANC |
| 36 | 24 | MDIDPYKEFGSSYQLLNFLPLDFFPDLNALVDTATALYEEELTGREHCS PHHTAIRQALVCWDELTKLIAWMSSNI*GGGGT*MENIMWRSVEGELNAIL EENGVQLTVVVGSV*GGGG*TIIVNHVNDTWGLKVRQSLWFHLSCLTFGQH TVQEFLVSFGVWIRTPAPYRPPNAPILSTLPEHTVIRRGGARASRSPR RRTPSPRRRRSQSPRRRRSQSPSANC |

TABLE 4-continued

| SEQ ID NO | WHcAg (SEQ. ID NO: 1) PLUS SEQ. ID NO: | AMINO ACID SEQUENCE OF CHIMERIC PROTEIN WITH ZIKV NS1 ANTIGEN |
|---|---|---|
| 37 | 25 | MDIDPYKEFGSSYQLLNFLPLDFFPDLNALVDTATALYEEELTGREHCSPHHTAIRQALVCWDELTKLIAWMSSNI*GGGGT*CGISSVSRMENIMWRSVEGELNAILEENGVQLTVVVGSVKNPMWRGPQRLPVPVNELPHGWKAWGKSYFVRAAKTNNSFVVDGDTLKEC*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 38 | 26 | MDIDPYKEFGSSYQLLNFLPLDFFPDLNALVDTATALYEEELTGREHCSPHHTAIRQALVCWDELTKLIAWMSSNI*GGGGT*KNPMWRGPQRLPVPVNELPHGWKAWGKSYFVRAAKTNNSFVVDG*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 39 | 27 | MDIDPYKEFGSSYQLLNFLPLDFFPDLNALVDTATALYEEELTGREHCSPHHTAIRQALVCWDELTKLIAWMSSNI*GGGGT*DTLKECPLKHRAWNSFLVEDHGFGVFHTSVWLKVREDYSLE*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 40 | 28 | MDIDPYKEFGSSYQLLNFLPLDFFPDLNALVDTATALYEEELTGREHCSPHHTAIRQALVCWDELTKLIAWMSSNI*GGGGT*CDPAVIGTAVKGKEAVHSDLGYWIESEKNDTWRLKRAHLIEMKTC*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 41 | 29 | MDIDPYKEFGSSYQLLNFLPLDFFPDLNALVDTATALYEEELTGREHCSPHHTAIRQALVCWDELTKLIAWMSSNI*GGGGT*GYWIESEKNDTWRLKRAHLI*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 42 | 30 | MDIDPYKEFGSSYQLLNFLPLDFFPDLNALVDTATALYEEELTGREHCSPHHTAIRQALVCWDELTKLIAWMSSNI*GGGGT*RAHLIEMKTCEWPKSHTLWTDGIEESDLIIPKSLAGPLSHHNTREGYRTQMKGPWHSEELEIR*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 43 | 31 | MDIDPYKEFGSSYQLLNFLPLDFFPDLNALVDTATALYEEELTGREHCSPHHTAIRQALVCWDELTKLIAWMSSNI*GGGGT*LEIRFEECPGTKVHVEETCGTRGPSLRSTTASGRVIEEWCCRECTMPPLSFRAK*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 44 | 32 | MDIDPYKEFGSSYQLLNFLPLDFFPDLNALVDTATALYEEELTGREHCSPHHTAIRQALVCWDELTKLIAWMSSNI*GGGGT*CPGTKVHVEETCGTRGPSLRSTTASGRVIEEWCCRECTMPPLSFRAKDGC*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |
| 45 | 33 | MDIDPYKEFGSSYQLLNFLPLDFFPDLNALVDTATALYEEELTGREHCSPHHTAIRQALVCWDELTKLIAWMSSNI*GGGGT*MKGPWHSEELEIRFEECPGTKVHVEETCGTRGPSLRSTTASGRVIEEWCCRECTMPPLSFRAKDGCWYGMEIRPRKEPESNLVRSMVTA*GGGG*TIIVNHVNDTWGLKVRQSLWFHLSCLTFGQHTVQEFLVSFGVWIRTPAPYRPPNAPILSTLPEHTVIRRRGGARASRSPRRRTPSPRRRRSQSPRRRRSQSPSANC |

Sequence ID NOs: 46-47 were obtained via structure analysis of prM/M protein. The sequences were selected for their adaptability with the scaffolding system, i.e., the Woodchuck Hepatitis core Antigen (WHcAg) protein (Table 5). Structural information of the Zika Virus prM/M protein was obtained from the literature [23]. prM sequence (Sequence ID NO: 46) has been mutagenized to prevent furin protease cleavage (R89G/R90G/R92G/R93G see underlined amino acids).

TABLE 5

| SEQ ID NO | ZIKV prM/M antigen | AMINO ACID SEQUENCE |
|---|---|---|
| 46 | prM Furin deficient | AEVTRRGSAYYMYLDRNDAGEAISFPTTLGMNKCYIQIMDLGHMC DATMSYECPMLDEGVEPDDVDCWCNTTSTWVVYGTCHHKKGEAGG SGGAVTLPSHSTRKLQTRSQTWLESREYTKHLIRVENWIFRNPGF ALAAAAIAWLLGSSTSQKVIYLVMILLIAPAYS |
| 47 | M full length | AVTLPSHSTRKLQTRSQTWLESREYTKHLIRVENWIFRNPGFALA AAAIAWLLGSSTSQKVIYLVMILLIAPAYS |

Table 6 depicts chimeric peptide sequences that comprise the Woodchuck Hepatitis core Antigen (WHcAg) sequence (Sequence ID NO: 1) together with each of Sequence ID NOs: 46-47 inserted (double underline) in the region of amino acids 77 and 82 of Sequence ID NO: 1. Amino acids in bold and italics indicate linker sequence.

TABLE 6

| SEQ ID NO | WHcAg (SEQ ID NO: 1) PLUS SEQ. ID NO: | AMINO ACID SEQUENCE OF CHIMERIC PROTEIN WITH ZIKV prM/M ANTIGEN |
|---|---|---|
| 48 | 46 | MDIDPYKEFGSSYQLLNFLPLDFFPDLNALVDTATALYEEELTGREHCS PHHTAIRQALVCWDELTKLIAWMSSNI*GGGGT*AEVTRRGSAYYMYLDRN DAGEAISFPTTLGMNKCYIQIMDLGHMCDATMSYECPMLDEGVEPDDVD CWCNTTSTWVVYGTCHHKKGEAGGSGGAVTLPSHSTRKLQTRSQTWLES REYTKHLIRVENWIFRNPGFALAAAAIAWLLGSSTSQKVIYLVMILLIA PAYS*GGGG*TIIVNHVNDTWGLKVRQSLWFHLSCLTFGQHTVQEFLVSFG VWIRTPAPYRPPNAPILSTLPEHTVIRRRGGARASRSPRRRTPSPRRRR SQSPRRRRSQSPSANC |
| 49 | 47 | MDIDPYKEFGSSYQLLNFLPLDFFPDLNALVDTATALYEEELTGREHCS PHHTAIRQALVCWDELTKLIAWMSSNI*GGGGT*AVTLPSHSTRKLQTRSQ TWLESREYTKHLIRVENWIFRNPGFALAAAAIAWLLGSSTSQKVIYLVM ILLIAPAYS*GGGG*TIIVNHVNDTWGLKVRQSLWFHLSCLTFGQHTVQEF LVSFGVWIRTPAPYRPPNAPILSTLPEHTVIRRRGGARASRSPRRRTPS PRRRRSQSPRRRRSQSPSANC |

Sequence ID NOs: 50-51 were obtained via structure analysis of Capsid C protein. The sequences were selected for their adaptability with the scaffolding system, i.e., the Woodchuck Hepatitis core Antigen (WHcAg) protein (Table 7). Structural information of the Zika Virus Capsid protein were obtained from the literature [24].

TABLE 7

| SEQ ID NO | ZIKV C CAPSID ANTIGEN | AMINO ACID SEQUENCE |
|---|---|---|
| 50 | C full length | MKNPKKKSGGFRIVNMLKRGVARVSPFGGLKRLPAGLLLGHGPIR MVLAILAFLRFTAIKPSLGLINRWGSVGKKEAMETIKKFKKDLAA MLRIINARKEKKRR |
| 51 | C alpha 2 | GHGPIRMVLAILAFLRFTAIKPSLG |

Table 8 depicts chimeric peptide sequences that comprise the Woodchuck Hepatitis core Antigen (WHcAg) sequence (Sequence ID NO: 1) together with each of Sequence ID NOs: 50-51 inserted (double underline) in the region of amino acids 77 and 82 of Sequence ID NO: 1. Amino acids in bold and italics indicate linker sequence.

TABLE 8

| SEQ ID NO | WHcAg (SEQ ID NO: 1) PLUS SEQ ID NO: | AMINO ACID SEQUENCE OF CHIMERIC PROTEIN WITH ZIKVC ANTIGEN |
|---|---|---|
| 52 | 50 | MDIDPYKEFGSSYQLLNFLPLDFFPDLNALVDTATALYEEELTGREHCSP HHTAIRQALVCWDELTKLIAWMSSNI*GGGGT*<u>MKNPKKKSGGFRIVNMLKR GVARVSPFGGLKRLPAGLLLGHGPIRMVLAILAFLRFTAIKPSLGLINRW GSVGKKEAMETIKKFKKDLAAMLRIINARKEKKRR</u>*GGGG*TIIVNHVNDTW GLKVRQSLWFHLSCLTFGQHTVQEFLVSFGVWIRTPAPYRPPNAPILSTL PEHTVIRRRGGARASRSPRRRTPSPRRRRSQSPRRRRSQSPSANC |
| 53 | 51 | MDIDPYKEFGSSYQLLNFLPLDFFPDLNALVDTATALYEEELTGREHCSP HHTAIRQALVCWDELTKLIAWMSSNI*GGGGT*<u>GHGPIRMVLAILAFLRFTA IKPSLG</u>*GGGG*TIIVNHVNDTWGLKVRQSLWFHLSCLTFGQHTVQEFLVSF GVWIRTPAPYRPPNAPILSTLPEHTVIRRRGGARASRSPRRRTPSPRRRR SQSPRRRRSQSPSANC |

Polynucleotides

The invention includes polynucleotides encoding the peptides as well as the chimeric peptides described herein. Exemplary sequences are set out in SEQ ID NOs: 22-53 (Tables 3-8, respectively). Because of the degeneracy of the genetic code, numerous polynucleotide sequences encode a given amino acid sequence, and all are contemplated as part of the invention. In some variations, codon selection is optimized for the type of host organism that will be used for expression.

TABLE 9

Polynucleotide sequences that encode the peptide and protein sequences of ZIKV E antigen shown in Table 1.

| SEQ ID NO | | POLYNUCLEOTIDE SEQUENCE |
|---|---|---|
| | VIRUS-LIKE PARTICLE PROTEIN | |
| 54 | Woodchuck Hepatitis Core Antigen (WHcAg) | ATGGACATCGACCCATACAAGGAATTCGGTTCTTCTTACCA ATTGTTGAACTTCTTGCCATTGGACTTCTTCCCAGACTTGA ACGCTTTGGTTGACACTGCTACTGCTTTGTACGAAGAAGAA TTGACTGGTAGAGAACACTGTTCTCCACACCACACTGCTAT CAGACAAGCTTTGGTTTGTTGGGACGAATTGACTAAGTTGA TCGCTTGGATGTCTTCTAACATCACTTCTGAACAAGTTAGA ACTATCATCGTTAACCACGTTAACGACACTTGGGGTTTGAA GGTTAGACAATCTTTGTGGTTCCACTTGTCTTGTTTGACTT TCGGTCAACACACTGTTCAAGAATTCTTGGTTTCTTTCGGT GTTTGGATCAGAACTCCAGCTCCATACAGACCACCAAACGC TCCAATCTTGTCTACTTTGCCAGAACACACTGTTATCAGAA GAAGAGGTGGTGCTAGAGCTTCTAGATCTCCAAGAAGAAGA ACTCCATCTCCAAGAAGAAGAAGATCTCAATCTCCAAGAAG AAGAAGATCTCAATCTCCATCTGCTAACTGT |
| | ZIKV E ENVELOPE ANTIGEN | |
| 55 | Envelope domain 3 full length | CACTTGAAGTGTAGATTGAAGATGGACAAGTTGAGATTGAA GGGTGTTTCTTACTCTTTGTGTACTGCTGCTTTCACTTTCA CTAAGATCCCAGCTGAAACTTTGCACGGTACTGTTACTGTT GAAGTTCAATACGCTGGTACTGACGGTCCATGTAAGGTTCC AGCTCAAATGGCTGTTGACATGCAAACTTTGACTCCAGTTG GTAGATTGATCACTGCTAACCCAGTTATCACTGAATCTACT GAAAACTCTAAGATGATGTTGGAATTGGACCCACCATTCGG |

TABLE 9-continued

Polynucleotide sequences that encode the peptide and
protein sequences of ZIKV E antigen shown in Table 1.

| SEQ ID NO | | POLYNUCLEOTIDE SEQUENCE |
|---|---|---|
| | | TGACTCTTACATCGTTATCGGTGTTGGTGAAAAGAAGATCA<br>CTCACCACTGGCACAGATCTGGTTCTACTATCGGTAAGGCT<br>TTCGAAGCTACTGTTAGAGGTGCTAAGAGAATGGCTGTT |
| 56 | Envelope domain 3 (EDIII) G loop-truncated | GCTTTCACTTTCACTAAGATCCCAGCTGAAACTTTGCACGG<br>TACTGTTACTGTTGAATTGCAATACGCTGGTACTGACGGTC<br>CATGTAAGGTTCCAGCTCAAATGGCTGTTGACATGCAAACT<br>TTGACTCCAGTTGGTAGATTGATCACTGCTAACCCAGTTAT<br>CACTGAATCTACTGAAAACTCTAAGATGATGTTGGAATTGG<br>ACCCACCATTCGGTGACTCTTACATCGTTATCGGT |
| 57 | Envelope domain 3, A-B loop | GCTTTCACTTTCACTAAGATCCCAGCTGAAACTTTGCACGG<br>TACTGTTACTGTTGAATTGCAATACGCT |
| 58 | Envelope domain 3, CXCDDX loop (CD loop) | CCATGTAAGGTTCCAGCTCAAATGGCTGTTGACATGCAAA<br>CTTTGACTCCAGTTGGTAGATTGATCACTGCTAACCCAGT<br>TATCACT |
| 59 | Envelope domain 3, DX-E loop | AGATTGATCACTGCTAACCCAGTTATCACTGAATCTACT<br>GAAAACTCTAAGATGATGTTGGAATTGGACCCA |
| 60 | Envelope domain 3, F-G loop | GGTGACTCTTACATCGTTATCGGTGTTGGTGAAAAGAAGAT<br>CACTCACCACTGGCACAGA |
| 61 | Envelope fusion loop | GACAGAGGTTGGGGTAACGGTTGTGGTTTGTTCGGTAAG |
| | VIRUS-LIKE PARTICLE PROTEIN | |
| 54 | Woodchuck Hepatitis Core Antigen (WHcAg) | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCACTTCTGAACAAGTTAGA<br>ACTATCATCGTTAACCACGTTAACGACACTTGGGGTTTGAA<br>GGTTAGACAATCTTTGTGGTTCCACTTGTCTTGTTTGACTT<br>TCGGTCAACACACTGTTCAAGAATTCTTGGTTTCTTTCGGT<br>GTTTGGATCAGAACTCCAGCTCCATACAGACCACCAAACGC<br>TCCAATCTTGTCTACTTTGCCAGAACACACTGTTATCAGAA<br>GAAGAGGTGGTGCTAGAGCTTCTAGATCTCCAAGAAGAAGA<br>ACTCCATCTCCAAGAAGAAGAAGATCTCAATCTCCAAGAAG<br>AAGAAGATCTCAATCTCCATCTGCTAACTGT |
| | ZIKV E ENVELOPE ANTIGEN | |
| 62 | Envelope domain 2 (ED2) sequence A-E | ACTACTACTGTTTCTAACATGGCTGAAGTTAGATCTT<br>ACTGTTACGAAGCTTCTATCTCTGACATGGCTTCTGA<br>CTCTAGATGTCCAACTCAAGGTGAAGCTTACTTGGAC<br>AAGCAATCTGACACTCAATACGTTTGTAAGAGAACTT<br>TGGTTGACAGAGGTTGGGGTAACGGTTGTGGTTTGTT<br>CGGTAAGGGTTCTTTGGTTACTTGTGCTAAGTTCGCT<br>TGTTCTAAGAAGATGACTGGTAAGTCTATCCAACCAG<br>AAAACTTGGAATACAGA |

TABLE 9-continued

Polynucleotide sequences that encode the peptide and protein sequences of ZIKV E antigen shown in Table 1.

| SEQ ID NO | | POLYNUCLEOTIDE SEQUENCE |
|---|---|---|
| 63 | Envelope domain 2 sequence B-D | GAAGCTTCTATCTCTGACATGGCTTCTGACTCTAGAT GTCCAACTCAAGGTGAAGCTTACTTGGACAAGCAATC TGACACTCAATACGTTTGTAAGAGAACTTTGGTTGAC AGAGGTTGGGGTAACGGTTGTGGTTTGTTCGGTAAGG GTTCTTTGGTTACTTGTGCTAAGTTCGCTTGTTCT |
| 64 | Envelope domain 1 glycan loop | ATGACTGGTAAGTCTATCCAACCAGAAAACTTGGAATACAG AATCATGTTGTCTGTTCACGGTTCTCAACACTCTGGTATGA TCGTTAACGACACTGGTCACGAAACTGACGAAAACAGAGCT AAGGTTGAAATCACTCCAAACTCTCCAAGAGCTGAAGCTAC TTTGGGTGGTTTCGGTTCTTTGGGTTTGGACTGTGAACCAA GAACTGGTTTGGACTTCTCTGACTTGTACTACTTGACTATG |

TABLE 10

Polynucleotide sequences encoding WHcAg-ZIKV chimeric proteins with ZIKV E antigen shown in Table 2.

| SEQ ID NO | WHcAg POLYNUCLEOTIDE SEQUENCE (SEQ ID NO: 54) PLUS SEQ ID NO: | POLYNUCLEOTIDE SEQUENCE OF CHIMERIC PROTEIN WITH ZIKV E ANTIGEN |
|---|---|---|
| 65 | 55 | ATGGACATCGACCCATACAAGGAATTCGGTTCTTCTTACCA ATTGTTGAACTTCTTGCCATTGGACTTCTTCCCAGACTTGA ACGCTTTGGTTGACACTGCTACTGCTTTGTACGAAGAAGAA TTGACTGGTAGAGAACACTGTTCTCCACACCACACTGCTAT CAGACAAGCTTTGGTTTGTTGGGACGAATTGACTAAGTTGA TCGCTTGGATGTCTTCTAACATCGGTGGTGGTGGTACTCAC TTGAAGTGTAGATTGAAGATGGACAAGTTGAGATTGAAGGG TGTTTCTTACTCTTTGTGTACTGCTGCTTTCACTTTCACTA AGATCCCAGCTGAAACTTTGCACGGTACTGTTACTGTTGAA GTTCAATACGCTGGTACTGACGGTCCATGTAAGGTTCCAGC TCAAATGGCTGTTGACATGCAAACTTTGACTCCAGTTGGTA GATTGATCACTGCTAACCCAGTTATCACTGAATCTACTGAA AACTCTAAGATGATGTTGGAATTGGACCCACCATTCGGTGA CTCTTACATCGTTATCGGTGTTGGTGAAAAGAAGATCACTC ACCACTGGCACAGATCTGGTTCTACTATCGGTAAGGCTTTC GAAGCTACTGTTAGAGGTGCTAAGAGAATGGCTGTTGGTGG TGGTGGTACTATCATCGTTAACCACGTTAACGACACTTGGG GTTTGAAGGTTAGACAATCTTTGTGGTTCCACTTGTCTTGT TTGACTTTCGGTCAACACACTGTTCAAGAATTCTTGGTTTC TTTCGGTGTTTGGATCAGAACTCCAGCTCCATACAGACCAC CAAACGCTCCAATCTTGTCTACTTTGCCAGAACACACTGTT ATCAGAAGAAGAGGTGGTGCTAGAGCTTCTAGATCTCCAAG AAGAAGAACTCCATCTCCAAGAAGAAGAAGATCTCAATCTC CAAGAAGAAGAAGATCTCAATCTCCATCTGCTAACTGT |
| 66 | 56 | ATGGACATCGACCCATACAAGGAATTCGGTTCTTCTTACCA ATTGTTGAACTTCTTGCCATTGGACTTCTTCCCAGACTTGA ACGCTTTGGTTGACACTGCTACTGCTTTGTACGAAGAAGAA TTGACTGGTAGAGAACACTGTTCTCCACACCACACTGCTAT CAGACAAGCTTTGGTTTGTTGGGACGAATTGACTAAGTTGA TCGCTTGGATGTCTTCTAACATCGCTTTCACTTTCACTAAG ATCCCAGCTGAAACTTTGCACGGTACTGTTACTGTTGAATT GCAATACGCTGGTACTGACGGTCCATGTAAGGTTCCAGCTC AAATGGCTGTTGACATGCAAACTTTGACTCCAGTTGGTAGA TTGATCACTGCTAACCCAGTTATCACTGAATCTACTGAAAA CTCTAAGATGATGTTGGAATTGGACCCACCATTCGGTGACT CTTACATCGTTATCGGTACTATCATCGTTAACCACGTTAAC GACACTTGGGGTTTGAAGGTTAGACAATCTTTGTGGTTCCA CTTGTCTTGTTTGACTTTCGGTCAACACACTGTTCAAGAAT TCTTGGTTTCTTTCGGTGTTTGGATCAGAACTCCAGCTCCA TACAGACCACCAAACGCTCCAATCTTGTCTACTTTGCCAGA ACACACTGTTATCAGAAGAAGAGGTGGTGCTAGAGCTTCTA GATCTCCAAGAAGAAGAACTCCATCTCCAAGAAGAAGAAGA TCTCAATCTCCAAGAAGAAGAAGATCTCAATCTCCATCTGC TAACTGT |

TABLE 10-continued

Polynucleotide sequences encoding WHcAg-ZIKV chimeric proteins with ZIKV E antigen shown in Table 2.

| SEQ ID NO | WHcAg POLYNUCLEOTIDE SEQUENCE (SEQ ID NO: 54) PLUS SEQ ID NO: | POLYNUCLEOTIDE SEQUENCE OF CHIMERIC PROTEIN WITH ZIKV E ANTIGEN |
|---|---|---|
| 67 | 57 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCGCTTTCACTTTCACTAAG<br>ATCCCAGCTGAAACTTTGCACGGTACTGTTACTGTTGAATT<br>GCAATACGCTACTATCATCGTTAACCACGTTAACGACACTT<br>GGGGTTTGAAGGTTAGACAATCTTTGTGGTTCCACTTGTCT<br>TGTTTGACTTTCGGTCAACACACTGTTCAAGAATTCTTGGT<br>TTCTTTCGGTGTTTGGATCAGAACTCCAGCTCCATACAGAC<br>CACCAAACGCTCCAATCTTGTCTACTTTGCCAGAACACACT<br>GTTATCAGAAGAAGAGGTGGTGCTAGAGCTTCTAGATCTCC<br>AAGAAGAAGAACTCCATCTCCAAGAAGAAGAAGATCTCAAT<br>CTCCAAGAAGAAGAAGATCTCAATCTCCATCTGCTAACTGT |
| 68 | 58 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCCCATGTAAGGTTCCAGCT<br>CAAATGGCTGTTGACATGCAAACTTTGACTCCAGTTGGTAG<br>ATTGATCACTGCTAACCCAGTTATCACTACTATCATCGTTA<br>ACCACGTTAACGACACTTGGGGTTTGAAGGTTAGACAATCT<br>TTGTGGTTCCACTTGTCTTGTTTGACTTTCGGTCAACACAC<br>TGTTCAAGAATTCTTGGTTTCTTTCGGTGTTTGGATCAGAA<br>CTCCAGCTCCATACAGACCACCAAACGCTCCAATCTTGTCT<br>ACTTTGCCAGAACACACTGTTATCAGAAGAAGAGGTGGTGC<br>TAGAGCTTCTAGATCTCCAAGAAGAAGAACTCCATCTCCAA<br>GAAGAAGAAGATCTCAATCTCCAAGAAGAAGAAGATCTCAA<br>TCTCCATCTGCTAACTGT |
| 69 | 59 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCAGATTGATCACTGCTAAC<br>CCAGTTATCACTGAATCTACTGAAAACTCTAAGATGATGTT<br>GGAATTGGACCCAACTATCATCGTTAACCACGTTAACGACA<br>CTTGGGGTTTGAAGGTTAGACAATCTTTGTGGTTCCACTTG<br>TCTTGTTTGACTTTCGGTCAACACACTGTTCAAGAATTCTT<br>GGTTTCTTTCGGTGTTTGGATCAGAACTCCAGCTCCATACA<br>GACCACCAAACGCTCCAATCTTGTCTACTTTGCCAGAACAC<br>ACTGTTATCAGAAGAAGAGGTGGTGCTAGAGCTTCTAGATC<br>TCCAAGAAGAAGAACTCCATCTCCAAGAAGAAGAAGATCTC<br>AATCTCCAAGAAGAAGAAGATCTCAATCTCCATCTGCTAAC<br>TGT |
| 70 | 60 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCGGTGACTCTTACATCGTT<br>ATCGGTGTTGGTGAAAAGAAGATCACTCACCACTGGCACAG<br>AACTATCATCGTTAACCACGTTAACGACACTTGGGGTTTGA<br>AGGTTAGACAATCTTTGTGGTTCCACTTGTCTTGTTTGACT<br>TTCGGTCAACACACTGTTCAAGAATTCTTGGTTTCTTTCGG<br>TGTTTGGATCAGAACTCCAGCTCCATACAGACCACCAAACG<br>CTCCAATCTTGTCTACTTTGCCAGAACACACTGTTATCAGA<br>AGAAGAGGTGGTGCTAGAGCTTCTAGATCTCCAAGAAGAAG<br>AACTCCATCTCCAAGAAGAAGAAGATCTCAATCTCCAAGAA<br>GAAGAAGATCTCAATCTCCATCTGCTAACTGT |
| 71 | 61 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA |

TABLE 10-continued

Polynucleotide sequences encoding WHcAg-ZIKV chimeric proteins with ZIKV E antigen shown in Table 2.

| SEQ ID NO | WHcAg POLYNUCLEOTIDE SEQUENCE (SEQ ID NO: 54) PLUS SEQ ID NO: | POLYNUCLEOTIDE SEQUENCE OF CHIMERIC PROTEIN WITH ZIKV E ANTIGEN |
|---|---|---|
| | | TCGCTTGGATGTCTTCTAACATCGGTGGTACTGACAGAGGT<br>TGGGGTAACGGTTGTGGTTTGTTCGGTAAGGGTGGTACTAT<br>CATCGTTAACCACGTTAACGACACTTGGGGTTTGAAGGTTA<br>GACAATCTTTGTGGTTCCACTTGTCTTGTTTGACTTTCGGT<br>CAACACACTGTTCAAGAATTCTTGGTTTCTTTCGGTGTTTG<br>GATCAGAACTCCAGCTCCATACAGACCACCAAACGCTCCAA<br>TCTTGTCTACTTTGCCAGAACACACTGTTATCAGAAGAAGA<br>GGTGGTGCTAGAGCTTCTAGATCTCCAAGAAGAAGAACTCC<br>ATCTCCAAGAAGAAGAAGATCTCAATCTCCAAGAAGAAGAA<br>GATCTCAATCTCCATCTGCTAACTGT |
| 72 | 62 | ATGGACATCGACCCATACAAGGAATTCGGTTCTTCTTACCAATTG<br>TTGAACTTCTTGCCATTGGACTTCTTCCCAGACTTGAACGCTTTG<br>GTTGACACTGCTACTGCTTTGTACGAAGAAGAATTGACTGGTAGA<br>GAACACTGTTCTCCACACCACACTGCTATCAGACAAGCTTTGGTT<br>TGTTGGGACGAATTGACTAAGTTGATCGCTTGGATGTCTTCTAAC<br>ATCGGTGGTACTACTACTGTTTCTAACATGGCTGAAGTTAGATCT<br>TACTGTTACGAAGCTTCTATCTCTGACATGGCTTCTGACTCTAGA<br>TGTCCAACTCAAGGTGAAGCTTACTTGGACAAGCAATCTGACACT<br>CAATACGTTTGTAAGAGAACTTTGGTTGACAGAGGTTGGGGTAAC<br>GGTTGTGGTTTGTTCGGTAAGGGTTCTTTGGTTACTTGTGCTAAG<br>TTCGCTTGTTCTAAGAAGATGACTGGTAAGTCTATCCAACCAGAA<br>AACTTGGAATACAGAGGTGGTACTATCATCGTTAACCACGTTAAC<br>GACACTTGGGGTTTGAAGGTTAGACAATCTTTGTGGTTCCACTTG<br>TCTTGTTTGACTTTCGGTCAACACACTGTTCAAGAATTCTTGGTT<br>TCTTTCGGTGTTTGGATCAGAACTCCAGCTCCATACAGACCACCA<br>AACGCTCCAATCTTGTCTACTTTGCCAGAACACACTGTTATCAGA<br>AGAAGAGGTGGTGCTAGAGCTTCTAGATCTCCAAGAAGAAGAACT<br>CCATCTCCAAGAAGAAGAAGATCTCAATCTCCAAGAAGAAGAAGA<br>TCTCAATCTCCATCTGCTAACTGT |
| 73 | 63 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCGGTGGTGAAGCTTCTATC<br>TCTGACATGGCTTCTGACTCTAGATGTCCAACTCAAGGTGA<br>AGCTTACTTGGACAAGCAATCTGACACTCAATACGTTTGTA<br>AGAGAACTTTGGTTGACAGAGGTTGGGGTAACGGTTGTGGT<br>TTGTTCGGTAAGGGTTCTTTGGTTACTTGTGCTAAGTTCGC<br>TTGTTCTGGTGGTACTATCATCGTTAACCACGTTAACGACA<br>CTTGGGGTTTGAAGGTTAGACAATCTTTGTGGTTCCACTTG<br>TCTTGTTTGACTTTCGGTCAACACACTGTTCAAGAATTCTT<br>GGTTTCTTTCGGTGTTTGGATCAGAACTCCAGCTCCATACA<br>GACCACCAAACGCTCCAATCTTGTCTACTTTGCCAGAACAC<br>ACTGTTATCAGAAGAAGAGGTGGTGCTAGAGCTTCTAGATC<br>TCCAAGAAGAAGAACTCCATCTCCAAGAAGAAGAAGATCTC<br>AATCTCCAAGAAGAAGAAGATCTCAATCTCCATCTGCTAAC<br>TGT |
| 74 | 64 | ATGGACATCGACCCATACAAGGAATTCGGTTCTTCTTACCA<br>ATTGTTGAACTTCTTGCCATTGGACTTCTTCCCAGACTTGA<br>ACGCTTTGGTTGACACTGCTACTGCTTTGTACGAAGAAGAA<br>TTGACTGGTAGAGAACACTGTTCTCCACACCACACTGCTAT<br>CAGACAAGCTTTGGTTTGTTGGGACGAATTGACTAAGTTGA<br>TCGCTTGGATGTCTTCTAACATCGGTGGTATGACTGGTAAG<br>TCTATCCAACCAGAAAACTTGGAATACAGAATCATGTTGTC<br>TGTTCACGGTTCTCAACACTCTGGTATGATCGTTAACGACA<br>CTGGTCACGAAACTGACGAAAACAGAGCTAAGGTTGAAATC<br>ACTCCAAACTCTCCAAGAGCTGAAGCTACTTTGGGTGGTTT<br>CGGTTCTTTGGGTTTGGACTGTGAACCAAGAACTGGTTTGG<br>ACTTCTCTGACTTGTACTACTTGACTATGGGTGGTACTATC<br>ATCGTTAACCACGTTAACGACACTTGGGGTTTGAAGGTTAG<br>ACAATCTTTGTGGTTCCACTTGTCTTGTTTGACTTTCGGTC<br>AACACACTGTTCAAGAATTCTTGGTTTCTTTCGGTGTTTGG<br>ATCAGAACTCCAGCTCCATACAGACCACCAAACGCTCCAAT<br>CTTGTCTACTTTGCCAGAACACACTGTTATCAGAAGAAGAG<br>GTGGTGCTAGAGCTTCTAGATCTCCAAGAAGAAGAACTCCA |

TABLE 10-continued

Polynucleotide sequences encoding WHcAg-ZIKV chimeric proteins with ZIKV E antigen shown in Table 2.

| SEQ ID NO | WHcAg POLYNUCLEOTIDE SEQUENCE (SEQ ID NO: 54) PLUS SEQ ID NO: | POLYNUCLEOTIDE SEQUENCE OF CHIMERIC PROTEIN WITH ZIKV E ANTIGEN |
|---|---|---|
| | | TCTCCAAGAAGAAGAAGATCTCAATCTCCAAGAAGAAGAAG ATCTCAATCTCCATCTGCTAACTGT |

TABLE 11

Polynucleotide sequences that encode the peptide and protein sequences of ZIKV NS1 antigen shown in Table 3.

| SEQ ID NO | ZIKV NS1 ANTIGEN | POLYNUCLEOTIDE SEQUENCE OF ZIKV NS1 ANTIGEN |
|---|---|---|
| 75 | NS1 Beta 1-2 | GACGTTGGTTGTTCTGTTGACTTCTCTAAGAAGGAAACTAGATGTGGTACT |
| 76 | NS1 Beta 3-4 | GACAGATACAAGTACCACCCAGACTCTCCAAGAAGATTGGCTGCTGCTGT TAAGCAAGCTTGGGAAGACGGTATCTGTGGTATCTCTTCTGTTTCTAGA |
| 77 | NS1 Alpha 2-Beta 5 | ATGGAAAACATCATGTGGAGATCTGTTAAGGTGAATTGAACGCTATCTT GGAAGAAAACGGTGTTCAATTGACTGTTGTTGTTGGTTCTGTT |
| 78 | NS1 Beta 4-5-6 | TGTGGTATCTCTTCTGTTTCTAGAATGGAAAACATCATGTGGAGATCTGT TGAAGGTGAATTGAACGCTATCTTGGAAGAAAACGGTGTTCAATTGACTG TTGTTGTTGGTTCTGTTAAGAACCCAATGTGGAGAGGTCCACAAAGATTG CCAGTTCCAGTTAACGAATTGCCACACGGTTGGAAGGCTTGGGGTAAGTC TTACTTCGTTAGAGCTGCTAAGACTAACAACTCTTTCGTTGTTGACGGTG ACACTTTGAAGGAATGTGTT |
| 79 | NS1 Inter. Loop-Beta 6 | AAGAACCCAATGTGGAGAGGTCCACAAAGATTGCCAGTTCCAGTTAACGA ATTGCCACACGGTTGGAAGGCTTGGGGTAAGTCTTACTTCGTTAGAGCTG CTAAGACTAACAACTCTTTCGTTGTTGACGGT |
| 80 | NS1 Beta 7-8-9 | GACACTTTGAAGGAATGTCCATTGAAGCACAGAGCTTGGAACTCTTTCTT GGTTGAAGACCACGGTTTCGGTGTTTTCCACACTTCTGTTTGGTTGAAGG TTAGAGAAGACTACTCTTTGGAA |
| 81 | NS1 Beta 10-11-12-13 | TGTGACCCAGCTGTTATCGGTACTGCTGTTAAGGGTAAGGAAGCTGTTCA CTCTGACTTGGGTTACTGGATCGAATCTGAAAAGAACGACACTTGGAGAT TGAAGAGAGCTCACTTGATCGAAATGAAGACTTGT |
| 82 | NS1 Beta 12-13 | GGTTACTGGATCGAATCTGAAAAGAACGACACTTGGAGATTGAAGAGAGC TCACTTGATC |
| 83 | NS1 Spaghetti Loop-Beta 14 | AGAGCTCACTTGATCGAAATGAAGACTTGTGAATGGCCAAAGTCTCACAC TTTGTGGACTGACGGTATCGAAGAATCTGACTTGATCATCCCAAAGTCTT TGGCTGGTCCATTGTCTCACCACAACACTAGAGAAGGTTACAGAACTCAA ATGAAGGGTCCATGGCACTCTGAAGAATTGGAAATCAGA |
| 84 | NS1 Beta 14-15-16-17 | TTGGAAATCAGATTCGAAGAATGTCCAGGTACTAAGGTTCACGTTGAAGA AACTTGTGGTACTAGAGGTCCATCTTTGAGATCTACTACTGCTTCTGGTA GAGTTATCGAAGAATGGTGTTGTAGAGAATGTACTATGCCACCATTGTCT TTCAGAGCTAAG |
| 85 | NS1 Beta 15-16-17-18 | TGTCCAGGTACTAAGGTTCACGTTGAAGAAACTTGTGGTACTAGAGGTCC ATCTTTGAGATCTACTACTGCTTCTGGTAGAGTTATCGAAGAATGGTGTT GTAGAGAATGTACTATGCCACCATTGTCTTTCAGAGCTAAGGACGGTTGT |
| 86 | NS1 Beta 14-15-16-17-18-19-C-term. | ATGAAGGGTCCATGGCACTCTGAAGAATTGGAAATCAGATTCGAAGAATG TCCAGGTACTAAGGTTCACGTTGAAGAAACTTGTGGTACTAGAGGTCCAT CTTTGAGATCTACTACTGCTTCTGGTAGAGTTATCGAAGAATGGTGTTGT AGAGAATGTACTATGCCACCATTGTCTTTCAGAGCTAAGGACGGTTGTTG GTACGGTATGGAAATCAGACCAAGAAAGGAACCAGAATCTAACTTGGTTA GATCTATGGTTACTGCT |

TABLE 12

Polynucleotide sequences encoding WHcAg-ZIKV chimeric proteins with ZIKV NS1 antigen shown in Table 4.

| SEQ ID NO | WHcAg (SEQ ID NO: 54) PLUS SEQ ID NO: | POLYNUCLEOTIDE SEQUENCE OF CHIMERIC PROTEIN WITH ZIKV NS1 ANTIGEN |
|---|---|---|
| 87 | 75 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTGACGTTGGTTGT<br>TCTGTTGACTTCTCTAAGAAGGAAACTAGATGTGGTACTGGTGGTGGTGGT<br>ACTATCATCGTTAACCACGTTAACGACACTTGGGGTTTGAAGGTTAGACAA<br>TCTTTGTGGTTCCACTTGTCTTGTTTGACTTTCGGTCAACACACTGTTCAA<br>GAATTCTTGGTTTCTTTCGGTGTTTGGATCAGAACTCCAGCTCCATACAGA<br>CCACCAAACGCTCCAATCTTGTCTACTTTGCCAGAACACACTGTTATCAGA<br>AGAAGAGGTGGTGCTAGAGCTTCTAGATCTCCAAGAAGAAGAACTCCATCT<br>CCAAGAAGAAGAAGATCTCAATCTCCAAGAAGAAGAAGATCTCAATCTCCA<br>TCTGCTAACTGT |
| 88 | 76 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTGACAGATACAAG<br>TACCACCCAGACTCTCCAAGAAGATTGGCTGCTGCTGTTAAGCAAGCTTGG<br>GAAGACGGTATCTGTGGTATCTCTTCTGTTTCTAGAGGTGGTGGTGGTACT<br>ATCATCGTTAACCACGTTAACGACACTTGGGGTTTGAAGGTTAGACAATCT<br>TTGTGGTTCCACTTGTCTTGTTTGACTTTCGGTCAACACACTGTTCAAGAA<br>TTCTTGGTTTCTTTCGGTGTTTGGATCAGAACTCCAGCTCCATACAGACCA<br>CCAAACGCTCCAATCTTGTCTACTTTGCCAGAACACACTGTTATCAGAAGA<br>AGAGGTGGTGCTAGAGCTTCTAGATCTCCAAGAAGAAGAACTCCATCTCCA<br>AGAAGAAGAAGATCTCAATCTCCAAGAAGAAGAAGATCTCAATCTCCATCT<br>GCTAACTGT |
| 89 | 77 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTATGGAAAACATC<br>ATGTGGAGATCTGTTGAAGGTGAATTGAACGCTATCTTGGAAGAAAACGGT<br>GTTCAATTGACTGTTGTTGTTGGTTCTGTTGGTGGTGGTGGTACTATCATC<br>GTTAACCACGTTAACGACACTTGGGGTTTGAAGGTTAGACAATCTTTGTGG<br>TTCCACTTGTCTTGTTTGACTTTCGGTCAACACACTGTTCAAGAATTCTTG<br>GTTTCTTTCGGTGTTTGGATCAGAACTCCAGCTCCATACAGACCACCAAAC<br>GCTCCAATCTTGTCTACTTTGCCAGAACACACTGTTATCAGAAGAAGAGGT<br>GGTGCTAGAGCTTCTAGATCTCCAAGAAGAAGAACTCCATCTCCAAGAAGA<br>AGAAGATCTCAATCTCCAAGAAGAAGAAGATCTCAATCTCCATCTGCTAAC<br>TGT |
| 90 | 78 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTTGTGGTATCTCT<br>TCTGTTTCTAGAATGGAAAACATCATGTGGAGATCTGTTGAAGGTGAATTG<br>AACGCTATCTTGGAAGAAAACGGTGTTCAATTGACTGTTGTTGTTGGTTCT<br>GTTAAGAACCCAATGTGGAGAGGTCCACAAAGATTGCCAGTTCCAGTTAAC<br>GAATTGCCACACGGTTGGAAGGCTTGGGGTAAGTCTTACTTCGTTAGAGCT<br>GCTAAGACTAACAACTCTTTCGTTGTTGACGGTGACACTTTGAAGGAATGT<br>GGTGGTGGTGGTACTATCATCGTTAACCACGTTAACGACACTTGGGGTTTG<br>AAGGTTAGACAATCTTTGTGGTTCCACTTGTCTTGTTTGACTTTCGGTCAA<br>CACACTGTTCAAGAATTCTTGGTTTCTTTCGGTGTTTGGATCAGAACTCCA<br>GCTCCATACAGACCACCAAACGCTCCAATCTTGTCTACTTTGCCAGAACAC<br>ACTGTTATCAGAAGAAGAGGTGGTGCTAGAGCTTCTAGATCTCCAAGAAGA<br>AGAACTCCATCTCCAAGAAGAAGAAGATCTCAATCTCCAAGAAGAAGAAGA<br>TCTCAATCTCCATCTGCTAACTGT |
| 91 | 79 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTAAGAACCCAATG<br>TGGAGAGGTCCACAAAGATTGCCAGTTCCAGTTAACGAATTGCCACACGGT<br>TGGAAGGCTTGGGGTAAGTCTTACTTCGTTAGAGCTGCTAAGACTAACAAC<br>TCTTTCGTTGTTGACGGTGGTGGTGGTACTATCATCGTTAACCACGTT<br>AACGACACTTGGGGTTTGAAGGTTAGACAATCTTTGTGGTTCCACTTGTCT |

TABLE 12-continued

Polynucleotide sequences encoding WHcAg-ZIKV chimeric proteins with ZIKV NS1 antigen shown in Table 4.

| SEQ ID NO | WHcAg (SEQ ID NO: 54) PLUS SEQ ID NO: | POLYNUCLEOTIDE SEQUENCE OF CHIMERIC PROTEIN WITH ZIKV NS1 ANTIGEN |
|---|---|---|
| | | TGTTTGACTTTCGGTCAACACACTGTTCAAGAATTCTTGGTTTCTTTCGGT<br>GTTTGGATCAGAACTCCAGCTCCATACAGACCACCAAACGCTCCAATCTTG<br>TCTACTTTGCCAGAACACACTGTTATCAGAAGAAGAGGTGGTGCTAGAGCT<br>TCTAGATCTCCAAGAAGAAGAACTCCATCTCCAAGAAGAAGAAGATCTCAA<br>TCTCCAAGAAGAAGAAGATCTCAATCTCCATCTGCTAACTGT |
| 92 | 80 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTGACACTTTGAAG<br>GAATGTCCATTGAAGCACAGAGCTTGGAACTCTTTCTTGGTTGAAGACCAC<br>GGTTTCGGTGTTTTCCACACTTCTGTTTGGTTGAAGGTTAGAGAAGACTAC<br>TCTTTGGAAGGTGGTGGTGGTACTATCATCGTTAACCACGTTAACGACACT<br>TGGGGTTTGAAGGTTAGACAATCTTTGTGGTTCCACTTGTCTTGTTTGACT<br>TTCGGTCAACACACTGTTCAAGAATTCTTGGTTTCTTTCGGTGTTTGGATC<br>AGAACTCCAGCTCCATACAGACCACCAAACGCTCCAATCTTGTCTACTTTG<br>CCAGAACACACTGTTATCAGAAGAAGAGGTGGTGCTAGAGCTTCTAGATCT<br>CCAAGAAGAAGAACTCCATCTCCAAGAAGAAGAAGATCTCAATCTCCAAGA<br>AGAAGAAGATCTCAATCTCCATCTGCTAACTGT |
| 93 | 81 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTTGTGACCCAGCT<br>GTTATCGGTACTGCTGTTAAGGGTAAGGAAGCTGTTCACTCTGACTGGGT<br>TACTGGATCGAATCTGAAAAGAACGACACTTGGAGATTGAAGAGAGCTCAC<br>TTGATCGAAATGAAGACTTGTGGTGGTGGTGGTACTATCATCGTTAACCAC<br>GTTAACGACACTTGGGGTTTGAAGGTTAGACAATCTTTGTGGTTCCACTTG<br>TCTTGTTTGACTTTCGGTCAACACACTGTTCAAGAATTCTTGGTTTCTTTC<br>GGTGTTTGGATCAGAACTCCAGCTCCATACAGACCACCAAACGCTCCAATC<br>TTGTCTACTTTGCCAGAACACACTGTTATCAGAAGAAGAGGTGGTGCTAGA<br>GCTTCTAGATCTCCAAGAAGAAGAACTCCATCTCCAAGAAGAAGAAGATCT<br>CAATCTCCAAGAAGAAGAAGATCTCAATCTCCATCTGCTAACTGT |
| 94 | 82 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTGGTTACTGGATC<br>GAATCTGAAAAGAACGACACTTGGAGATTGAAGAGAGCTCACTTGATCGGT<br>GGTGGTGGTACTATCATCGTTAACCACGTTAACGACACTTGGGGTTTGAAG<br>GTTAGACAATCTTTGTGGTTCCACTTGTCTTGTTTGACTTTCGGTCAACAC<br>ACTGTTCAAGAATTCTTGGTTTCTTTCGGTGTTTGGATCAGAACTCCAGCT<br>CCATACAGACCACCAAACGCTCCAATCTTGTCTACTTTGCCAGAACACACT<br>GTTATCAGAAGAAGAGGTGGTGCTAGAGCTTCTAGATCTCCAAGAAGAAGA<br>ACTCCATCTCCAAGAAGAAGAAGATCTCAATCTCCAAGAAGAAGAAGATCT<br>CAATCTCCATCTGCTAACTGT |
| 95 | 83 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTAGAGCTCACTTG<br>ATCGAAATGAAGCTTGTGAATGGCCAAAGTCTCACACTTTGTGGACTGAC<br>GGTATCGAAGAATCTGACTTGATCATCCCAAAGTCTTTGGCTGGTCCATTG<br>TCTCACCACAACACTAGAGAAGGTTACAGAACTCAAATGAAGGGTCCATGG<br>CACTCTGAAGAATTGGAAATCAGAGGTGGTGGTGGTACTATCATCGTTAAC<br>CACGTTAACGACACTTGGGGTTTGAAGGTTAGACAATCTTTGTGGTTCCAC<br>TTGTCTTGTTTGACTTTCGGTCAACACACTGTTCAAGAATTCTTGGTTTCT<br>TTCGGTGTTTGGATCAGAACTCCAGCTCCATACAGACCACCAAACGCTCCA<br>ATCTTGTCTACTTTGCCAGAACACACTGTTATCAGAAGAAGAGGTGGTGCT<br>AGAGCTTCTAGATCTCCAAGAAGAAGAACTCCATCTCCAAGAAGAAGAAGA<br>TCTCAATCTCCAAGAAGAAGAAGATCTCAATCTCCATCTGCTAACTGT |
| 96 | 84 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTGGTACTTTGGAAATCAGA |

TABLE 12-continued

Polynucleotide sequences encoding WHcAg-ZIKV chimeric proteins with ZIKV NS1 antigen shown in Table 4.

| SEQ ID NO | WHcAg (SEQ ID NO: 54) PLUS SEQ ID NO: | POLYNUCLEOTIDE SEQUENCE OF CHIMERIC PROTEIN WITH ZIKV NS1 ANTIGEN |
|---|---|---|
| | | TTCGAAGAATGTCCAGGTACTAAGGTTCACGTTGAAGAAACTTGTGGTACT<br>AGAGGTCCATCTTTGAGATCTACTACTGCTTCTGGTAGAGTTATCGAAGAA<br>TGGTGTTGTAGAGAATGTACTATGCCACCATTGTCTTTCAGAGCTAAGGGT<br>GGTGGTGGTACTATCATCGTTAACCACGTTAACGACACTTGGGGTTTGAAG<br>GTTAGACAATCTTTGTGGTTCCACTTGTCTTGTTTGACTTTCGGTCAACAC<br>ACTGTTCAAGAATTCTTGGTTTCTTTCGGTGTTTGGATCAGAACTCCAGCT<br>CCATACAGACCACCAAACGCTCCAATCTTGTCTACTTTGCCAGAACACACT<br>GTTATCAGAAGAAGAGGTGGTGCTAGAGCTTCTAGATCTCCAAGAAGAAGA<br>ACTCCATCTCCAAGAAGAAGAAGATCTCAATCTCCAAGAAGAAGAAGATCT<br>CAATCTCCATCTGCTAACTGT |
| 97 | 85 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTACTTGTCCAGGTACT<br>AAGGTTCACGTTGAAGAAACTTGTGGTACTAGAGGTCCATCTTTGAGATCT<br>ACTACTGCTTCTGGTAGAGTTATCGAAGAATGGTGTTGTAGAGAATGTACT<br>ATGCCACCATTGTCTTTCAGAGCTAAGGACGGTTGTGGTGGTGGTGGTACT<br>ATCATCGTTAACCACGTTAACGACACTTGGGGTTTGAAGGTTAGACAATCT<br>TTGTGGTTCCACTTGTCTTGTTTGACTTTCGGTCAACACACTGTTCAAGAA<br>TTCTTGGTTTCTTTCGGTGTTTGGATCAGAACTCCAGCTCCATACAGACCA<br>CCAAACGCTCCAATCTTGTCTACTTTGCCAGAACACACTGTTATCAGAAGA<br>AGAGGTGGTGCTAGAGCTTCTAGATCTCCAAGAAGAAGAACTCCATCTCCA<br>AGAAGAAGAAGATCTCAATCTCCAAGAAGAAGAAGATCTCAATCTCCATCT<br>GCTAACTGT |
| 98 | 86 | ATGGACATCGACCCATACAAGGAATTCGGTTCTTCTTACCAATTGTTGAAC<br>TTCTTGCCATTGGACTTCTTCCCAGACTTGAACGCTTTGGTTGACACTGCT<br>ACTGCTTTGTACGAAGAAGAATTGACTGGTAGAGAACACTGTTCTCCACAC<br>CACACTGCTATCAGACAAGCTTTGGTTTGTTGGGACGAATTGACTAAGTTG<br>ATCGCTTGGATGTCTTCTAACATCGGTGGTGGTACTATGAAGGGTCCA<br>TGGCACTCTGAAGAATTGGAAATCAGATTCGAAGAATGTCCAGGTACTAAG<br>GTTCACGTTGAAGAAACTTGTGGTACTAGAGGTCCATCTTTGAGATCTACT<br>ACTGCTTCTGGTAGAGTTATCGAAGAATGGTGTTGTAGAGAATGTACTATG<br>CCACCATTGTCTTTCAGAGCTAAGGACGGTTGTTGGTACGGTATGGAAATC<br>AGACCAAGAAAGGAACCAGAATCTAACTTGGTTAGATCTATGGTTACTGCT<br>GGTGGTGGTGGTACTATCATCGTTAACCACGTTAACGACACTTGGGGTTTG<br>AAGGTTAGACAATCTTTGTGGTTCCACTTGTCTTGTTTGACTTTCGGTCAA<br>CACACTGTTCAAGAATTCTTGGTTTCTTTCGGTGTTTGGATCAGAACTCCA<br>GCTCCATACAGACCACCAAACGCTCCAATCTTGTCTACTTTGCCAGAACAC<br>ACTGTTATCAGAAGAAGAGGTGGTGCTAGAGCTTCTAGATCTCCAAGAAGA<br>AGAACTCCATCTCCAAGAAGAAGAAGATCTCAATCTCCAAGAAGAAGAAGA<br>TCTCAATCTCCATCTGCTAACTGT |

TABLE 13

Polynucleotide sequences that encode the peptide and protein sequences of ZIKV prM/M antigen shown in Table 5.

| SEQ ID NO | ZIKV prM/M ANTIGEN | POLYNUCLEOTIDE SEQUENCE OF ZIKV prM/M ANTIGEN |
|---|---|---|
| 99 | prM Furin deficient | GCTGAAGTTACTAGAAGAGGTTCTGCTTACTACATGTACTTGGACAGAAACG<br>ACGCTGGTGAAGCTATCTCTTTCCCAACTACTTTGGGTATGAACAAGTGTTA<br>CATCCAAATCATGGACTTGGGTCACATGTGTGACGCTACTATGTCTTACGAA<br>TGTCCAATGTTGGACGAAGGTGTTGAACCAGACGACGTTGACTGTTGGTGTA<br>ACACTACTTCTACTTGGGTTGTTTACGGTACTTGTCACCACAAGAAGGGTGA<br>AGCTGGTGGTTCTGGTGGTGCTGTTACTTTGCCATCTCACTCTACTAGAAAG<br>TTGCAAACTAGATCTCAAACTTGGTTGGAATCTAGAGAATACACTAAGCACT<br>TGATCAGAGTTGAAAACTGGATCTTCAGAAACCCAGGTTTCGCTTTGGCTGC<br>TGCTGCTATCGCTTGGTTGTTGGGTTCTTCTACTTCTCAAAAGGTTATCTAC<br>TTGGTTATGATCTTGTTGATCGCTCCAGCTTACTCT |

TABLE 13-continued

Polynucleotide sequences that encode the peptide and protein sequences of ZIKV prM/M antigen shown in Table 5.

| SEQ ID NO | ZIKV prM/M ANTIGEN | POLYNUCLEOTIDE SEQUENCE OF ZIKV prM/M ANTIGEN |
|---|---|---|
| 100 | M full length | GCTGTTACTTTGCCATCTCACTCTACTAGAAAGTTGCAAACTAGATCTCAAA CTTGGTTGGAATCTAGAGAATACACTAAGCACTTGATCAGAGTTGAAAACTG GATCTTCAGAAACCCAGGTTTCGCTTTGGCTGCTGCTGCTATCGCTTGGTTG TTGGGTTCTTCTACTTCTCAAAAGGTTATCTACTTGGTTATGATCTTGTTGA TCGCTCCAGCTTACTCT |

TABLE 14

Polynucleotide sequences encoding WHcAg-ZIKV chimeric proteins with ZIKV prM/M antigen shown in Table 6.

| SEQ ID NO | WHcAg (SEQ ID NO: 62) PLUS SEQ ID NO: | POLYNUCLEOTIDE SEQUENCE OF CHIMERIC PROTEIN WITH ZIKV prM/M ANTIGEN |
|---|---|---|
| 101 | 99 | ATGGACATCGACCCATACAAGGAATTCGGTTCTTCTTACCAATTGTTGAAC TTCTTGCCATTGGACTTCTTCCCAGACTTGAACGCTTTGGTTGACACTGCT ACTGCTTTGTACGAAGAAGAATTGACTGGTAGAGAACACTGTTCTCCACAC CACACTGCTATCAGACAAGCTTTGGTTTGTTGGGACGAATTGACTAAGTTG ATCGCTTGGATGTCTTCTAACATCGGTGGTGGTGGTACTGCTGAAGTTACT AGAAGAGGTTCTGCTTACTACATGTACTTGGACAGAAACGACGCTGGTGAA GCTATCTCTTTCCCAACTACTTTGGGTATGAACAAGTGTTACATCCAAATC ATGGACTTGGGTCACATGTGTGACGCTACTATGTCTTACGAATGTCCAATG TTGGACGAAGGTGTTGAACCAGACGACGTTGACTGTTGGTGTAACACTACT TCTACTTGGGTTGTTTACGGTACTTGTCACCACAAGAAGGGTGAAGCTGGT GGTTCTGGTGGTGCTGTTACTTTGCCATCTCACTCTACTAGAAAGTTGCAA ACTAGATCTCAAACTTGGTTGGAATCTAGAGAATACACTAAGCACTTGATC AGAGTTGAAAACTGGATCTTCAGAAACCCAGGTTTCGCTTTGGCTGCTGCT GCTATCGCTTGGTTGTTGGGTTCTTCTACTTCTCAAAAGGTTATCTACTTG GTTATGATCTTGTTGATCGCTCCAGCTTACTCTGGTGGTGGTGGTACTATC ATCGTTAACCACGTTAACGACACTTGGGGTTTGAAGGTTAGACAATCTTTG TGGTTCCACTTGTCTTGTTTGACTTTCGGTCAACACACTGTTCAAGAATTC TTGGTTTCTTTCGGTGTTTGGATCAGAACTCCAGCTCCATACAGACCACCA AACGCTCCAATCTTGTCTACTTTGCCAGAACACACTGTTATCAGAAGAAGA GGTGGTGCTAGAGCTTCTAGATCTCCAAGAAGAAGAACTCCATCTCCAAGA AGAAGAAGATCTCAATCTCCAAGAAGAAGAAGATCTCAATCTCCATCTGCT AACTGT |
| 102 | 100 | ATGGACATCGACCCATACAAGGAATTCGGTTCTTCTTACCAATTGTTGAAC TTCTTGCCATTGGACTTCTTCCCAGACTTGAACGCTTTGGTTGACACTGCT ACTGCTTTGTACGAAGAAGAATTGACTGGTAGAGAACACTGTTCTCCACAC CACACTGCTATCAGACAAGCTTTGGTTTGTTGGGACGAATTGACTAAGTTG ATCGCTTGGATGTCTTCTAACATCGGTGGTGGTGGTACTGCTGTTACTTTG CCATCTCACTCTACTAGAAAGTTGCAAACTAGATCTCAAACTTGGTTGGAA TCTAGAGAATACACTAAGCACTTGATCAGAGTTGAAAACTGGATCTTCAGA AACCCAGGTTTCGCTTTGGCTGCTGCTGCTATCGCTTGGTTGTTGGGTTCT TCTACTTCTCAAAAGGTTATCTACTTGGTTATGATCTTGTTGATCGCTCCA GCTTACTCTGGTGGTGGTGGTACTATCATCGTTAACCACGTTAACGACACT TGGGGTTTGAAGGTTAGACAATCTTTGTGGTTCCACTTGTCTTGTTTGACT TTCGGTCAACACACTGTTCAAGAATTCTTGGTTTCTTTCGGTGTTTGGATC AGAACTCCAGCTCCATACAGACCACCAAACGCTCCAATCTTGTCTACTTTG CCAGAACACACTGTTATCAGAAGAAGAGGTGGTGCTAGAGCTTCTAGATCT CCAAGAAGAAGAACTCCATCTCCAAGAAGAAGAAGATCTCAATCTCCAAGA AGAAGAAGATCTCAATCTCCATCTGCTAACTGT |

TABLE 15

Polynucleotide sequences that encode the peptide and protein sequences of ZIKV Capsid C antigen shown in Table 7.

| SEQ ID NO | ZIKV C CAPSID ANTIGEN | POLYNUCLEOTIDE SEQUENCE OF ZIKV C ANTIGEN |
|---|---|---|
| 103 | C full length | ATGAAGAACCCAAAGAAGAAGTCTGGTGGTTTCAGAATCGTTAACATGTTGAAGAGAGGTGTTGCTAGAGTTTCTCCATTCGGTGGTTTGAAGAGATTGCCAGCTGGTTTGTTGTTGGGTCACGGTCCAATCAGAATGGTTTTGGCTATCTTGGCTTTCTTGAGATTCACTGCTATCAAGCCATCTTTGGGTTTGATCAACAGATGGGGTTCTGTTGGTAAGAAGGAAGCTATGGAAACTATCAAGAAGTTCAAGAAGGACTTGGCTGCTATGTTGAGAATCATCAACGCTAGAAAGGAAAAGAAGAGAAGA |
| 104 | C alpha 2 | GGTCACGGTCCAATCAGAATGGTTTTGGCTATCTTGGCTTTCTTGAGATTCACTGCTATCAAGCCATCTTTGGGT |

TABLE 16

Polynucleotide sequences encoding WHcAg-ZIKV chimeric proteins with ZIKV C antigen shown in Table 8.

| SEQ ID NO | WHcAg (SEQ ID NO: 62) PLUS SEQ ID NO: | POLYNUCLEOTIDE SEQUENCE OF CHIMERIC PROTEIN WITH ZIKV C ANTIGEN |
|---|---|---|
| 105 | 103 | ATGGACATCGACCCATACAAGGAATTCGGTTCTTCTTACCAATTGTTGAACTTCTTGCCATTGGACTTCTTCCCAGACTTGAACGCTTTGGTTGACACTGCTACTGCTTTGTACGAAGAAGAATTGACTGGTAGAGAACACTGTTCTCCACACCACACTGCTATCAGACAAGCTTTGGTTTGTTGGGACGAATTGACTAAGTTGATCGCTTGGATGTCTTCTAACATCGGTGGTGGTGGTACTATGAAGAACCCAAAGAAGAAGTCTGGTGGTTTCAGAATCGTTAACATGTTGAAGAGAGGTGTTGCTAGAGTTTCTCCATTCGGTGGTTTGAAGAGATTGCCAGCTGGTTTGTTGTTGGGTCACGGTCCAATCAGAATGGTTTTGGCTATCTTGGCTTTCTTGAGATTCACTGCTATCAAGCCATCTTTGGGTTTGATCAACAGATGGGGTTCTGTTGGTAAGAAGGAAGCTATGGAAACTATCAAGAAGTTCAAGAAGGACTTGGCTGCTATGTTGAGAATCATCAACGCTAGAAAGGAAAAGAAGAGAAGAGGTGGTGGTGGTACTATCATCGTTAACCACGTTAACGACACTTGGGGTTTGAAGGTTAGACAATCTTTGTGGTTCCACTTGTCTTGTTTGACTTTCGGTCAACACACTGTTCAAGAATTCTTGGTTTCTTTCGGTGTTTGGATCAGAACTCCAGCTCCATACAGACCACCAAACGCTCCAATCTTGTCTACTTTGCCAGAACACACTGTTATCAGAAGAAGAGGTGGTGCTAGAGCTTCTAGATCTCCAAGAAGAAGAACTCCATCTCCAAGAAGAAGAAGATCTCAATCTCCAAGAAGAAGAAGATCTCAATCTCCATCTGCTAACTGT |
| 106 | 104 | ATGGACATCGACCCATACAAGGAATTCGGTTCTTCTTACCAATTGTTGAACTTCTTGCCATTGGACTTCTTCCCAGACTTGAACGCTTTGGTTGACACTGCTACTGCTTTGTACGAAGAAGAATTGACTGGTAGAGAACACTGTTCTCCACACCACACTGCTATCAGACAAGCTTTGGTTTGTTGGGACGAATTGACTAAGTTGATCGCTTGGATGTCTTCTAACATCGGTGGTGGTGGTACTGGTCACGGTCCAATCAGAATGGTTTTGGCTATCTTGGCTTTCTTGAGATTCACTGCTATCAAGCCATCTTTGGGTGGTGGTGGTACTATCATCGTTAACCACGTTAACGACACTTGGGGTTTGAAGGTTAGACAATCTTTGTGGTTCCACTTGTCTTGTTTGACTTTCGGTCAACACACTGTTCAAGAATTCTTGGTTTCTTTCGGTGTTTGGATCAGAACTCCAGCTCCATACAGACCACCAAACGCTCCAATCTTGTCTACTTTGCCAGAACACACTGTTATCAGAAGAAGAGGTGGTGCTAGAGCTTCTAGATCTCCAAGAAGAAGAACTCCATCTCCAAGAAGAAGAAGATCTCAATCTCCAAGAAGAAGAAGATCTCAATCTCCATCTGCTAACTGT |

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; [25, 26].

Vectors

Figure 2:
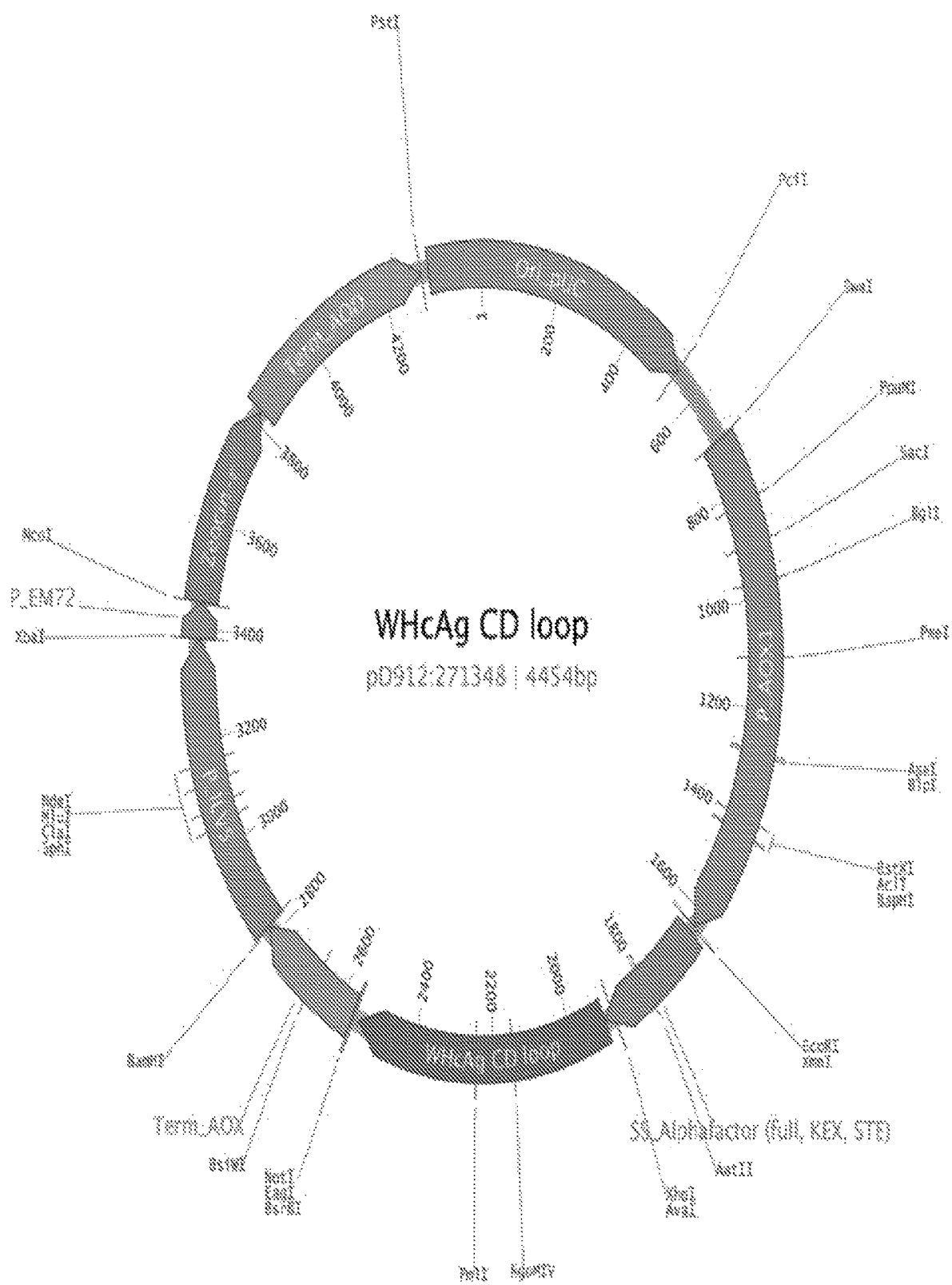
FIG. 2 depicts an example of a DNA construct for WHcAg chimeric VLP expression in a yeast system.

In some embodiments, vectors are used to express the polynucleotides described herein. Expression vectors generally include expression control sequences selected for a type of host cell to be used for protein expression. In some embodiments, the expression vector is a yeast expression vector. Various expression vectors are known in the art, including but not limited to pD912 or pD902 for secretory or cytosolic production of VLPs respectively (ATUM (available on the world wide web at atum.bio/)). Components and structure of an exemplary expression vector is depicted in FIG. 2.

VLP Production/Purification

Figure 4:
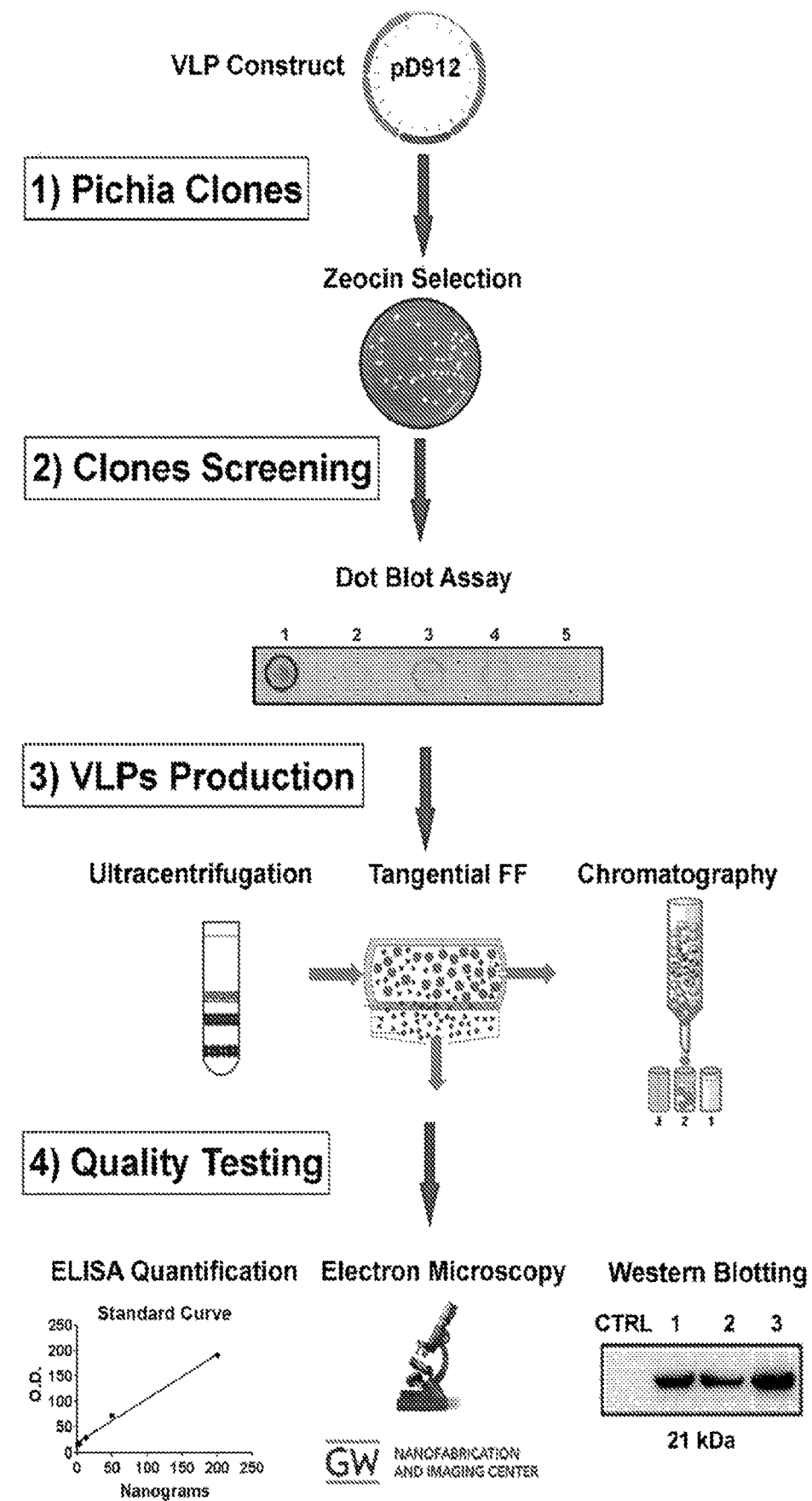
FIG. 4 shows a flow chart for production, purification, and quality testing of WHcAg-ZIKV chimerics.

A number of appropriate yeast strains for protein expression exist, including but not limited to *Komagataella phaffii* Kurtzman (ATCC® 76273™) or *Komagataella pastoris* (ATCC® 76274™). Using in silico analysis we have designed codon optimized DNA constructs expressing the Zika Virus antigens conserved between different strains (FIGS. 3A and 3B). VLPs are produced by recombinant constructs using the promoter from the *Pichia* alcohol oxidase 1 (AOX1) gene to drive production of the recombinant protein according to ATUM (available on the world wide web at atum.bio/) with further optimization. VLPs are purified by, for example, precipitation, ultracentrifugation, chromatography, tangential flow filtration (TFF) or ultrafiltration methods or combination of such methods (FIG. 4) [16]. VLPs are quantified for purity and antigenicity using biochemical and immune assays such as Western blotting, dot blot, ELISA (FIGS. 6 and 7), gel electrophoresis (SDS-PAGE or native Agarose gel, combined with Coomassie Blue staining), and electron microscopy (FIG. 5) [16].

Antigenic and Immunogenic Characterization of VLPs

A. Antigenicity

Prior to immunogenicity testing, VLPs comprising a chimeric peptide as described herein are characterized for expression, particle assembly, and ability to bind a peptide-specific antibody. Capture enzyme-linked immunosorbent assays (ELISAs), dot blot or Western blot are utilized and designed to assess three VLP properties according to methods known in the art [16](FIGS. 6 and 7): 1) protein expression of the WHcAg polypeptide by use of an antibody that is specific for the WHcAg (e.g. Santa Cruz Biotechnology, antibody Hep B cAg Antibody (13A9): sc-23946); 2) particle assembly using an antibody specific for a conformational epitope on WHcAg; and 3) display of the epitope of a Zika peptide of the disclosure by use of Zika peptide-reactive antibodies (e.g., ATCC BEI Resources NR-50414 Monoclonal Anti-Zika Virus Envelope (E) Protein, Clone ZV-2). Constructs that are positive for all three properties are selected for further purification (e.g., Ultracentrifugation, Ultrafiltration, Chromatography). In brief, expression, particle assembly, and antibody binding are assayed by ELISA, dot blot, and Western blotting. SDS-PAGE and Agarose electrophoresis, along with electron microscopy (FIG. 5), are used to assess the purity and assembly of VLPs. VLPs can be tested for non-cross-reactivity using in vitro Antibody-Dependent Enhancement Assay according to the literature [27].

B. Immunogenicity

Figure 9:
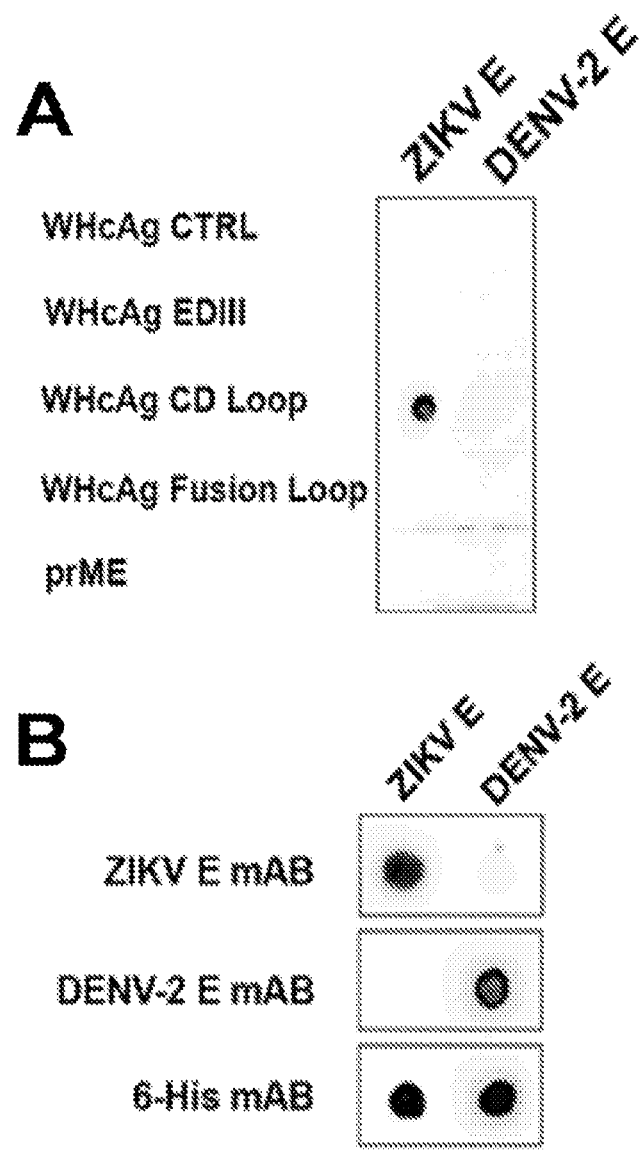
FIG. 9 illustrates dot blot analysis of serum pools from animals immunized with different WHcAg-ZIKV chimeric VLPs using Zika Virus (ZIKV) Envelope (E) recombinant protein and Dengue Virus 2 (DENV-2) E recombinant protein as antigen (FIG. 9A). Commercially available monoclonal antibodies (mAb) are used for assay control (FIG. 9B).
Figure 11:
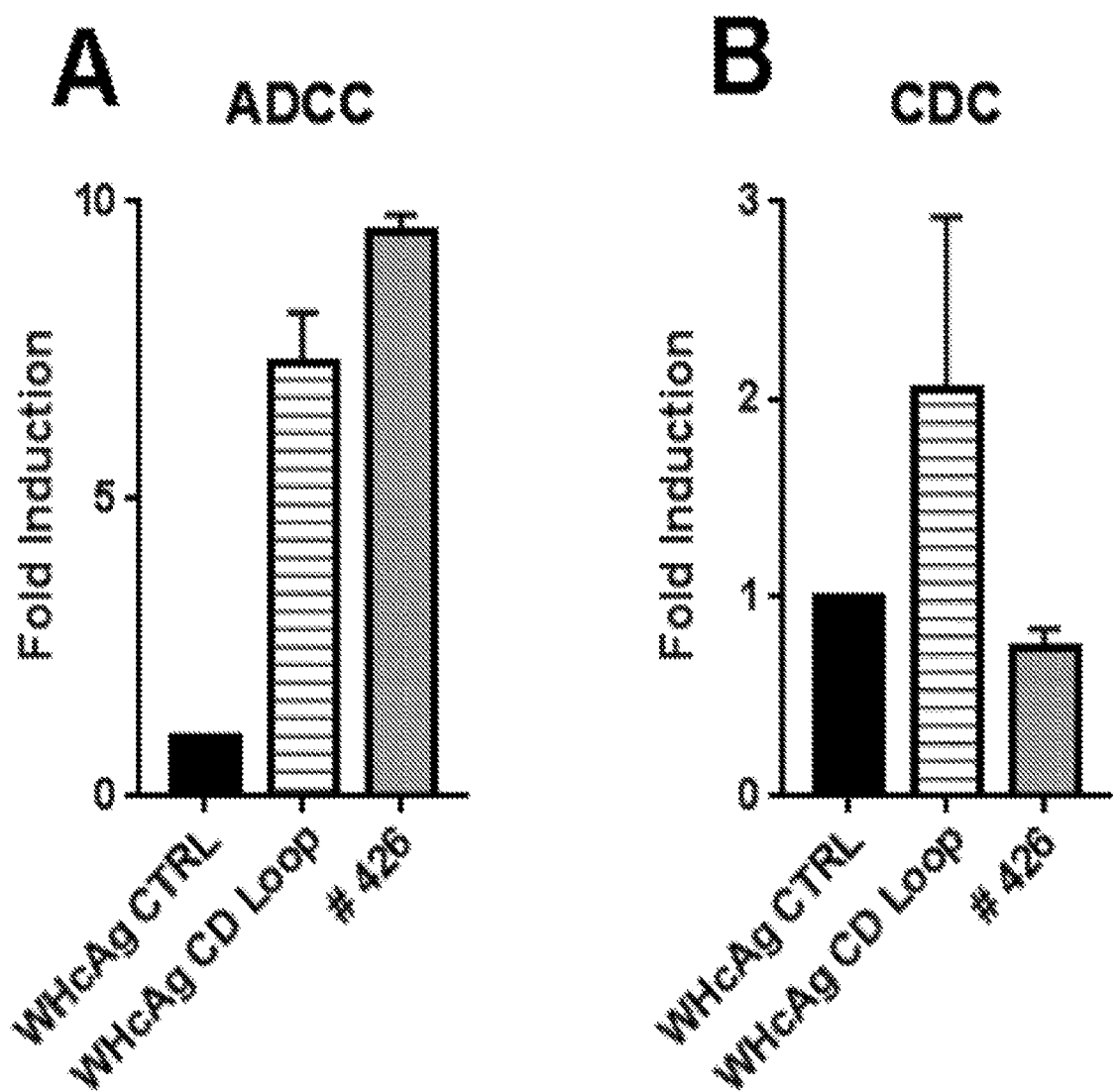
FIG. 11 demonstrates that WHcAg CD loop VLP vaccine candidate induced protective antibodies against Zika Virus in a mouse model.

VLP-based vaccine antigenicity is assessed in different adjuvant formulations in animal model such as immunocompetent mouse model (e.g. BALB/c) or immunodeficient mouse model (e.g. AG129 and A129). The immune response to VLPs is assessed in mice models for Zika Virus infection according to the literature [27, 28]. In addition to anti-insert, anti-peptide-protein and anti-WHcAg antibody endpoint titers, antibody specificity, isotype distribution, antibody persistence and antibody avidity are monitored. VLPs immune stimulation can be tested for inducing non-cross-reactivity antibody analyzing serum samples of VLP immunized mice by dot blot analysis (FIG. 9) or in vitro for Antibody-Dependent Enhancement Assay according to the literature [27]. Immune sera are compared to the activity of a reference antibody by ELISA and neutralization assays known in the art [16, 28]. Immune responses are tested in vivo in various mammalian species (e.g., rodents such as rats and mice, nonhuman primates (NHP), and/or humans).

Compositions

The invention includes compositions that comprise a chimeric peptide or VLP described herein or a polynucleotide encoding the chimeric peptide. In some embodiments, the composition is an antigenic composition. In some embodiments, the composition further comprises a pharmaceutically acceptable carrier. The term "carrier" refers to a vehicle within which the VLP, vector, chimeric peptide or polynucleotide encoding the chimeric peptide is administered to a mammalian subject. The term carrier encompasses diluents, excipients, adjuvants and combinations thereof. Pharmaceutically acceptable carriers are well known in the art (see, e.g., Remington's Pharmaceutical Sciences by Martin, 1975).

Exemplary "diluents" include sterile liquids such as sterile water, saline solutions, and buffers (e.g., phosphate, tris, borate, succinate, or histidine). Exemplary "excipients" are inert substances that may enhance vaccine stability and include but are not limited to polymers (e.g., polyethylene glycol), carbohydrates (e.g., starch, glucose, lactose, sucrose, or cellulose), and alcohols (e.g., glycerol, sorbitol, or xylitol).

Adjuvants are broadly separated into two classes based upon their primary mechanism of action: vaccine delivery systems (e.g., emulsions, microparticles, immune stimulating complexes (ISCOMS), or liposomes) that target associated antigens to antigen presenting cells (APC); and immunostimulatory adjuvants (e.g., LPS, MPL, or CpG) that directly activate innate immune responses. Different types of adjuvants can be combined to enhance their immunostimulatory activity (e.g. AS04 (GSK) is composed of MPL mixed with an aluminum salt).

A. Traditional and Molecular Adjuvants

Although adjuvants are not required when using the WHcAg delivery system disclosed herein, some embodiments of the present invention employ adjuvant formulations. Adjuvants are a class of immunomodulatory molecules and compositions able to augment vaccine effectiveness and safety by: 1) enhancing immunogenicity and increasing the duration of protection; 2) broadening the induction of the immune response; 3) reducing vaccine dosage and vaccination cost (antigen sparing); 4) accelerating the immune response; 5) stimulating a stronger immunological memory; 6) improving efficacy in weak responder patients such as neonates, the elderly and immunocompromised individuals [12]. In addition, some adjuvants formulation may also increase VLP-based vaccine stability and play an important role in VLPs delivery. Adjuvant formulations for this disclosure includes the classical aluminum-based adjuvants, and novel classes of adjuvants such as liposomes (e.g., CAF01), agonists of pathogen recognition receptors (e.g. Immune stimulating complexes (ISCOMs), Lipid A analogs (MPL, RC-529, and GLA), double stranded RNA analogs (e.g. Poly I:C and Poly ICLC), cytidine monophosphate guanosine oligodeoxynucleotide (e.g. CpG, CpG ODN), flagellin, imidazoquinoline (Imiquimod and Resiquimod), polymeric particles (e.g. Chitosan), emulsions (e.g. squalene oil-based), cytokines (e.g. Interleukin-12), bacterial toxins (e.g Cholera Toxin (CT) or *Escherichia coli* enterotoxin (LT)), Quil A and other saponins known in the art, and the plant polysaccharide inulin [12]. Specifically, immunization in saline effectively elicits immune response against the vaccine preparation antigen/s. However, formulation in non-inflammatory agents such as IFA (mineral oil), Montanide ISA 720 (squalene), and aluminum phosphate (AlP04), or immunomodulatory agents or adjuvants enhance vaccine immunogenicity. Additionally, administration of WHcAg results in the production of multiple IgG isotypes, regardless of which if any adjuvant is employed. The WHcAg VLPs have shown superior stability as compared to recombinant protein from subunit vaccines in the particularly harsh mucosal environment. This characteristic is quite advantageous for developing vaccines for mucosal administration such as the oral, nasal, rectal and vaginal route. Inclusion of a CpG motif also enhances the primary response. Moreover, use of an inflammatory adjuvant such as the Ribi formulation is not more beneficial than is the use of non-inflammatory adjuvants, indicating that the benefits of the adjuvants result from a depot effect rather than from non-specific inflammation. Thus, the core platform is used with no adjuvant or with non-inflammatory adjuvants depending upon the application and the quantity of antibody desired. In some embodiments of the present disclosure, IFA is used in murine studies, whereas alum or squalene is used in human studies. In instances where it is desirable to deliver hybrid WHcAg particles in a single dose in saline, a molecular adjuvant is employed. A number of molecular adjuvants are employed to bridge the gap between innate and adaptive immunity by providing a co-stimulus to target B cells or other APCs.

B. Other Molecular Adjuvants

Genes encoding the murine CD40L (both 655 and 470 nucleic acid versions) have been used successfully to express these ligands at the C-terminus of WHcAg (See, e.g., WO 2005/011571). Moreover, immunization of mice with hybrid WHcAg-CD40L particles results in the production of higher anti-core antibody titers than does the immunization of mice with WHcAg particles. However, lower than desirable yields of purified particles have been obtained. Therefore, mosaic particles containing less than 100% CD40L-fused polypeptides are produced to overcome this problem. The other molecular adjuvants inserted within the WHcAg, including the C3d fragment, BAFF and LAG-3, have a tendency to become internalized when inserted at the C-terminus. Therefore tandem repeats of molecular adjuvants are used to resist internalization. Alternatively, various mutations within the so-called hinge region of WHcAg, between the assembly domain and the DNA/RNA-binding region of the core particle are made to prevent internalization of C-terminal sequences. However, internalization represents a problem for those molecular adjuvants such as CD40L, C3d, BAFF and LAG-3, which function at the APC/B cell membrane. In contrast, internalization of molecular adjuvants such as CpG ODN is not an issue as these types of adjuvants function at the level of cytosolic receptors.

Another type of molecular adjuvant or immune enhancer is the inclusion within hybrid core particles of a $CD4^+$ T cell epitope, preferably a "universal" $CD4^+$ T cell epitope that is recognized by a large proportion of $CD4^+$ T cells (such as by more than 50%, preferably more than 60%, more preferably more than 70%, most preferably greater than 80%), of $CD4^+$ T cells. In one embodiment, universal $CD4^+$ T cell epitopes bind to a variety of human MHC class II molecules and are able to stimulate T helper cells. In another embodiment, universal $CD4^+$ T cell epitopes are preferably derived from antigens to which the human population is frequently exposed either by natural infection or vaccination [29]. A number of such universal $CD4^+$ T cell epitopes have been described including, but not limited to: Tetanus Toxin (TT) residues 632-651; TT residues 950-969; TT residues 947-967, TT residues 830-843, TT residues 1084-1099, TT residues 1174-1189 [30]; Diphtheria Toxin (DT) residues 271-290; DT residues 321-340; DT residues 331-350; DT residues 411-430; DT residues 351-370; DT residues 431-450 [31]; *Plasmodium falciparum* circumsporozoite (CSP) residues 321-345 and CSP residues 378-395 [32]; Hepatitis B antigen (HBsAg) residues 19-33 [33]; Influenza hemagglutinin residues 307-319; Influenza matrix residues 17-31 [34]; and measles virus fusion protein (MVF) residues 288-302 [35].

Methods of Inducing an Immune Response

The invention includes methods for eliciting an immune response in a subject in need thereof, comprising administering to the subject an effective amount of an antigenic composition comprising one or more of the peptides, proteins, or VLP described herein. Also provided are methods for eliciting an immune response in a subject in need thereof, comprising administering to the subject an effective amount of an antigenic composition comprising a polynucleotide encoding a chimeric peptide described herein, wherein said chimeric polypeptide expressed in vivo assembles as a hybrid VLP. Unless otherwise indicated, the antigenic composition is an immunogenic composition.

The immune response raised by the methods of the present disclosure generally includes an antibody response, preferably a neutralizing antibody response, antibody dependent cell-mediated cytotoxicity (ADCC), antibody cell-mediated phagocytosis (ADCP), complement dependent cytotoxicity (CDC), and T cell-mediated response such as CD4*, CD8*. The immune response generated by the chimeric peptides, proteins, or VLPs as disclosed herein generates an immune response that recognizes, and preferably ameliorates and/or neutralizes Zika virus. Methods for assessing antibody responses after administration of an antigenic composition (immunization or vaccination) are known in the art and/or described herein. In some embodiments, the immune response comprises a T cell-mediated response (e.g., peptide-specific response such as a proliferative response or a cytokine response). In preferred embodiments, the immune response comprises both a B cell and a T cell response. Antigenic compositions can be administered in a number of suitable ways, such as intramuscular injection, subcutaneous injection, intradermal administration and mucosal administration such as oral or intranasal. Additional modes of administration include but are not limited to intranasal administration, intra-vaginal, intra-rectal, and oral administration. A combination of different routes of administration in the immunized subject, for example intramuscular and intranasal administration at the same time, is also contemplated by the disclosure.

Antigenic compositions may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >55 years old, >60 years old, preferably >65 years old), and the young (e.g., <6 years old, 1-5 years old, preferably less than 1 year old). Additional subjects for receiving the vaccines or compositions of the disclosure include naïve (versus previously infected) subjects, currently infected subjects, or immuno-compromised subjects.

Administration can involve a single dose or a multiple dose schedule. Multiple doses may be used in a primary immunization schedule and/or in a booster immunization schedule. In a multiple dose schedule the various doses may be given by the same or different routes, e.g., a parenteral prime and mucosal boost, or a mucosal prime and parenteral boost. Administration of more than one dose (typically two doses) is particularly useful in immunologically naive subjects or subjects of a hyporesponsive population (e.g., diabetics, or subjects with chronic kidney disease (e.g., dialysis patients)). Multiple doses will typically be administered at least 1 week apart (e.g., about 2 weeks, about 3 weeks, about 4 weeks, about 6 weeks, about 8 weeks, about 10 weeks, about 12 weeks, or about 16 weeks). Preferably multiple doses are administered from one, two, three, four or five months apart. Antigenic compositions of the present disclosure may be administered to patients at substantially the same time as (e.g., during the same medical consultation or visit to a healthcare professional) other vaccines.

In general, the amount of protein in each dose of the antigenic composition is selected as an amount effective to induce an immune response in the subject, without causing significant, adverse side effects in the subject. Preferably the immune response elicited includes: neutralizing antibody response; antibody dependent cell-mediated cytotoxicity (ADCC); antibody cell-mediated phagocytosis (ADCP); complement dependent cytotoxicity (CDC); T cell-mediated response such as CD4*, CD8*, or a protective antibody response. Protective in this context does not necessarily require that the subject is completely protected against infection. A protective response is achieved when the subject is protected from developing symptoms of disease, especially severe disease associated with the pathogen corresponding to the heterologous antigen. As described above, the immune response generated by the chimeric peptides or VLP as disclosed herein generates an immune response that recognizes, and preferably ameliorates and/or neutralizes, Zika virus.

The WHcAg-ZIKV chimera vaccine administration and formulation may be optimized to induce mucosal immune protection for preventing sexual transmission. The invention contemplates mucosal route administration such as nasal, vaginal, rectal or oral. The vaccine formulation can be optimized using adjuvant/s formulation for stimulation of mucosal immune response such as IgA and induction of mucosa-associated lymphoid tissues (MALTs). Adjuvants for mucosal immunization considered for WHcAg-ZIKV chimera vaccine include but are not limited to polymeric particles (e.g., Chitosan), cholera toxin (CT), and imidazoquinoline (Imiquimod and Resiquimod).

The WHcAg-ZIKV chimera vaccine formulation and administration may be designed to achieve a broader immune response for protection against multiple transmission routes: mosquito transmission, blood transfusion, maternal transmission, sexual transmission, organ transplant and other possible routes.

The amount of antigen (e.g., VLP) can vary depending upon which antigenic composition is employed. Generally, it is expected that each human dose will comprise 0.1-2000 µg of protein (e.g., chimeric peptide), such as from about 1 µg to about 2000 µg, for example, from about 1 µg to about 1500 µg, or from about 1 µg to about 1000 µg, or from about 1 µg to about 500 µg, or from about 1 µg to about 100 µg. In some embodiments, the amount of the protein is within any range having a lower limit of 0.1, 1, 5, 10, 20, 30, 40, 50, 60, 70, 80, 90, 100, 110, 120, 130, 140, 150, 160, 170, 180, 190, 200, 210, 220, 230, 240 or 250 µg, and an independently selected upper limit of 2000, 1950, 1900, 1850, 1800, 1750, 1700, 1650, 1600, 1550, 1500, 1450, 1400, 1350, 1300 or 1250, 1200, 1150, 1100, 1050, 1000, 950, 900, 850, 800, 750, 700, 650, 600, 550, 500, 450, 400, 350, 300 or 250 µg, provided that the lower limit is less than the upper limit. Generally a human dose will be in a volume of from 0.1 ml to 1 ml, preferably from 0.25 ml to 0.5 ml. The amount utilized in an antigenic composition is selected based on the subject population. An optimal amount for a particular composition can be ascertained by standard studies involving observation of antibody titers and other responses (e.g., antigen-induced cytokine secretion) in subjects. Following an initial vaccination, subjects can receive a boost in about 4-12 weeks.

Articles of Manufacture and Kits

Figure 12:
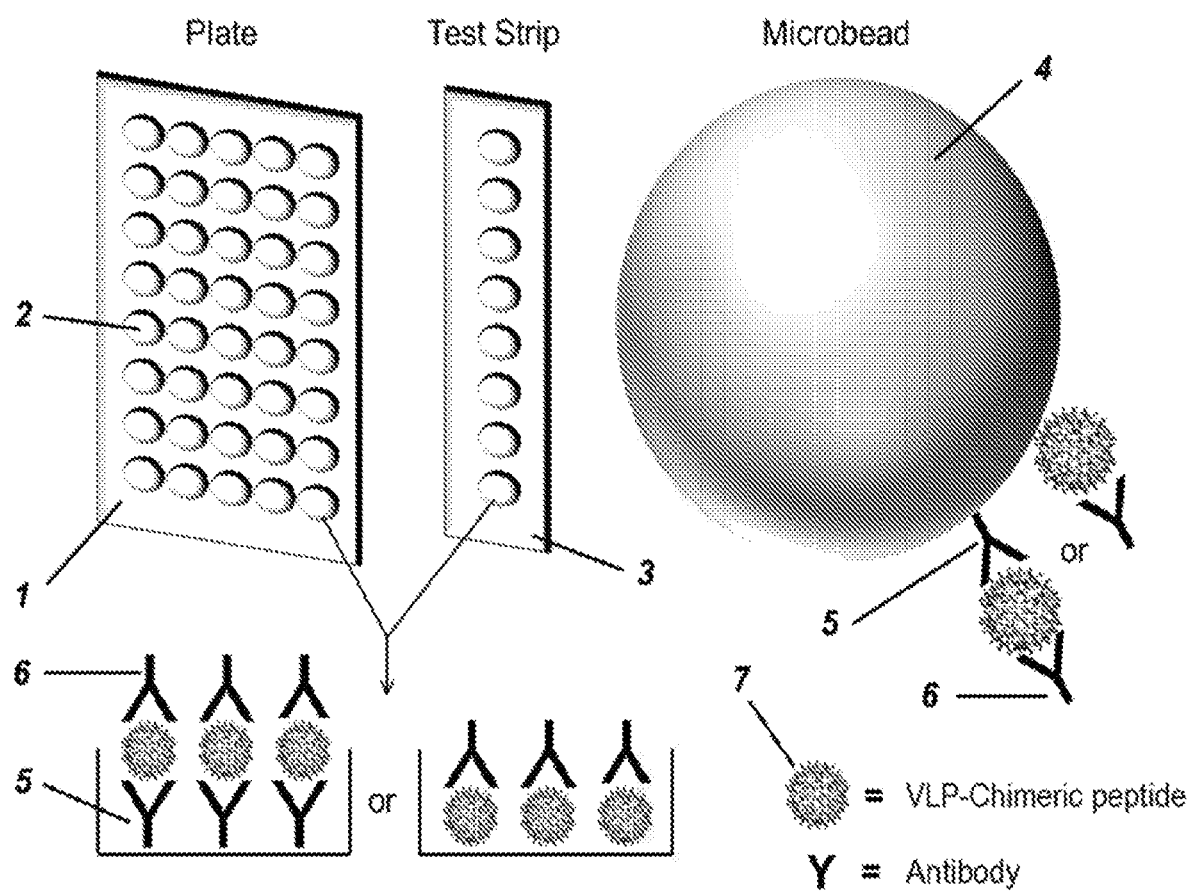
FIG. 12 depicts an exemplary plate, test strip, and microbead of the invention.
Figure 13:
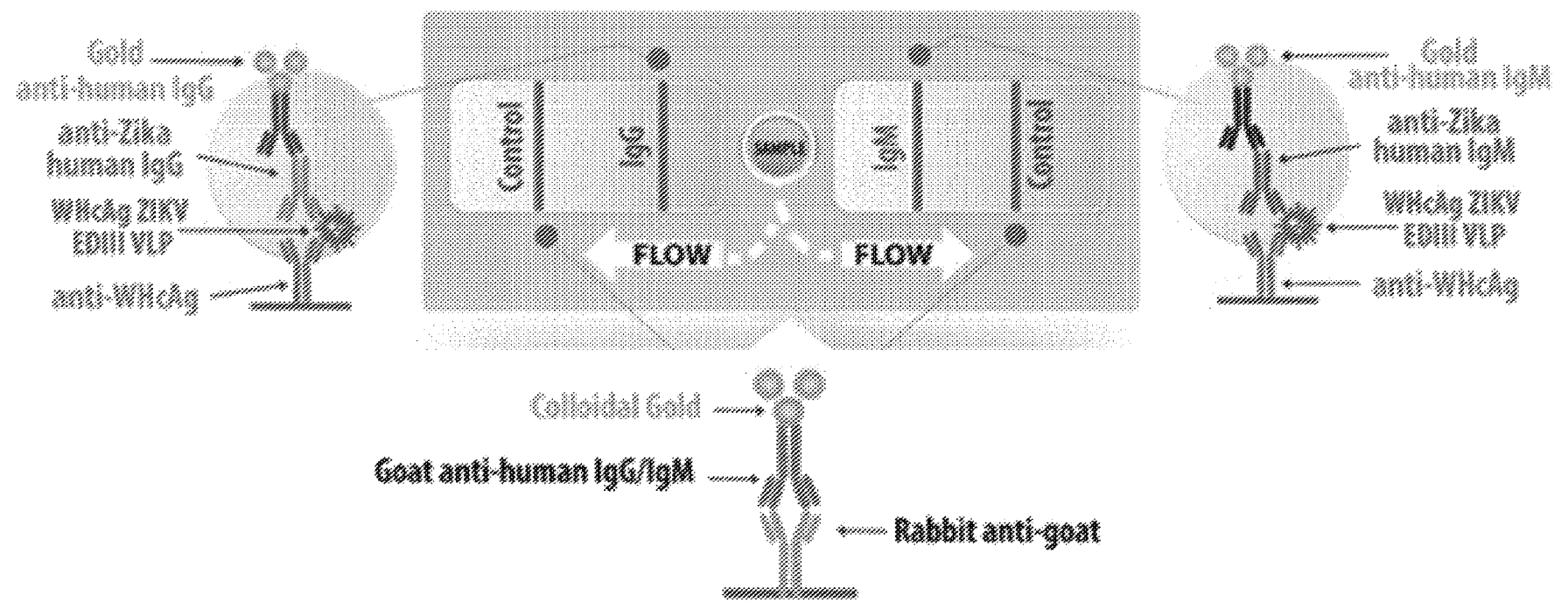
Figure 14:
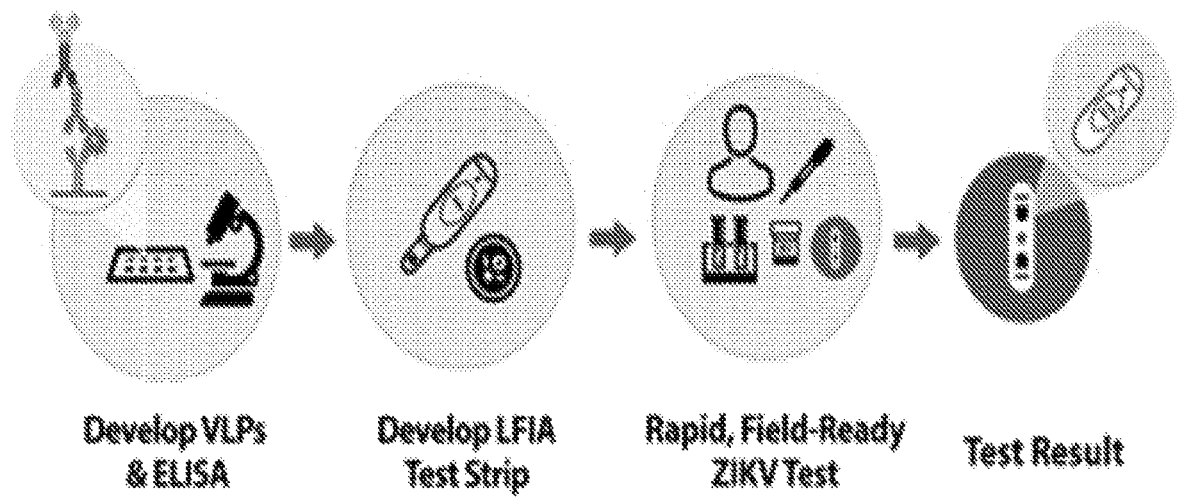
FIG. 14 shows WHcAg-ZIKV chimeric VLP Lateral Flow Immunoassay Application (LFIA).

The invention additionally includes articles of manufacture and kits comprising a peptide, a chimeric peptide or protein, a fusion protein, or VLP described herein (FIGS. 12-14. In some embodiments, the kits further comprise a solid support (e.g., referring to FIG. 12, the solid support can be a plate 1, a test strip 3, or a microbead 4). Kits or articles also comprise, in some variations, a capture antibody 5 and/or a detection antibody 6. In some embodiments, the kits further comprise instructions for measuring peptide-specific antibodies. In some embodiments, the antibodies are present in serum from a blood sample of a subject immunized with an antigenic composition comprising the VLP.

Chimeric WHcAg-ZIKV VLP are designed for capturing anti-ZIKV and include but are not limited to specific and selected amino acids sequence(s) from ZIKV viral protein E, NS1, prM/M or C (see Tables 1, 3, 5, and 7). Such recombinant amino acid sequences are inserted at a location between two amino acids in the region of amino acids 77 to 82 of the WHcAg protein (GenBank accession number NP_671816). See Table 2, 4, 6, and 8.

As used herein, the term "instructions" refers to directions or protocols for using reagents contained in the kit for measuring antibody titer. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination.

As described herein, the invention also includes methods for screening anti-Zika virus antibodies comprising: a) measuring binding of an antibody or fragment thereof to a VLP as described herein; and b) measuring binding of the antibody or fragment thereof to a Woodchuck Hepatitis core Antigen protein (WHcAg) VLP devoid of a peptide as disclosed herein; and c) determining that the antibody or fragment thereof is specific or selective for a peptide of the disclosure when the antibody or fragment thereof binds to the chimeric VLP but not the WHcAg VLP devoid of a peptide of the disclosure. In some embodiments, the VLP is attached to a solid support. In further embodiments, the solid support is a microbead, an assay plate, a test strip, or a filter as depicted in FIGS. 12 and 13. Methods for (i) screening anti-Zika virus antibodies; (ii) detecting or measuring antibodies to Zika virus in a biological sample; or (iii) detecting a Zika virus infection may all be performed using a solid support as shown in FIGS. 12, 13, and 14. In various embodiments, antigen-antibody complex formation and detection may be performed by attaching a VLP as described herein directly to a solid support (such as, e.g., a plate 1, a test strip 3, or a microbead 4) and then contacting the VLP 7 with a test sample putatively containing an anti-Zika virus antibody 6 (see FIG. 12). Alternatively, or in addition, a VLP of the disclosure may be indirectly attached to a solid support by first attaching an anti-VLP antibody 5 to the solid support and then contacting the VLP 7 with the anti-VLP antibody to form a complex (see FIG. 12). A test sample putatively containing an anti-Zika virus antibody 6 is then applied, creating a "sandwich" complex between the anti-VLP antibody, the VLP, and the antibody from the test sample having an affinity for the VLP. Regardless of the method chosen, detection of binding of an antibody from the test sample to the VLP is indicative of a Zika virus antibody being present in the sample.

Sandwich ELISA is used for detection of Zika Virus antibody in patients. The sandwich ELISA test for human Immunoglobulin G (IgG) is useful for the detection of circulating long-lived, neutralizing anti-Zika virus antibody. The Immunoglobulin M (IgM) sandwich ELISA is very effective for the early onset of the infection when IgM response peaks. Using the ELISA format, the wells of microtitre plates are coated with either Goat anti-human IgG or IgM, followed by incubation with subject serum containing anti-ZIKV antibodies in case of viral infection. After incubation, VLPs carrying Zika Virus peptide sequence are added to the well, unbound antigen is washed out, and Horseradish Peroxidase (HRP) conjugated anti-Zika Virus monoclonal antibody (revealing monoclonal antibody) is added. The bound conjugate is detected after addition of substrate solution such as TMB or enhanced chemiluminescence (ECL) reagent. The TMB reaction is terminated using stop solution and the degree of substrate hydrolysis is measured using spectrophotometry plate reader. Alternatively, the ECL signal can be detected using a plate reader with luminometer detector right after the ECL substrate addition.

Early and accurate diagnosis of Zika Virus is very important, especially in the field. The Lateral Flow Immuno Assay (LFIA) is able to detect anti Zika Virus antibodies in sera from clinically proven patients, as well as in healthy control subjects. The LFIA is used to detect subject serum antibody against Zika Virus antigen. Colloidal gold particle labelled goat anti human IgG/IgM (e.g., 1.0 mg/L) is used as the detector reagent. Recombinant VLP protein (e.g., 1.0 mg/L) is captured in the strip by anti-WHcAg antibody or absorbed directly to the support. Rabbit anti-goat IgG (1.0 mg/L) are immobilized in test and control lines, respectively, on a nitrocellulose membrane, acting as the capture reagents (FIGS. 13 and 14).

EXAMPLES

As described herein, the present disclosure is related to chimeric VLPs containing and displaying epitopes and antigen from ZIKV. The disclosure also provides methods for creation and production of such chimeric VLPs to their applications, including but not limited to vaccines, diagnostics, clinical studies, assay development and antibody discovery. The recombinant and chimeric WHcAg VLP function as a carrier for highly immunogenic and optimized amino acids sequence(s) from the Domain III of the E protein (E DIII) or other immunogenic sequences from E protein of ZIKV. In addition, chimeric WHcAg VLP may include specific and selected amino acids sequence(s) from ZIKV viral protein NS1, prM/M or C (see Tables 1, 3, 5, and 7). Such recombinant amino acid sequences are inserted at a location between amino acids 77 and 82 of the WHcAg protein (GenBank accession number NP_671816). See Tables 2, 4, 6, and 8.

The disclosure also provides optimized production and purification of recombinant WHcAg chimeric VLPs in Yeast cellular system: *Komagataella phaffii* Kurtzman (ATCC® 76273™). The WHcAg chimera constructs are subcloned in pD912 vector from ATUM (formerly DNA2.0) (available on the world wide web at atum.bio) with secretion alpha-factor signal (SS_Alphafactor) linked to the N terminus of the WHcAg chimera sequence (FIG. 2). Alternatively, the WHcAg chimeric construct is inserted in pD902 vector without a secretion signal for cytosolic protein expression and accumulation. Vector is linearized and used for creating high expressing yeast clones by transformation or electroporation in yeast cells. Yeast clones are selected using Zeocin resistance marker in semi-solid culture (YPD Agar). WHcAg chimera protein expression induction is obtained by optimized culture and using methanol supplementation. The secreted VLPs are purified from the yeast culture media by biochemical methods such as precipitation, ultracentrifugation, ultrafiltration, chromatography, tangential flow filtration (TFF) or a combination of such methods. VLPs that are expressed and accumulated in the yeast cytosol (not secreted) are purified by cell lysis methods (physical and chemical) followed by precipitation, ultracentrifugation, ultrafiltration, chromatography, tangential flow filtration (TFF) or a combination of such methods.

Cimica et al. [16] have developed a VLP vaccine for Respiratory Syncytial Virus (RSV) at TechnoVax Inc. (Tarrytown, N.Y.). RSV-like particle (RS-VLP) vaccine was assembled with human metapneumovirus (hMPV) matrix protein as the structural particle scaffold, and RSV fusion glycoprotein (F) as the main immunogen. Structural vaccinology was applied for increasing and optimizing F protein immunogenicity; multiple F constructs were generated and tested in antigenically different conformations. The immunization with RS-VLP vaccine adjuvanted with the squalene-based emulsion afforded full protection and was safe in the mouse model of RSV disease [16]. The present disclosure utilized an alternative approach for the creation and production of ZIK-VLP. VLPs can be produce in large scale fermentation of *Pichia pastoris* culture form selected clones. VLP purification is performed using state of the art methods such as: precipitation, ultracentrifugation, Tangential Flow Filtration (TFF), ultrafiltration and chromatography. Purity and quality of ZIK-VLPs chimera is tested by immunoassays and electron microscopy.

Example 1

Early Development of a ZIKV VLP Candidate

The ZIKV Envelope (E) protein is a primary target for vaccine development because it displays epitopes able to induce neutralizing and protective antibody in the host [36]. The E protein comprises the majority of the flavivirus surface and plays multiple roles in viral infection: host receptor recognition and binding, membrane fusion, viral release from endosomal compartment, virion assembly, and egress. The ZIKV shell is assembled with 180 copies of the E protein and comprises the majority of the virion surface [23, 37]. The E protein of any flavivirus including ZIKV shows a highly conserved structure that is divided into three domains: Domain I (DI) consisting of a central beta-barrel domain; Domain II (DII) important for dimerization and virion assembly; and Domain III (DIII) characterized by an immunoglobulin-like segment. Noticeably, the distal part of the DII contains a Fusion Loop domain with very high amino acid sequence identity between flavivirus.

Several studies in flavivirus including ZIKV have demonstrated that the E protein DIII (EDIII) is a primary antigenic target of specific neutralizing antibodies [38, 39]. In particular, it was shown that structural domains inside DIII can induce highly neutralizing and protective antibodies in a mouse model [38]. The ZIKV Fusion Loop domain in DII can induce highly neutralizing antibodies [18] that are able to cross react with other flavivirus. Cross-reacting antibodies, however, have been demonstrated to induce antibody-dependent enhancement (ADE) of ZIKV infection in patients with a history of DENV infection [40]. The Fusion Loop domain is implicated in ADE effects of ZIKV infection [41]. For these reasons, the present disclosure describes the use of a ZIK-VLP vaccine using EDIII selected epitopes as immunogen targets for neutralizing ZIKV.

Structural vaccinology was utilized for selecting specific epitopes and antigens from ZIKV EDIII (FIG. 3 and Table 5). Antigenic sequences from Zika Virus Envelope (E) protein were identified using the Cn3D software from NIH (available on the world wide web at ncbi.nlm.nih.gov/Structure/CN3D/cn3d.shtml) for structural analysis, and the CLC Sequence Viewer Qiagen (available on the world wide web at qiagenbioinformatics.com/products/clc-sequence-viewer/) for analysis of acid sequence conservation and specificity between flavivirus. The sequencing and structural data was obtained from US National Library of Medicine National Institutes of Health (available on the world wide web at ncbi.nlm.nih.gov/pubmed). Using recombinant DNA technology, such E DIII epitopes were included in the Woodchuck Hepatitis core Antigen (WHcAg) scaffolding system for delivery of the epitopes (FIG. 3).

TABLE 17

DNA Constructs for production of ZIKV-VLPs

| CONSTRUCTS GENERATED | TESTED |
| --- | --- |
| 1 WHcAg (MOCK CONTROL FOR IMMUNIZATION) | YES |
| 2 WHcAg CHIMERA E PROTEIN DOMAIN III FULL LENGTH | YES |
| 3 WHcAg CHIMERA E PROTEIN DOMAIN III, A-B LOOP | YES |
| 4 WHcAg CHIMERA E PROTEIN DOMAIN III, CX-C-D-DX LOOP | YES |
| 5 WHcAg CHIMERA E PROTEIN DOMAIN III, DX-E LOOP | YES |
| 6 WHcAg CHIMERA E PROTEIN DOMAIN III, F-G LOOP | YES |
| 7 E PROTEIN (POSITIVE CONTROL FOR IMMUNIZATION) | YES |

Such a system has been used successfully for vaccine candidates: human HBV surface protein (HBsAg) or HBV core antigen protein (HBcAg) are currently in clinical trials for influenza virus and the malaria parasite (*Plasmodium falciparum*) [42]. Although the HB-VLP system is a very efficient platform for antigen delivery to APCs and B cells [43], such technology has two limitations: i) HBV proteins may not assemble properly because the steric hindrance of the carried antigen; ii) preexisting immunity against HBV may reduce greatly the immunization efficiency. For these reasons, we will adopt the WHcAg scaffolding system [21] that was successfully applied for developing VLP-based vaccines for RSV [44], and malaria parasite [45]. The WHcAg has the ability to function as a carrier for a selected epitope/antigen peptide (e.g., 5-100 amino acids) for inducing a very specific antibody response. Applying structural vaccinology, we have designed ZIKV DIII-optimized antigens comprising either full length DIII domain, or selected DIII structural domains comprising the A-B loop, C-D loop, D-E loop and F-G loop (Table 1 and 2, FIG. 3). Using recombinant expression technology, DNA constructs for ZIK-VLP expression in *Pichia pastoris* were developed, and the potential vaccine candidates are tested for efficacy and safety in an A129, AG129 and C57BL/6 treated with anti-IFNAR1 antibodies mouse model for ZIKV infection.

Example 2

Production of ZIK-VLP Using the *Pichia* Expression System

Figure 5:
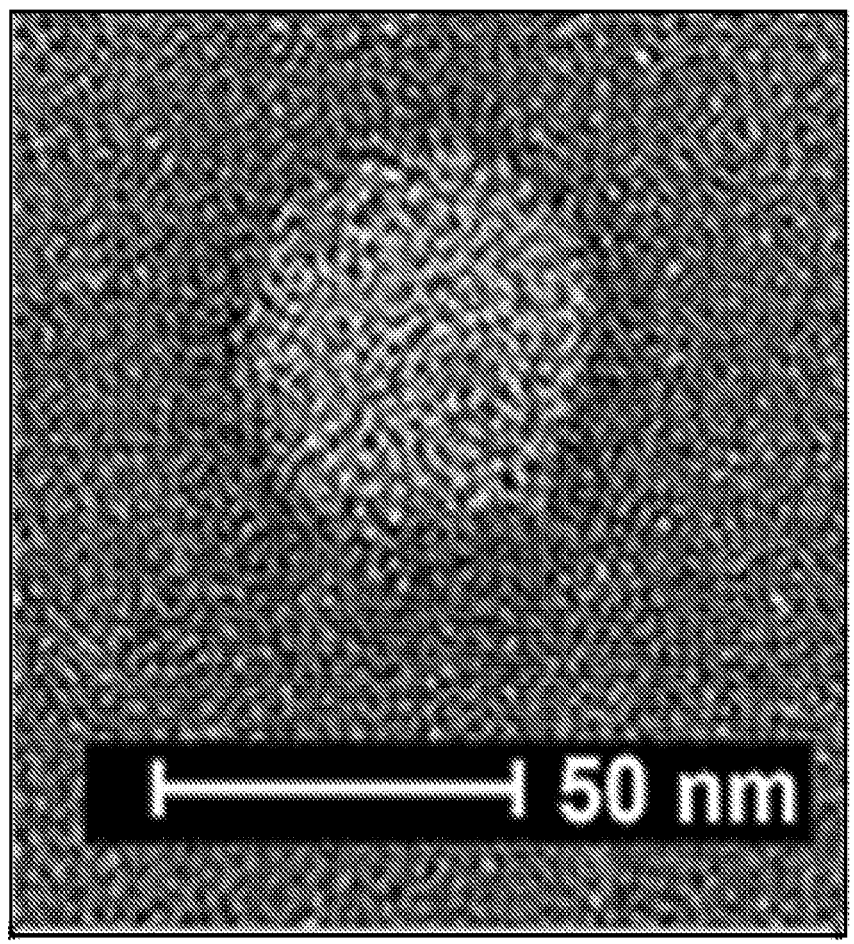
FIG. 5 shows a WHcAg VLP analyzed by electron microscopy. Scale bar=50 nanometers (nm).
Figure 6:
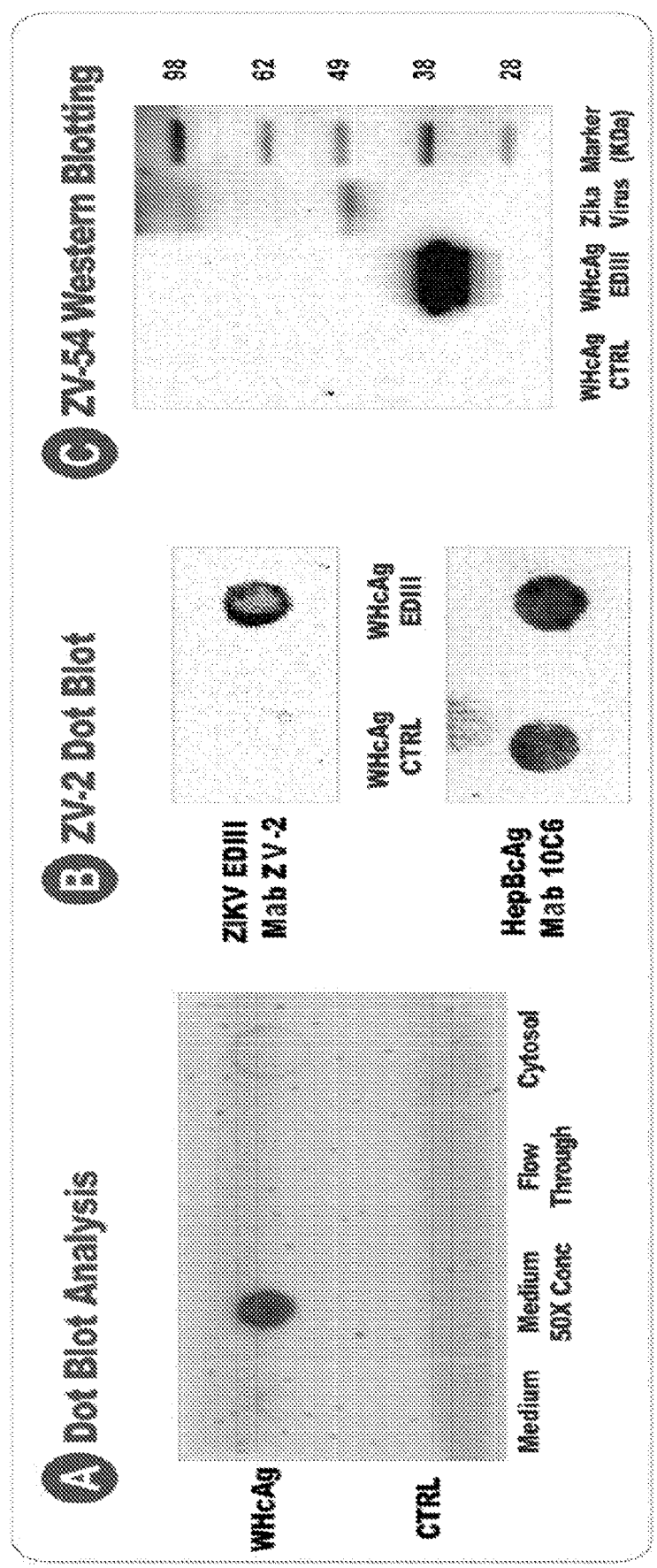
FIG. 6 illustrates dot blot and Western blot analysis showing WHcAg-ZIKV chimeric VLP production and antigenicity.
Figure 7:
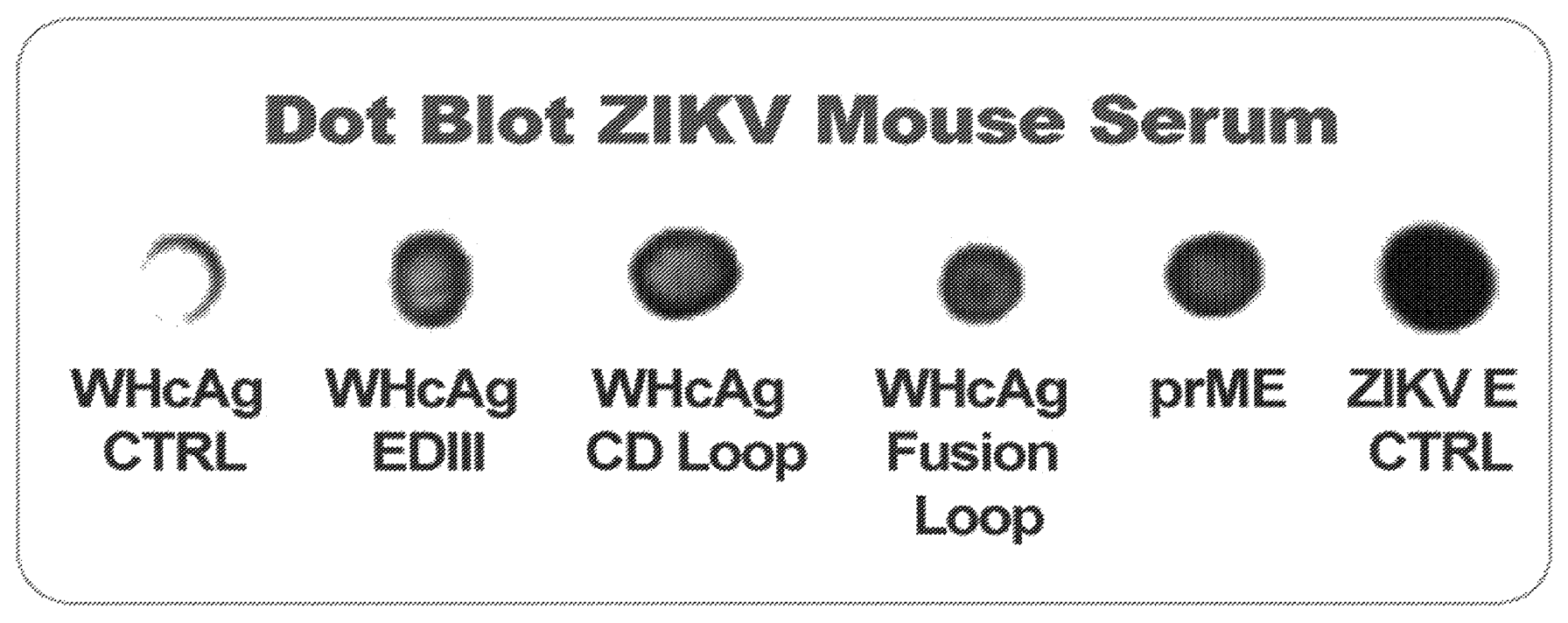
Figure 8:
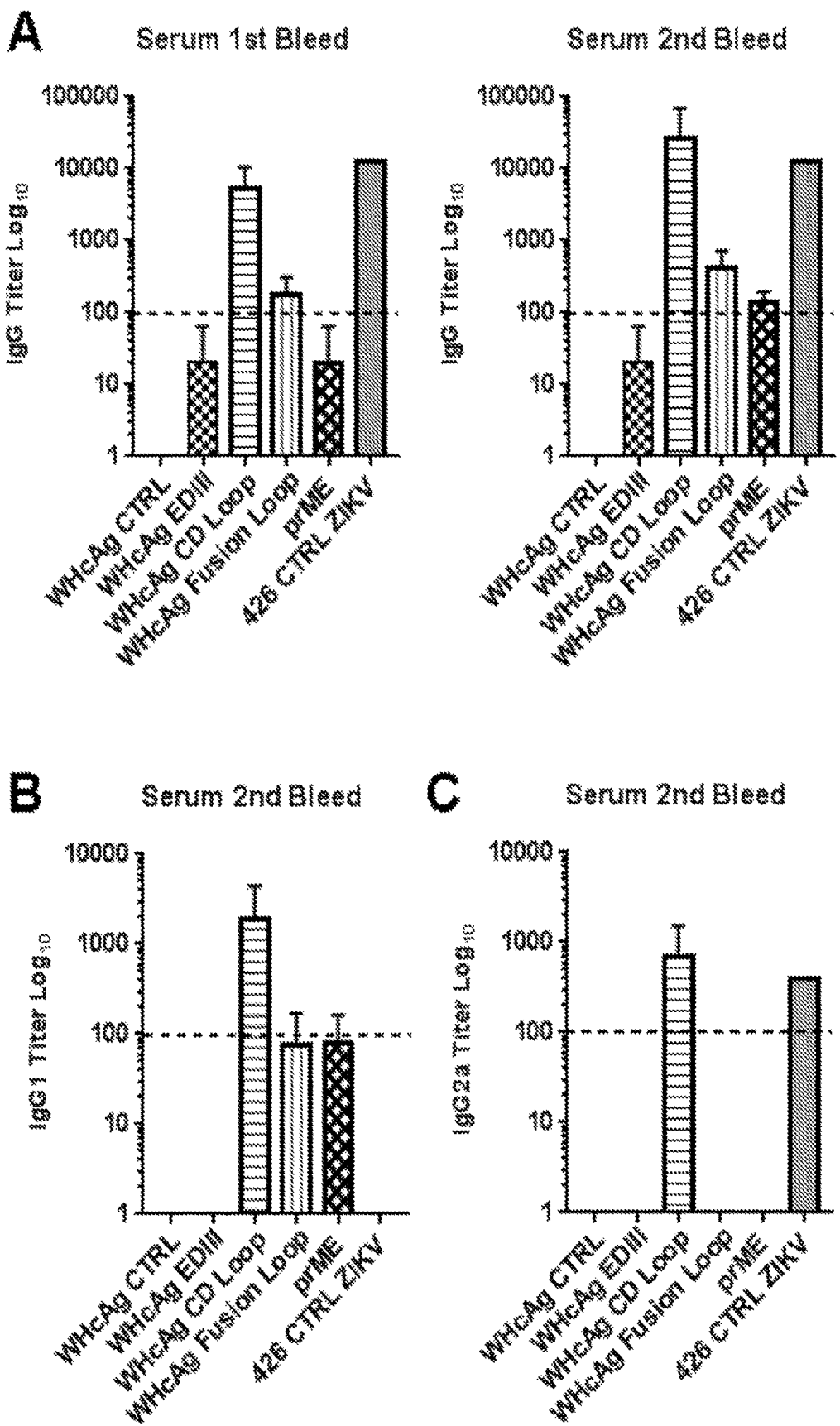
FIG. 8 illustrates ELISA analysis of mouse serum immunized with different WHcAg-ZIKV chimeric VLPs for IgG titer (A), IgG1 titer (B) and IgG2a titer (C). The limit for level of detection is 100 (dotted line).

Appropriate *Pichia* yeast strains for protein expression are available from, e.g., ATCC (e.g., *Komagataella phaffii* Kurtzman ATCC 76274™ or *Komagataella pastoris* ATCC® 76274™). Using in silico analysis, codon-optimized DNA constructs expressing the ZIKA EDIII antigens conserved between different strains were designed (FIGS. 2, 3A, and 3B). Constructs using the promoter from the *Pichia* alcohol oxidase 1 (AOX1) gene were developed to drive production of the recombinant protein (ATUM.bio). Purification of VLPs by ultracentrifugation and ultrafiltration methods and assays for quantification, purity and immunogenicity of the VLPs has been established [16]. Importantly, VLPs morphology and purity was assessed using Electron Microscopy analysis (FIG. 5). Antigenicity of VLPs was tested using Western blotting and dot blot methods using different commercially available and tested commercially available monoclonal antibodies against EDIII domain such as ZV-2 (ATCC BEI Resources NR-50414 Monoclonal Anti-Zika Virus Envelope (E) Protein) and ZV-54 (Millipore Sigma MABF2046, Anti-Zika Virus Antibody) (FIGS. 6 and 7).

Example 3

Immunizing Animals: Mouse Study

Safety is determined in the context of pregnant female BALB/c mice and in the context of 5 week old male and female mice. In both cases (n=10/concentration), three different concentrations (10 μg, 25 μg and 50 μg) of WHcAg-ZIKV chimera VLP are injected intramuscularly. As negative controls, PBS and WHcAg VLPs without Zika virus antigen are injected. To evaluate safety in the context of a prime-boost strategy, an independent set of animals (n=10/concentration) is injected at 3 weeks post the initial vaccination event with the same concentration of VLP as used in the prime vaccination. The animals are weighed daily and their morphological features and behavior (eating, drinking, mobility, social behavior) are recorded in comparison with the negative control group. Terminally sacrificed animals are necropsied to assess gross toxicity at the level of the internal organs including the spleen and the liver. The spleen tissue is banked for B-cell assays. Inflammatory load is evaluated in these animals at the end of the study. Following a terminal bleed, serum is obtained and utilized to quantify inflammatory mediators in circulation following the prime alone and the prime-boost strategy. The Aushon Multiplex Platform (Ciraplex, Aushon Biosystems) or Luminex system is used to simultaneously quantify the levels of inflammatory mediators. Such assays allow an analysis of multiple cytokines and chemokines in serum and tissue in vaccinated animals.

Figure 15:
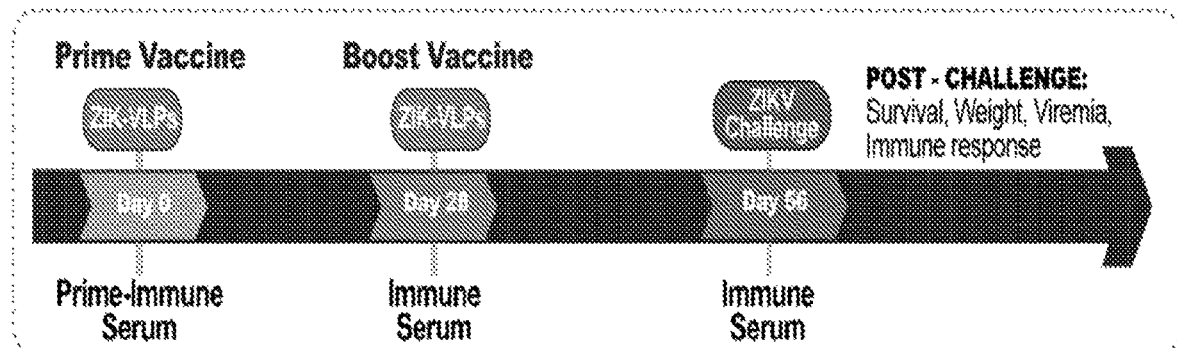
FIG. 15 shows mouse models utilized for testing efficacy, safety and protection for WHcAg-ZIKV chimera VLPs vaccine candidates.
Figure 15:
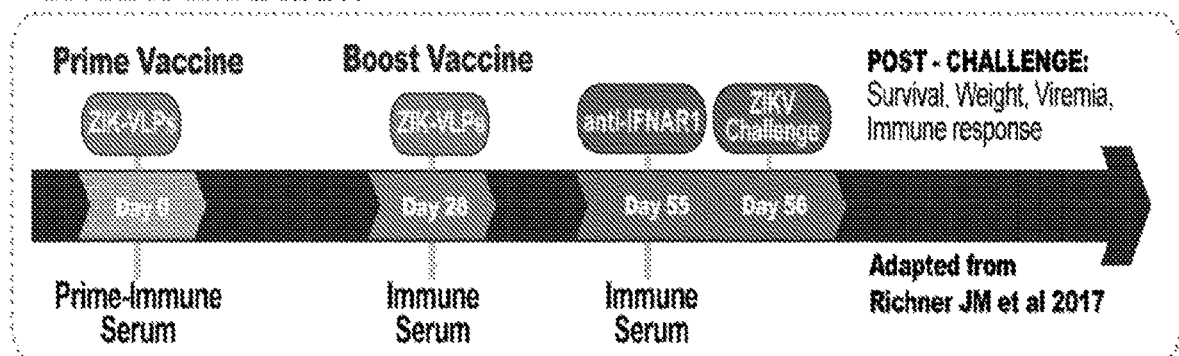

Animal studies towards characterizing the WHcAg-ZIKV chimera VLP vaccine are performed using three lethal models for ZIKV infection: i) the A129 mouse model [46]; ii) the AG129 mouse model [47]; and iii) the C57BL/6 immunocompetent mouse model treated with Anti-IFNAR1 antibody [27] (FIG. 15). The challenge experiments are carried out according to Rossi et al in AG126 mouse model: 3 week old mice are the most susceptible to ZIKV infection while 5 week old mice showed signs of disease but recovered [46]. The 5 week old mice continued to maintain detectable viral load in the serum that could be compared with the 3 week old mice. Typical vaccination strategies require at least 2-3 weeks duration for the host to mount an immune response. For the three week old mice, this requires vaccination to be carried out immediately after birth. There are uncertainties regarding robustness of the immune system in a newborn animal. To address these concerns, in the current study, the 5 week old animal are challenged with a prime immunization at week 1 after birth and a boost at week 4 after birth, followed by challenge in week 5. The A129 is an immunocompromised animal model that could be unable to recapitulate the immunization response. For this reason, the immunocompetent mouse model BALB/c treated with Anti-IFNAR1 antibody is included before ZIKV challenge. The comparison between the two models is relevant to improve immunization strategies including vaccine dosage and formulation according to [27]. The challenge experiments are conducted using Zika Virus FSS13025 Cambodia strain [46], the Puerto Rico strain (PRVABC59) and other strains available at ATCC BEI-Resources (available on the world wide web at beiresources.org). Standardized assays for the quantification of this strain by plaque assay and quantitative reverse-transcriptase polymerase chain reaction (qRT-PCR) have been developed. The prime-only, prime-boost vaccinated animals (at the maximum tolerated concentration of VLP with no apparent toxic outcomes) are challenged after vaccination by intra peritoneal challenge with a Zika virus strain (e.g., PRV-ABC59) with $1\times10^4$ plaque-forming units (PFU). The infected animals are monitored continuously for one week. If there is no protection or suboptimal protection, the animals will show symptoms of disease. The animals are monitored for signs of illness including weight loss, hunched posture and ruffled fur and for signs of severe disease including tremors, lethargy and anorexia. The mortality rate of vaccinated animals versus unvaccinated controls is quantified. At the end of the study period, survivors are sacrificed and samples collected for follow up studies. All sacrificed animals are terminally bled and serum collected. The serum is subjected to analysis of inflammatory mediators. In addition, the circulating viral load (infectious viral titers and genomic copy numbers) is quantified in all experimental and control groups. The neutralization antibody titers are determined using the serum samples by plaque reduction neutralization assay (PRNT assay). $PRNT_{50}$ and $PRNT_{80}$ titer values will be obtained by the method described in the art [16, 48]. Necropsy is conducted on all animals and spleen isolated for B cell activity studies (described below). General gross morphological examination of other internal organs including the liver is conducted. As flaviviruses, in general, demonstrate a tropism to the liver, the viral load in the liver +/− VLP is quantified.

Figure 16:
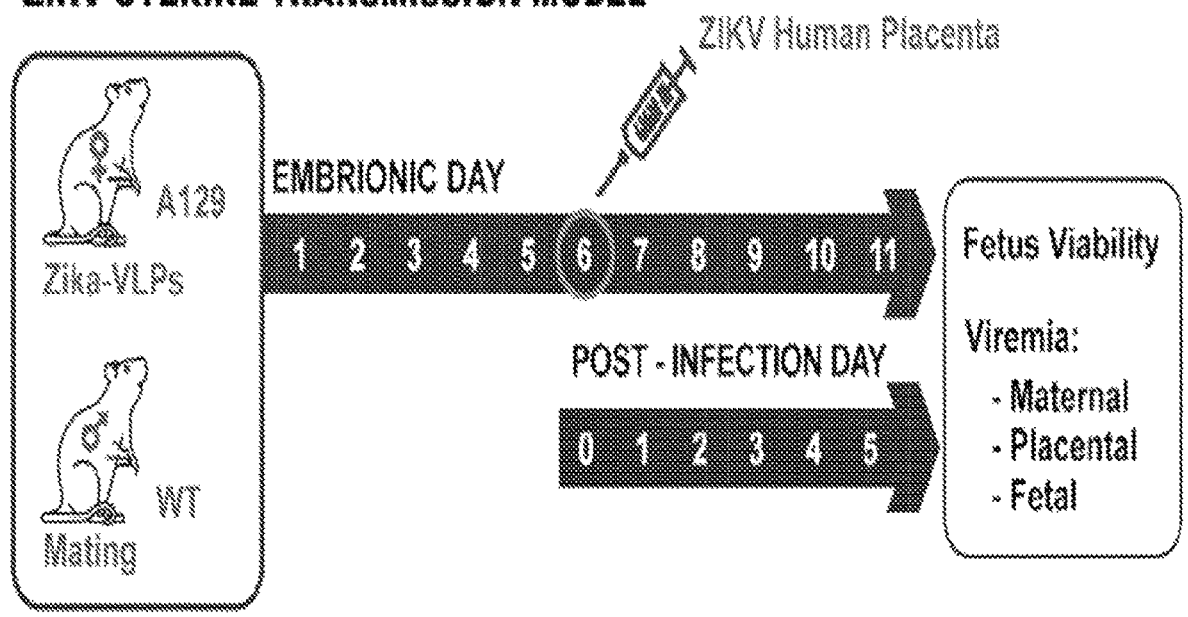
FIG. 16 shows a mouse model utilized for testing ZIKV intrauterine transmission protection by WHcAg-ZIKV chimera VLPs vaccine candidates.
Figure 17:
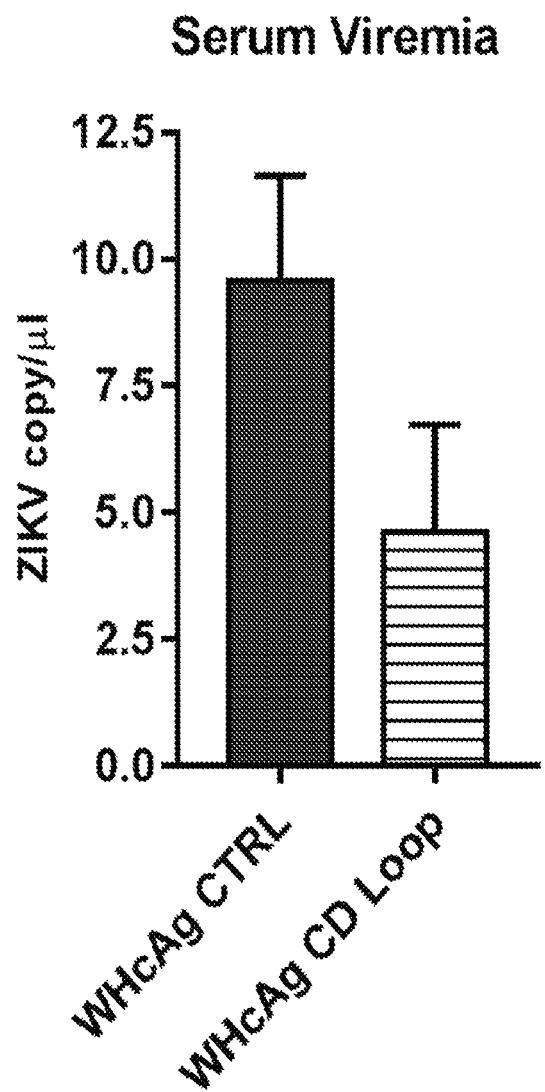
FIG. 17 shows results of experiments analyzing serum viremia in mice 3 days viral post-injection using quantitative Real-Time PCR (qRT-PCR).

A group of 5 mice were immunized twice (prime and boost) with the placebo control (WHcAg CTRL VLPs devoid Zika antigen) and the Zika vaccine candidate (WHcAg CD loop VLPs) by intramuscular injection. The VLPs dosage was 10 μg adjuvanted with squalene-based oil-inwater nano-emulsion AddaVax (InvivoGen). Boost immunization was performed 14 days after prime immunization. After 28 days the prime immunization, animals were conditioned for Zika Virus infection using the anti-IFNAR1 antibody according to the literature protocol [27], see FIG. 16. Viral infection was performed by intraperitoneal injection 1 day after anti-IFNAR1 antibody treatment, using 10,000 plaque forming units (PFU) of Zika Virus Puerto Rico strain PRVABC59 (ATCC, BEI Resources NR-50240). Serum viremia was analyzed 3 days viral post-injection using quantitative Real-Time PCR (qRT-PCR), with the instrument for Bio-Rad CFX96 Touch™, and the kit Bio-Rad iTaq Universal SYBR Green kit (Catalog #172-5151), following the manufacturer's instructions. Specific Zika PCR primers used were according to the protocol of Lanciotti, R. et al. [49]: Forward oligo 5' CCGCTGCC-CAACACAAG 3'; and Reverse oligo 5' CCACTAACGTTCTTTTGCAGACAT 3'. Quantification of viral copy number per microliter (μl) was obtained by standard curve approach using the Zika Virus (strain PRV-ABC59) genomic RNA standard (ATCC, BEI Resources NR-50244). FIG. 17 shows that ZIKV copy number was decreased in the mice receiving the Zika vaccine candidate (WHcAg CD loop VLPs).

Safety is determined in the context of pregnant female BALB/c mice and in the context of 5 week old male and female mice. In both cases (n=10/concentration), three different concentrations (10 μg, 25 μg and 50 μg) of VLP are injected intramuscularly. As negative controls, PBS and WHcAg VLPs without Zika virus antigen are injected. To evaluate safety in the context of a prime-boost strategy, an independent set of animals (n=10/concentration) is injected at 3 weeks post the initial vaccination event with the same concentration of VLP as used in the prime vaccination. The animals are weighed daily and their morphological features and behavior (eating, drinking, mobility, social behavior) are recorded in comparison with the negative control group. Terminally sacrificed animals are further necropsied to assess gross toxicity at the level of the internal organs including the spleen and the liver. The spleen tissue is banked for B-cell assays. Inflammatory load is evaluated in these animals at the end of the study. Following a terminal bleed, serum is obtained and utilized to quantify inflammatory mediators in circulation following the prime alone and the prime-boost strategy. The Aushon Multiplex Platform (Ciraplex, Aushon Biosystems) or Luminex system is used to simultaneously quantify the levels of inflammatory mediators. Such assays allow an analysis of multiple cytokines and chemokines in serum and tissue in vaccinated animals. Zika-VLP vaccine candidates are tested in a murine model for protection against fetal transmission, assessing fetal viability, morphology and viremia. The well-established model for trans-placental transmission using the A129 mouse is employed. In this model, infecting dams at embryonic day six (E6) results in placental insufficiency and fetal demise, while dams infected at midstage E9 show cranial dimension reduction. Importantly, infection at E6 results in 100% nonviable fetuses, while infection at E9 results in 90% fetal viability, 5 days after infection in both groups (see FIG. 16).

Mouse models will be useful for identify specific neutralizing antibody against Zika Virus according to the literature [38].

Example 4

Cross-Reactivity for Zika Virus Antibody and Antigen Dependent Enhancement Test

In vitro Assays for testing Antigen Dependent Enhancement (ADE) in ZIK-VLP chimera vaccinated mice are performed for testing vaccine specificity. Mouse serum from immunized animals with ZIK-VLP chimera vaccine is tested in a standard in vitro assay using U937 (ATCC® CRL-1593.2™) and K562 (ATCC® CCL-243™) lymphocyte cell-lines from ATCC according to methods known in the art. Briefly, serial dilutions of heat-inactivated sera from BALB/c mice is incubated with DENV strains for each serotypes 1 to 4, for 1 hour at 37° C. As a positive control for ADE the pan-Flavivirus antibody, clone D1-4G2-4-15 (ATCC BEI Resources, NR-50327) is also included. Serum from animals immunized with WHcAg VLPs will be used as a negative control.

The cells are incubated with the serum-virus mixture for 2 hours at 37° C. with multiplicity of infection (MOI) 3, and are washed in order to remove free viral particles. Viral titer in the culture supernatant is measured according to the art [27, 50] with standard quantitative Real-Time-PCR (qRT-PCR) after 4 days, to allow for viral replication.

Example 5

Zika Virus Diagnostic

Antibody-sandwich ELISA. Antibody-sandwich ELISA is perhaps the most useful of the immunosorbent assays for detecting antigen/antibody because it is between 2 and 5 times more sensitive than the direct/indirect ELISA in which antigen is directly bound to the solid phase. Two sets of sandwich ELISAs will be developed to 1) detect the presence of long-lasting, neutralizing anti-Zika virus antibodies (IgG), and 2) enable early detection of anti-Zika IgM in clinical samples.

To detect ZIKV antigens in sandwich ELISA format, the wells of microtitre plates are coated with antibody against the scaffolding system WHcAg in order to capture different types of WHcAg-ZIKV chimera VLPs. The ELISA plates are incubated with subject serum (human or mouse) containing anti-ZIKV antibodies. The bound conjugate is detected after addition of specific secondary antibody against IgG or IgM labeled with Horseradish Peroxidase (HRP). The detection of antibody against Zika Virus antigen is performed using HRP substrates such as TMB or ECL and a microplate reader instrument. A positive control using antibody generated against Zika Virus is included in the test, while negative controls include: WHcAg VLPs without any Zika antigen or not immunized serum against Zika. The sandwich ELISA test for human IgG is useful for the detection of circulating long-lived, neutralizing anti-Zika virus IgG. The IgM sandwich ELISA will be very effective for the early onset of the infection when IgM response peaks.

Rapid Diagnostic Detection using Lateral Flow Immunoassay (LFIA) system.

Early and accurate diagnosis of Zika Virus is very important, especially on the field. The LFIA (FIG. 13) will be used to detect anti Zika Virus antibodies in sera from clinically proven patients, as well as in healthy control subjects (FIG. 14). The lateral flow immunoassay (LFIA) is developed to detect subject serum antibody against Zika Virus Envelope and NS1 antigen. Colloidal gold particle labelled goat anti human IgG/IgM (1.0 mg/L) is used as the detector reagent. Recombinant WHcAg-ZIKV chimera VLP protein (1.0 mg/L) and rabbit anti-goat IgG (1.0 mg/L) were immobilized in test and control lines, respectively, on a nitrocellulose membrane, acting as the capture reagents. Alternatively recombinant WHcAg-ZIKV chimera VLPs can be captured on the support by immobilized antibody able to bind the WHcAg scaffolding protein.

Example 6

Developing a Formulation of VLPs

Zika VLP vaccine is manufactured according cGMP guidelines and formulated following standard FDA guidelines. The vaccine is free from adventitious agents and toxic chemicals. Formulations will include diluents, stabilizers, adjuvants and preservatives [12, 51]. The studies disclosed herein include formulation optimization in order to increase vaccine efficacy and safety.

REFERENCES

[1] G. W. Dick, Zika virus. II. Pathogenicity and physical properties, Trans R Soc Trop Med Hyg 46 (1952) 521-534.

[2] G. W. Dick, S. F. Kitchen, A. J. Haddow, Zika virus. I. Isolations and serological specificity, Trans R Soc Trop Med Hyg 46 (1952) 509-520.

[3] F. N. Macnamara, Zika virus: a report on three cases of human infection during an epidemic of jaundice in Nigeria, Trans R Soc Trop Med Hyg 48 (1954) 139-145.

[4] D. Musso, D. J. Gubler, Zika Virus, Clin Microbiol Rev 29 (2016) 487-524.

[5] C. Chang, K. Ortiz, A. Ansari, M. E. Gershwin, The Zika outbreak of the 21st century, J Autoimmun 68 (2016) 1-13.

[6] E. D'Ortenzio, S. Matheron, X. de Lamballerie, B. Hubert, G. Piorkowski, M. Maquart, D. Descamps, F. Damond, Y. Yazdanpanah, I. Leparc-Goffart, Evidence of Sexual Transmission of Zika Virus, N Engl J Med (2016).

[7] S. L. Hills, K. Russell, M. Hennessey, C. Williams, A. M. Oster, M. Fischer, P. Mead, Transmission of Zika Virus Through Sexual Contact with Travelers to Areas of Ongoing Transmission—Continental United States, 2016, MMWR Morb Mortal Wkly Rep 65 (2016) 215-216.

[8] J. J. Adibi, E. T. Marques, Jr., A. Cartus, R. H. Beigi, Teratogenic effects of the Zika virus and the role of the placenta, Lancet 387 (2016) 1587-1590.

[9] A. Likos, I. Griffin, A. M. Bingham, D. Stanek, M. Fischer, S. White, J. Hamilton, L. Eisenstein, D. Atrubin, P. Mulay, B. Scott, P. Jenkins, D. Fernandez, E. Rico, L. Gillis, R. Jean, M. Cone, C. Blackmore, J. McAllister, C. Vasquez, L. Rivera, C. Philip, Local Mosquito-Borne Transmission of Zika Virus—Miami-Dade and Broward Counties, Fla., June-August 2016, MMWR Morb Mortal Wkly Rep 65 (2016) 1032-1038.

[10] L. Adams, M. Bello-Pagan, M. Lozier, K. R. Ryff, C. Espinet, J. Torres, J. Perez-Padilla, M. F. Febo, E. Dirlikov, A. Martinez, J. Munoz-Jordan, M. Garcia, M. O. Segarra, G. Malave, A. Rivera, C. Shapiro-Mendoza, A. Rosinger, M. J. Kuehnert, K. W. Chung, L. L. Pate, A. Harris, R. R. Hemme, A. Lenhart, G. Aquino, S. Zaki, J. S. Read, S. H. Waterman, L. I. Alvarado, F. Alvarado-Ramy, M. Valencia-Prado, D. Thomas, T. M. Sharp, B. Rivera-Garcia, Update: Ongoing Zika Virus Transmission—Puerto Rico, Nov. 1, 2015-Jul. 7, 2016, MMWR Morb Mortal Wkly Rep 65 (2016) 774-779.

[11] S. A. Rasmussen, D. J. Jamieson, M. A. Honein, L. R. Petersen, Zika Virus and Birth Defects—Reviewing the Evidence for Causality, N Engl J Med (2016).

[12] V. Cimica, J. M. Galarza, Adjuvant formulations for virus-like particle (VLP) based vaccines, Clin Immunol 183 (2017) 99-108.

[13] L. Zhao, A. Seth, N. Wibowo, C. X. Zhao, N. Mitter, C. Yu, A. P. Middelberg, Nanoparticle vaccines, Vaccine 32 (2014) 327-337.

[14] F. Zabel, T. M. Kündig, M. F. Bachmann, Virus-induced humoral immunity: on how B cell responses are initiated, Current Opinion in Virology 3 (2013) 357-362.

[15] P. R. Dormitzer, G. Grandi, R. Rappuoli, Structural vaccinology starts to deliver, Nature Reviews. Microbiology 10 (2012) 807-813.

[16] V. Cimica, H. Boigard, B. Bhatia, J. T. Fallon, A. Alimova, P. Gottlieb, J. M. Galarza, A Novel Respiratory Syncytial Virus-Like Particle (VLP) Vaccine Composed of the Postfusion and Prefusion Conformations of the F Glycoprotein, Clinical and vaccine immunology: CVI (2016).

[17] S. F. Altschul, W. Gish, W. Miller, E. W. Myers, D. J. Lipman, Basic local alignment search tool, J Mol Biol 215 (1990) 403-410.

[18] L. Dai, J. Song, X. Lu, Y. Q. Deng, A. M. Musyoki, H. Cheng, Y. Zhang, Y. Yuan, H. Song, J. Haywood, H. Xiao, J. Yan, Y. Shi, C. F. Qin, J. Qi, G. F. Gao, Structures of the Zika Virus Envelope Protein and Its Complex with a Flavivirus Broadly Protective Antibody, Cell Host Microbe (2016).

[19] J. F. Conway, N. Cheng, A. Zlotnick, P. T. Wingfield, S. J. Stahl, A. C. Steven, Visualization of a 4-helix bundle in the hepatitis B virus capsid by cryo-electron microscopy, Nature 386 (1997) 91-94.

[20] F. Schodel, R. Wirtz, D. Peterson, J. Hughes, R. Warren, J. Sadoff, D. Milich, Immunity to malaria elicited by hybrid hepatitis B virus core particles carrying circumsporozoite protein epitopes, J Exp Med 180 (1994) 1037-1046.

[21] J. N. Billaud, D. Peterson, M. Barr, A. Chen, M. Sallberg, F. Garduno, P. Goldstein, W. McDowell, J. Hughes, J. Jones, D. Milich, Combinatorial approach to hepadnavirus-like particle vaccine design, J Virol 79 (2005) 13656-13666.

[22] W. C. Brown, D. L. Akey, J. R. Konwerski, J. T. Tarrasch, G. Skiniotis, R. J. Kuhn, J. L. Smith, Extended surface for membrane association in Zika virus NS1 structure, Nat Struct Mol Biol 23 (2016) 865-867.

[23] D. Sirohi, Z. Chen, L. Sun, T. Klose, T. C. Pierson, M. G. Rossmann, R. J. Kuhn, The 3.8 A resolution cryo-EM structure of Zika virus, Science (2016).

[24] Z. Shang, H. Song, Y. Shi, J. Qi, G. F. Gao, Crystal Structure of the Capsid Protein from Zika Virus, J Mol Biol 430 (2018) 948-962.

[25] I. Zlatev, M. Manoharan, J. J. Vasseur, F. Morvan, Solid-phase chemical synthesis of 5'-triphosphate DNA, RNA, and chemically modified oligonucleotides, Curr Protoc Nucleic Acid Chem Chapter 1 (2012) Unit1 28.

[26] A. Shivalingam, T. Brown, Synthesis of chemically modified DNA, Biochem Soc Trans 44 (2016) 709-715.

[27] J. M. Richner, S. Himansu, K. A. Dowd, S. L. Butler, V. Salazar, J. M. Fox, J. G. Julander, W. W. Tang, S. Shresta, T. C. Pierson, G. Ciaramella, M. S. Diamond, Modified mRNA Vaccines Protect against Zika Virus Infection, Cell 169 (2017) 176.

[28] D. Betancourt, N. M. de Queiroz, T. Xia, J. Ahn, G. N. Barber, Cutting Edge: Innate Immune Augmenting Vesicular Stomatitis Virus Expressing Zika Virus Proteins Confers Protective Immunity, J Immunol 198 (2017) 3023-3028.

[29] F. Falugi, R. Petracca, M. Mariani, E. Luzzi, S. Mancianti, V. Carinci, M. L. Melli, O. Finco, A. Wack, A. Di Tommaso, M. T. De Magistris, P. Costantino, G. Del Giudice, S. Abrignani, R. Rappuoli, G. Grandi, Rationally designed strings of promiscuous CD4(+) T cell epitopes provide help to *Haemophilus influenzae* type b oligosaccharide: a model for new conjugate vaccines, Eur J Immunol 31 (2001) 3816-3824.

[30] S. Demotz, C. Barbey, G. Corradin, A. Amoroso, A. Lanzavecchia, The set of naturally processed peptides displayed by DR molecules is tuned by polymorphism of residue 86, Eur J Immunol 23 (1993) 425-432.

[31] B. M. Diethelm-Okita, D. K. Okita, L. Banaszak, B. M. Conti-Fine, Universal epitopes for human CD4+ cells on tetanus and diphtheria toxins, J Infect Dis 181 (2000) 1001-1009.

[32] J. Hammer, P. Valsasnini, K. Tolba, D. Bolin, J. Higelin, B. Takacs, F. Sinigaglia, Promiscuous and allele-specific anchors in HLA-DR-binding peptides, Cell 74 (1993) 197-203.

[33] J. L. Greenstein, V. C. Schad, W. H. Goodwin, A. B. Brauer, B. K. Bollinger, R. D. Chin, M. C. Kuo, A universal T cell epitope-containing peptide from hepatitis B surface antigen can enhance antibody specific for HIV gp120, J Immunol 148 (1992) 3970-3977.

[34] J. Alexander, M. F. del Guercio, A. Maewal, L. Qiao, J. Fikes, R. W. Chesnut, J. Paulson, D. R. Bundle, S. DeFrees, A. Sette, Linear PADRE T helper epitope and carbohydrate B cell epitope conjugates induce specific high titer IgG antibody responses, J Immunol 164 (2000) 1625-1633.

[35] N. K. Dakappagari, J. Pyles, R. Parihar, W. E. Carson, D. C. Young, P. T. Kaumaya, A chimeric multi-human epidermal growth factor receptor-2 B cell epitope peptide vaccine mediates superior antitumor responses, J Immunol 170 (2003) 4242-4253.

[36] T. C. Pierson, B. S. Graham, Zika Virus: Immunity and Vaccine Development, Cell (2016).

[37] V. A. Kostyuchenko, E. X. Lim, S. Zhang, G. Fibriansah, T. S. Ng, J. S. Ooi, J. Shi, S. M. Lok, Structure of the thermally stable Zika virus, Nature (2016).

[38] H. Zhao, E. Fernandez, K. A. Dowd, S. D. Speer, D. J. Platt, M. J. Gorman, J. Govero, C. A. Nelson, T. C. Pierson, M. S. Diamond, D. H. Fremont, Structural Basis of Zika Virus-Specific Antibody Protection, Cell 166 (2016) 1016-1027.

[39] G. Fibriansah, S. M. Lok, The development of therapeutic antibodies against dengue virus, Antiviral Res 128 (2016) 7-19.

[40] L. Priyamvada, K. M. Quicke, W. H. Hudson, N. Onlamoon, J. Sewatanon, S. Edupuganti, K. Pattanapanyasat, K. Chokephaibulkit, M. J. Mulligan, P. C. Wilson, R. Ahmed, M. S. Suthar, J. Wrammert, Human antibody responses after dengue virus infection are highly cross-reactive to Zika virus, Proc Natl Acad Sci USA (2016).

[41] W. Dejnirattisai, P. Supasa, W. Wongwiwat, A. Rouvinski, G. Barba-Spaeth, T. Duangchinda, A. Sakuntabhai, V. M. Cao-Lormeau, P. Malasit, F. A. Rey, J. Mongkolsapaya, G. R. Screaton, Dengue virus sero-cross-reactivity drives antibody-dependent enhancement of infection with zika virus, Nat Immunol 17 (2016) 1102-1108.

[42] M. Tan, X. Jiang, Subviral particle as vaccine and vaccine platform, Current Opinion in Virology 6 (2014) 24-33.

[43] K. Roose, S. De Baets, B. Schepens, X. Saelens, Hepatitis B core-based virus-like particles to present heterologous epitopes, Expert Rev Vaccines 12 (2013) 183-198.

[44] J. H. Schickli, D. C. Whitacre, R. S. Tang, J. Kaur, H. Lawlor, C. J. Peters, J. E. Jones, D. L. Peterson, M. P. McCarthy, G. Van Nest, D. R. Milich, Palivizumab epitope-displaying virus-like particles protect rodents from RSV challenge, J Clin Invest 125 (2015) 1637-1647.

[45] D. C. Whitacre, B. O. Lee, D. R. Milich, Use of hepadnavirus core proteins as vaccine platforms, Expert Rev Vaccines 8 (2009) 1565-1573.

[46] S. L. Rossi, R. B. Tesh, S. R. Azar, A. E. Muruato, K. A. Hanley, A. J. Auguste, R. M. Langsjoen, S. Paessler, N. Vasilakis, S. C. Weaver, Characterization of a Novel Murine Model to Study Zika Virus, Am J Trop Med Hyg 94 (2016) 1362-1369.

[47] M. T. Aliota, E. A. Caine, E. C. Walker, K. E. Larkin, E. Camacho, J. E. Osorio, Characterization of Lethal Zika Virus Infection in AG129 Mice, PLoS Negl Trop Dis 10 (2016) e0004682.

[48] A. B. Kawiecki, R. C. Christofferson, Zika Virus-Induced Antibody Response Enhances Dengue Virus Serotype 2 Replication In Vitro, J Infect Dis 214 (2016) 1357-1360.

[49] R. S. Lanciotti, O. L. Kosoy, J. J. Laven, J. O. Velez, A. J. Lambert, A. J. Johnson, S. M. Stanfield, M. R. Duffy, Genetic and serologic properties of Zika virus associated with an epidemic, Yap State, Micronesia, 2007, Emerg Infect Dis 14 (2008) 1232-1239.

[50] H. Boigard, A. Alimova, G. R. Martin, A. Katz, P. Gottlieb, J. M. Galarza, Zika virus-like particle (VLP) based vaccine, PLoS Negl Trop Dis 11 (2017) e0005608.

[51] N. K. Jain, N. Sahni, O. S. Kumru, S. B. Joshi, D. B. Volkin, C. Russell Middaugh, Formulation and stabilization of recombinant protein based virus-like particle vaccines, Adv Drug Deliv Rev 93 (2015) 42-55.

What is claimed is:

1. A chimeric peptide comprising a first peptide selected from SEQ ID NOS: 2-11, 22-33, 46, 47, 50 and 51 operably linked to a second heterologous peptide having an amino acid sequence that is at least 80% identical to a Woodchuck Hepatitis core Antigen protein (WHcAg) comprising an amino acid sequence of SEQ ID NO: 1 or a functional fragment thereof.

2. The chimeric peptide of claim 1 wherein the first peptide replaces amino acids from positions 77 to 82 of SEQ ID NO: 1 or functional fragments thereof.

3. The chimeric peptide according to claim 1 further including at least one peptide linker of 1-10 amino acids linking the first peptide to the sequence that is at least 90% identical to a WHcAg protein.

4. A polynucleotide comprising a nucleotide sequence encoding the chimeric peptide of claim 1.

5. An expression vector comprising the polynucleotide of claim 4 operably linked to an expression control sequence.

6. A recombinant host cell comprising the expression vector of claim 5.

7. The recombinant host cell of claim 6, wherein the host cell is:
(i) a eukaryotic cell selected from the group consisting of mammalian, yeast, insect, plant, amphibian and avian cells; or
(ii) a prokaryotic cell.

8. A virus like particle (VLP) comprising the chimeric peptide of claim 1.

9. The VLP according to claim 8, attached to a solid support microbead, an assay plate, a test strip, or a filter.

10. An antigenic composition comprising the VLP of claim 8, wherein the VLP is present in the composition at a concentration of about 0.1-2000 μg/ml, in a pharmaceutically acceptable carrier, diluent, stabilizer, preservative, or adjuvant, said composition inducing one or more of a protective immune response, production of anti-Zika neutralizing antibody, and production of anti-Zika protective antibody.

11. An antigenic composition comprising the VLP of claim 8 in a pharmaceutically acceptable carrier, diluent, stabilizer, preservative, or adjuvant, said composition comprising SEQ ID NO: 15.

12. The antigenic composition of claim 11, comprising one or more VLPs comprising different sequences selected from the group consisting of amino acid sequences at least 80% identical to SEQ ID NOs: 2-4, 6-11, 22-33, 46-47, or 50-51.

13. A composition comprising the vector of claim 5 in a pharmaceutically acceptable carrier, diluent, stabilizer, preservative, or adjuvant.

14. The composition of claim 13, comprising an adjuvant.

15. A kit comprising the VLP of claim 8 packaged with at least one reagent selected from an enzyme substrate, a detection antibody, and a blocking buffer.

16. A vaccine comprising the antigenic composition of claim 11, and an adjuvant.

17. A method of producing an immune response to a Zika virus in a subject, comprising administering to the subject an effective amount of the antigenic composition of claim 11, thereby producing an immune response to a Zika virus in the subject.

18. A method of inhibiting Zika virus infection in a subject comprising administering to the subject an effective amount of the vaccine of claim 16, thereby preventing a disease or disorder caused by a Zika virus infection in the subject.

19. The method of claim 18, wherein the administering is vaginal or nasal mucosal administration.

20. A method of detecting or measuring antibodies to Zika virus in a biological sample comprising:

a) contacting the VLP of claim 8 with a biological sample under conditions suitable for the formation of an antigen-antibody complex; and
b) measuring or detecting antibodies to Zika virus by detecting or measuring an antigen-antibody complex formed between antibodies in the biological sample and the VLP.

* * * * *

SEQUENCE LISTING

<160> NUMBER OF SEQ ID NOS: 106

<210> SEQ ID NO 1
<211> LENGTH: 188
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Woodchuck hepatitis core antigen (WHcAg)

<400> SEQUENCE: 1

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Ala Asn Cys
            180                 185
```

<210> SEQ ID NO 2
<211> LENGTH: 136
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3 full length

<400> SEQUENCE: 2

```
His Leu Lys Cys Arg Leu Lys Met Asp Lys Leu Arg Leu Lys Gly Val
1               5                   10                  15

Ser Tyr Ser Leu Cys Thr Ala Ala Phe Thr Phe Thr Lys Ile Pro Ala
            20                  25                  30

Glu Thr Leu His Gly Thr Val Thr Val Glu Val Gln Tyr Ala Gly Thr
        35                  40                  45

Asp Gly Pro Cys Lys Val Pro Ala Gln Met Ala Val Asp Met Gln Thr
    50                  55                  60

Leu Thr Pro Val Gly Arg Leu Ile Thr Ala Asn Pro Val Ile Thr Glu
65                  70                  75                  80

Ser Thr Glu Asn Ser Lys Met Met Leu Glu Leu Asp Pro Pro Phe Gly
                85                  90                  95

Asp Ser Tyr Ile Val Ile Gly Val Gly Glu Lys Lys Ile Thr His His
            100                 105                 110

Trp His Arg Ser Gly Ser Thr Ile Gly Lys Ala Phe Glu Ala Thr Val
        115                 120                 125

Arg Gly Ala Lys Arg Met Ala Val
    130                 135
```

<210> SEQ ID NO 3

<211> LENGTH: 80
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3 G (EDIII) G loop-truncated

<400> SEQUENCE: 3

```
Ala Phe Thr Phe Thr Lys Ile Pro Ala Glu Thr Leu His Gly Thr Val
1               5                   10                  15

Thr Val Glu Leu Gln Tyr Ala Gly Thr Asp Gly Pro Cys Lys Val Pro
            20                  25                  30

Ala Gln Met Ala Val Asp Met Gln Thr Leu Thr Pro Val Gly Arg Leu
        35                  40                  45

Ile Thr Ala Asn Pro Val Ile Thr Glu Ser Thr Glu Asn Ser Lys Met
    50                  55                  60

Met Leu Glu Leu Asp Pro Pro Phe Gly Asp Ser Tyr Ile Val Ile Gly
65                  70                  75                  80
```

<210> SEQ ID NO 4
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3, A-B loop

<400> SEQUENCE: 4

```
Ala Phe Thr Phe Thr Lys Ile Pro Ala Glu Thr Leu His Gly Thr Val
1               5                   10                  15

Thr Val Glu Leu Gln Tyr Ala
            20
```

<210> SEQ ID NO 5
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3, CXCDDX loop

<400> SEQUENCE: 5

```
Pro Cys Lys Val Pro Ala Gln Met Ala Val Asp Met Gln Thr Leu Thr
1               5                   10                  15

Pro Val Gly Arg Leu Ile Thr Ala Asn Pro Val Ile Thr
            20                  25
```

<210> SEQ ID NO 6
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3,  DX-E loop

<400> SEQUENCE: 6

```
Arg Leu Ile Thr Ala Asn Pro Val Ile Thr Glu Ser Thr Glu Asn Ser
1               5                   10                  15
```

Lys Met Met Leu Glu Leu Asp Pro
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 3, F-G loop

<400> SEQUENCE: 7

Gly Asp Ser Tyr Ile Val Ile Gly Val Gly Glu Lys Lys Ile Thr His
1               5                   10                  15

His Trp His Arg
            20

<210> SEQ ID NO 8
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope fusion loop

<400> SEQUENCE: 8

Asp Arg Gly Trp Gly Asn Gly Cys Gly Leu Phe Gly Lys
1               5                   10

<210> SEQ ID NO 9
<211> LENGTH: 92
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 2 (ED2) sequence A-E

<400> SEQUENCE: 9

Thr Thr Thr Val Ser Asn Met Ala Glu Val Arg Ser Tyr Cys Tyr Glu
1               5                   10                  15

Ala Ser Ile Ser Asp Met Ala Ser Asp Ser Arg Cys Pro Thr Gln Gly
            20                  25                  30

Glu Ala Tyr Leu Asp Lys Gln Ser Asp Thr Gln Tyr Val Cys Lys Arg
        35                  40                  45

<223> OTHER INFORMATION: Envelope domain 2 sequence B-D

<400> SEQUENCE: 10

```
Glu Ala Ser Ile Ser Asp Met Ala Ser Asp Ser Arg Cys Pro Thr Gln
1               5                   10                  15

Gly Glu Ala Tyr Leu Asp Lys Gln Ser Asp Thr Gln Tyr Val Cys Lys
                20                  25                  30

Arg Thr Leu Val Asp Arg Gly Trp Gly Asn Gly Cys Gly Leu Phe Gly
            35                  40                  45

Lys Gly Ser Leu Val Thr Cys Ala Lys Phe Ala Cys Ser
        50                  55                  60
```

<210> SEQ ID NO 11
<211> LENGTH: 82
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Envelope domain 1 glycan loop

<400> SEQUENCE: 11

```
Met Thr Gly Lys Ser Ile Gln Pro Glu Asn Leu Glu Tyr Arg Ile Met
1               5                   10                  15

Leu Ser Val His Gly Ser Gln His Ser Gly Met Ile Val Asn Asp Thr
                20                  25                  30

Gly His Glu Thr Asp Glu Asn Arg Ala Lys Val Glu Ile Thr Pro Asn
            35                  40                  45

Ser Pro Arg Ala Glu Ala Thr Leu Gly Gly Phe Gly Ser Leu Gly Leu
        50                  55                  60

Asp Cys Glu Pro Arg Thr Gly Leu Asp Phe Ser Asp Leu Tyr Tyr Leu
65                  70                  75                  80

Thr Met
```

<210> SEQ ID NO 12
<211> LENGTH: 327
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 2

<400> SEQUENCE: 12

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
        50                  55                  60

Leu Thr Lys Leu Ile Ala Trp Met Ser Ser Asn Ile Gly Gly Gly
65                  70                  75                  80

Thr His Leu Lys Cys Arg Leu Lys Met Asp Lys Leu Arg Leu Lys Gly
                85                  90                  95

Val Ser Tyr Ser Leu Cys Thr Ala Ala Phe Thr Phe Thr Lys Ile Pro
                100                 105                 110
```

Ala Glu Thr Leu His Gly Thr Val Thr Val Glu Val Gln Tyr Ala Gly
            115                 120                 125

Thr Asp Gly Pro Cys Lys Val Pro Ala Gln Met Ala Val Asp Met Gln
        130                 135                 140

Thr Leu Thr Pro Val Gly Arg Leu Ile Thr Ala Asn Pro Val Ile Thr
145                 150                 155                 160

Glu Ser Thr Glu Asn Ser Lys Met Met Leu Glu Leu Asp Pro Pro Phe
                165                 170                 175

Gly Asp Ser Tyr Ile Val Ile Gly Val Gly Glu Lys Lys Ile Thr His
            180                 185                 190

His Trp His Arg Ser Gly Ser Thr Ile Gly Lys Ala Phe Glu Ala Thr
        195                 200                 205

Val Arg Gly Ala Lys Arg Met Ala Val Gly Gly Gly Thr Ile Ile
            210                 215                 220

Val Asn His Val Asn Asp Thr Trp Gly Leu Lys Val Arg Gln Ser Leu
225                 230                 235                 240

Trp Phe His Leu Ser Cys Leu Thr Phe Gly Gln His Thr Val Gln Glu
                245                 250                 255

Phe Leu Val Ser Phe Gly Val Trp Ile Arg Thr Pro Ala Pro Tyr Arg
            260                 265                 270

Pro Pro Asn Ala Pro Ile Leu Ser Thr Leu Pro Glu His Thr Val Ile
        275                 280                 285

Arg Arg Arg Gly Gly Ala Arg Ala Ser Arg Ser Pro Arg Arg Arg Thr
290                 295                 300

Pro Ser Pro Arg Arg Arg Arg Ser Gln Ser Pro Arg Arg Arg Arg Ser
305                 310                 315                 320

Gln Ser Pro Ser Ala Asn Cys
                325

<210> SEQ ID NO 13
<211> LENGTH: 262
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 3

<400> SEQUENCE: 13

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Ala Phe Thr Phe
65                  70                  75                  80

Thr Lys Ile Pro Ala Glu Thr Leu His Gly Thr Val Thr Val Glu Leu
                85                  90                  95

Gln Tyr Ala Gly Thr Asp Gly Pro Cys Lys Val Pro Ala Gln Met Ala
            100                 105                 110

Val Asp Met Gln Thr Leu Thr Pro Val Gly Arg Leu Ile Thr Ala Asn
        115                 120                 125

```
Pro Val Ile Thr Glu Ser Thr Glu Asn Ser Lys Met Met Leu Glu Leu
    130                 135                 140

Asp Pro Pro Phe Gly Asp Ser Tyr Ile Val Ile Gly Thr Ile Ile Val
145                 150                 155                 160

Asn His Val Asn Asp Thr Trp Gly Leu Lys Val Arg Gln Ser Leu Trp
                165                 170                 175

Phe His Leu Ser Cys Leu Thr Phe Gly Gln His Thr Val Gln Glu Phe
            180                 185                 190

Leu Val Ser Phe Gly Val Trp Ile Arg Thr Pro Ala Pro Tyr Arg Pro
        195                 200                 205

Pro Asn Ala Pro Ile Leu Ser Thr Leu Pro Glu His Thr Val Ile Arg
    210                 215                 220

Arg Arg Gly Gly Ala Arg Ala Ser Arg Ser Pro Arg Arg Arg Thr Pro
225                 230                 235                 240

Ser Pro Arg Arg Arg Ser Gln Ser Pro Arg Arg Arg Arg Ser Gln
                245                 250                 255

Ser Pro Ser Ala Asn Cys
            260

<210> SEQ ID NO 14
<211> LENGTH: 205
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 4

<400> SEQUENCE: 14

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Ala Phe Thr Phe
65                  70                  75                  80

Thr Lys Ile Pro Ala Glu Thr Leu His Gly Thr Val Thr Val Glu Leu
                85                  90                  95

Gln Tyr Ala Thr Ile Ile Val Asn His Val Asn Asp Thr Trp Gly Leu
            100                 105                 110

Lys Val Arg Gln Ser Leu Trp Phe His Leu Ser Cys Leu Thr Phe Gly
        115                 120                 125

Gln His Thr Val Gln Glu Phe Leu Val Ser Phe Gly Val Trp Ile Arg
    130                 135                 140

Thr Pro Ala Pro Tyr Arg Pro Pro Asn Ala Pro Ile Leu Ser Thr Leu
145                 150                 155                 160

Pro Glu His Thr Val Ile Arg Arg Arg Gly Gly Ala Arg Ala Ser Arg
                165                 170                 175

Ser Pro Arg Arg Arg Thr Pro Ser Pro Arg Arg Arg Arg Ser Gln Ser
            180                 185                 190

Pro Arg Arg Arg Arg Ser Gln Ser Pro Ser Ala Asn Cys
        195                 200                 205
```

<210> SEQ ID NO 15
<211> LENGTH: 211
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 5

<400> SEQUENCE: 15

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Pro Cys Lys Val
65                  70                  75                  80

Pro Ala Gln Met Ala Val Asp Met Gln Thr Leu Thr Pro Val Gly Arg
                85                  90                  95

Leu Ile Thr Ala Asn Pro Val Ile Thr Thr Ile Ile Val Asn His Val
            100                 105                 110

Asn Asp Thr Trp Gly Leu Lys Val Arg Gln Ser Leu Trp Phe His Leu
        115                 120                 125

Ser Cys Leu Thr Phe Gly Gln His Thr Val Gln Glu Phe Leu Val Ser
    130                 135                 140

Phe Gly Val Trp Ile Arg Thr Pro Ala Pro Tyr Arg Pro Pro Asn Ala
145                 150                 155                 160

Pro Ile Leu Ser Thr Leu Pro Glu His Thr Val Ile Arg Arg Arg Gly
                165                 170                 175

Gly Ala Arg Ala Ser Arg Ser Pro Arg Arg Arg Thr Pro Ser Pro Arg
            180                 185                 190

Arg Arg Arg Ser Gln Ser Pro Arg Arg Arg Ser Gln Ser Pro Ser
        195                 200                 205

Ala Asn Cys
    210

<210> SEQ ID NO 16
<211> LENGTH: 206
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 6

<400> SEQUENCE: 16

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu

```
                    50                  55                  60
Leu Thr Lys Leu Ile Ala Trp Met Ser Ser Asn Ile Arg Leu Ile Thr
 65                  70                  75                  80

Ala Asn Pro Val Ile Thr Glu Ser Thr Glu Asn Ser Lys Met Met Leu
                     85                  90                  95

Glu Leu Asp Pro Thr Ile Ile Val Asn His Val Asn Asp Thr Trp Gly
                100                 105                 110

Leu Lys Val Arg Gln Ser Leu Trp Phe His Leu Ser Cys Leu Thr Phe
                115                 120                 125

Gly Gln His Thr Val Gln Glu Phe Leu Val Ser Phe Gly Val Trp Ile
                130                 135                 140

Arg Thr Pro Ala Pro Tyr Arg Pro Pro Asn Ala Pro Ile Leu Ser Thr
145                 150                 155                 160

Leu Pro Glu His Thr Val Ile Arg Arg Arg Gly Gly Ala Arg Ala Ser
                165                 170                 175

Arg Ser Pro Arg Arg Arg Thr Pro Ser Pro Arg Arg Arg Arg Ser Gln
                180                 185                 190

Ser Pro Arg Arg Arg Arg Ser Gln Ser Pro Ser Ala Asn Cys
                195                 200                 205

<210> SEQ ID NO 17
<211> LENGTH: 202
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 7

<400> SEQUENCE: 17

Met Asp Ile Asp Pro Tyr Lys Glu Phe Gly Ser Ser Tyr Gln Leu Leu
  1                   5                  10                  15

Asn Phe Leu Pro Leu Asp Phe Phe Pro Asp Leu Asn Ala Leu Val Asp
                 20                  25                  30

Thr Ala Thr Ala Leu Tyr Glu Glu Glu Leu Thr Gly Arg Glu His Cys
             35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Gly Asp Ser Tyr
 65                  70                  75                  80

Ile Val Ile Gly Val Gly Glu Lys Lys Ile Thr His His Trp His Arg
                 85                  90                  95

Thr Ile Ile Val Asn His Val Asn Asp Thr Trp Gly Leu Lys Val Arg
                100                 105                 110

Gln Ser Leu Trp Phe His Leu Ser Cys Leu Thr Phe Gly Gln His Thr
            115                 120                 125

Val Gln Glu Phe Leu Val Ser Phe Gly Val Trp Ile Arg Thr Pro Ala
            130                 135                 140

Pro Tyr Arg Pro Pro Asn Ala Pro Ile Leu Ser Thr Leu Pro Glu His
145                 150                 155                 160

Thr Val Ile Arg Arg Arg Gly Gly Ala Arg Ala Ser Arg Ser Pro Arg
                165                 170                 175

Arg Arg Thr Pro Ser Pro Arg Arg Arg Ser Gln Ser Pro Arg Arg
                180                 185                 190

Arg Arg Ser Gln Ser Pro Ser Ala Asn Cys
```

<210> SEQ ID NO 18
<211> LENGTH: 200
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 8

<400> SEQUENCE: 18

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
        50                  55                  60

Leu Thr Lys Leu Ile Ala Trp Met Ser Ser Asn Ile Gly Gly Thr Asp
65                  70                  75                  80

Arg Gly Trp Gly Asn Gly Cys Gly Leu Phe Gly Lys Gly Thr Ile
                85                  90                  95

Ile Val Asn His Val Asn Asp Thr Trp Gly Leu Lys Val Arg Gln Ser
                100                 105                 110

Leu Trp Phe His Leu Ser Cys Leu Thr Phe Gly Gln His Thr Val Gln
            115                 120                 125

Glu Phe Leu Val Ser Phe Gly Val Trp Ile Arg Thr Pro Ala Pro Tyr
        130                 135                 140

Arg Pro Pro Asn Ala Pro Ile Leu Ser Thr Leu Pro Glu His Thr Val
145                 150                 155                 160

Ile Arg Arg Arg Gly Gly Ala Arg Ala Ser Arg Ser Pro Arg Arg Arg
                165                 170                 175

Thr Pro Ser Pro Arg Arg Arg Ser Gln Ser Pro Arg Arg Arg Arg
            180                 185                 190

Ser Gln Ser Pro Ser Ala Asn Cys
        195                 200
```

<210> SEQ ID NO 19
<211> LENGTH: 278
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 9

<400> SEQUENCE: 19

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
        50                  55                  60
```

```
Leu Thr Lys Leu Ile Ala Trp Met Ser Ser Asn Ile Gly Gly Thr Thr
 65                  70                  75                  80

Thr Val Ser Asn Met Ala Glu Val Arg Ser Tyr Cys Tyr Glu Ala Ser
                 85                  90                  95

Ile Ser Asp Met Ala Ser Asp Ser Arg Cys Pro Thr Gln Gly Glu Ala
            100                 105                 110

Tyr Leu Asp Lys Gln Ser Asp Thr Gln Tyr Val Cys Lys Arg Thr Leu
            115                 120                 125

Val Asp Arg Gly Trp Gly Asn Gly Cys Gly Leu Phe Gly Lys Gly Ser
        130                 135                 140

Leu Val Thr Cys Ala Lys Phe Ala Cys Ser Lys Lys Met Thr Gly Lys
145                 150                 155                 160

Ser Ile Gln Pro Glu Asn Leu Glu Tyr Arg Gly Gly Thr Ile Ile Val
                165                 170                 175

Asn His Val Asn Asp Thr Trp Gly Leu Lys Val Arg Gln Ser Leu Trp
            180                 185                 190

Phe His Leu Ser Cys Leu Thr Phe Gly Gln His Thr Val Gln Glu Phe
        195                 200                 205

Leu Val Ser Phe Gly Val Trp Ile Arg Thr Pro Ala Pro Tyr Arg Pro
210                 215                 220

Pro Asn Ala Pro Ile Leu Ser Thr Leu Pro Glu His Thr Val Ile Arg
225                 230                 235                 240

Arg Arg Gly Gly Ala Arg Ala Ser Arg Ser Pro Arg Arg Arg Thr Pro
                245                 250                 255

Ser Pro Arg Arg Arg Ser Gln Ser Pro Arg Arg Arg Ser Gln
            260                 265                 270

Ser Pro Ser Ala Asn Cys
        275

<210> SEQ ID NO 20
<211> LENGTH: 247
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 10

<400> SEQUENCE: 20

Met Asp Ile Asp Pro Tyr Lys Glu Phe Gly Ser Ser Tyr Gln Leu Leu
 1               5                  10                  15

Asn Phe Leu Pro Leu Asp Phe Pro Asp Leu Asn Ala Leu Val Asp
                 20                  25                  30

Thr Ala Thr Ala Leu Tyr Glu Glu Leu Thr Gly Arg Glu His Cys
             35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Gly Gly Glu Ala
 65                  70                  75                  80

Ser Ile Ser Asp Met Ala Ser Asp Ser Arg Cys Pro Thr Gln Gly Glu
                 85                  90                  95

Ala Tyr Leu Asp Lys Gln Ser Asp Thr Gln Tyr Val Cys Lys Arg Thr
            100                 105                 110

Leu Val Asp Arg Gly Trp Gly Asn Gly Cys Gly Leu Phe Gly Lys Gly
        115                 120                 125
```

```
Ser Leu Val Thr Cys Ala Lys Phe Ala Cys Ser Gly Gly Thr Ile Ile
    130                 135                 140

Val Asn His Val Asn Asp Thr Trp Gly Leu Lys Val Arg Gln Ser Leu
145                 150                 155                 160

Trp Phe His Leu Ser Cys Leu Thr Phe Gly Gln His Thr Val Gln Glu
                165                 170                 175

Phe Leu Val Ser Phe Gly Val Trp Ile Arg Thr Pro Ala Pro Tyr Arg
                180                 185                 190

Pro Pro Asn Ala Pro Ile Leu Ser Thr Leu Pro Glu His Thr Val Ile
                195                 200                 205

Arg Arg Arg Gly Gly Ala Arg Ala Ser Arg Ser Pro Arg Arg Arg Thr
            210                 215                 220

Pro Ser Pro Arg Arg Arg Ser Gln Ser Pro Arg Arg Arg Arg Arg Ser
225                 230                 235                 240

Gln Ser Pro Ser Ala Asn Cys
                245

<210> SEQ ID NO 21
<211> LENGTH: 268
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO: 11

<400> SEQUENCE: 21

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Met Thr
65                  70                  75                  80

Gly Lys Ser Ile Gln Pro Glu Asn Leu Glu Tyr Arg Ile Met Leu Ser
                85                  90                  95

Val His Gly Ser Gln His Ser Gly Met Ile Val Asn Asp Thr Gly His
                100                 105                 110

Glu Thr Asp Glu Asn Arg Ala Lys Val Glu Ile Thr Pro Asn Ser Pro
            115                 120                 125

Arg Ala Glu Ala Thr Leu Gly Gly Phe Gly Ser Leu Gly Leu Asp Cys
            130                 135                 140

Glu Pro Arg Thr Gly Leu Asp Phe Ser Asp Leu Tyr Tyr Leu Thr Met
145                 150                 155                 160

Gly Gly Thr Ile Ile Val Asn His Val Asn Asp Thr Trp Gly Leu Lys
                165                 170                 175

Val Arg Gln Ser Leu Trp Phe His Leu Ser Cys Leu Thr Phe Gly Gln
                180                 185                 190

His Thr Val Gln Glu Phe Leu Val Ser Phe Gly Val Trp Ile Arg Thr
            195                 200                 205

Pro Ala Pro Tyr Arg Pro Pro Asn Ala Pro Ile Leu Ser Thr Leu Pro
            210                 215                 220
```

Glu His Thr Val Ile Arg Arg Gly Gly Ala Arg Ala Ser Arg Ser
225                 230                 235                 240

Pro Arg Arg Arg Thr Pro Ser Pro Arg Arg Arg Ser Gln Ser Pro
                245                 250                 255

Arg Arg Arg Arg Ser Gln Ser Pro Ser Ala Asn Cys
            260                 265

<210> SEQ ID NO 22
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 1-2

<400> SEQUENCE: 22

Asp Val Gly Cys Ser Val Asp Phe Ser Lys Lys Glu Thr Arg Cys Gly
1               5                   10                  15

Thr

<210> SEQ ID NO 23
<211> LENGTH: 33
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 3-4

<400> SEQUENCE: 23

Asp Arg Tyr Lys Tyr His Pro Asp Ser Pro Arg Arg Leu Ala Ala Ala
1               5                   10                  15

Val Lys Gln Ala Trp Glu Asp Gly Ile Cys Gly Ile Ser Ser Val Ser
                20                  25                  30

Arg

<210> SEQ ID NO 24
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Alpha 2-Beta 5

<400> SEQUENCE: 24

Met Glu Asn Ile Met Trp Arg Ser Val Glu Gly Glu Leu Asn Ala Ile
1               5                   10                  15

Leu Glu Glu Asn Gly Val Gln Leu Thr Val Val Gly Ser Val
                20                  25                  30

<210> SEQ ID NO 25
<211> LENGTH: 89
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 4-5-6

<400> SEQUENCE: 25

-continued

Cys Gly Ile Ser Ser Val Ser Arg Met Glu Asn Ile Met Trp Arg Ser
1               5                   10                  15

Val Glu Gly Glu Leu Asn Ala Ile Leu Glu Asn Gly Val Gln Leu
            20                  25                  30

Thr Val Val Gly Ser Val Lys Asn Pro Met Trp Arg Gly Pro Gln
        35                  40                  45

Arg Leu Pro Val Pro Val Asn Glu Leu Pro His Gly Trp Lys Ala Trp
50                  55                  60

Gly Lys Ser Tyr Phe Val Arg Ala Ala Lys Thr Asn Asn Ser Phe Val
65                  70                  75                  80

Val Asp Gly Asp Thr Leu Lys Glu Cys
                85

<210> SEQ ID NO 26
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Intertwined Loop-Beta 6

<400> SEQUENCE: 26

Lys Asn Pro Met Trp Arg Gly Pro Gln Arg Leu Pro Val Pro Val Asn
1               5                   10                  15

Glu Leu Pro His Gly Trp Lys Ala Trp Gly Lys Ser Tyr Phe Val Arg
            20                  25                  30

Ala Ala Lys Thr Asn Asn Ser Phe Val Val Asp Gly
        35                  40

<210> SEQ ID NO 27
<211> LENGTH: 41
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 7-8-9

<400> SEQUENCE: 27

Asp Thr Leu Lys Glu Cys Pro Leu Lys His Arg Ala Trp Asn Ser Phe
1               5                   10                  15

Leu Val Glu Asp His Gly Phe Gly Val Phe His Thr Ser Val Trp Leu
            20                  25                  30

Lys Val Arg Glu Asp Tyr Ser Leu Glu
        35                  40

<210> SEQ ID NO 28
<211> LENGTH: 45
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 10-11-12-13

<400> SEQUENCE: 28

Cys Asp Pro Ala Val Ile Gly Thr Ala Val Lys Gly Lys Glu Ala Val
1               5                   10                  15

His Ser Asp Leu Gly Tyr Trp Ile Glu Ser Glu Lys Asn Asp Thr Trp
            20                  25                  30

Arg Leu Lys Arg Ala His Leu Ile Glu Met Lys Thr Cys
        35                  40                  45

<210> SEQ ID NO 29
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 12-13

<400> SEQUENCE: 29

Gly Tyr Trp Ile Glu Ser Glu Lys Asn Asp Thr Trp Arg Leu Lys Arg
1               5                   10                  15

Ala His Leu Ile
            20

<210> SEQ ID NO 30
<211> LENGTH: 63
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Spaghetti Loop-Beta 14

<400> SEQUENCE: 30

Arg Ala His Leu Ile Glu Met Lys Thr Cys Glu Trp Pro Lys Ser His
1               5                   10                  15

Thr Leu Trp Thr Asp Gly Ile Glu Glu Ser Asp Leu Ile Ile Pro Lys
            20                  25                  30

Ser Leu Ala Gly Pro Leu Ser His His Asn Thr Arg Glu Gly Tyr Arg
        35                  40                  45

Thr Gln Met Lys Gly Pro Trp His Ser Glu Glu Leu Glu Ile Arg
    50                  55                  60

<210> SEQ ID NO 31
<211> LENGTH: 54
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 14-15-16-17

<400> SEQUENCE: 31

Leu Glu Ile Arg Phe Glu Glu Cys Pro Gly Thr Lys Val His Val Glu
1               5                   10                  15

Glu Thr Cys Gly Thr Arg Gly Pro Ser Leu Arg Ser Thr Thr Ala Ser
            20                  25                  30

Gly Arg Val Ile Glu Glu Trp Cys Cys Arg Glu Cys Thr Met Pro Pro
        35                  40                  45

Leu Ser Phe Arg Ala Lys
    50

<210> SEQ ID NO 32
<211> LENGTH: 50
<212> TYPE: PRT

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 15-16-17-18

<400> SEQUENCE: 32

```
Cys Pro Gly Thr Lys Val His Val Glu Glu Thr Cys Gly Thr Arg Gly
1               5                   10                  15
Pro Ser Leu Arg Ser Thr Thr Ala Ser Gly Arg Val Ile Glu Glu Trp
            20                  25                  30
Cys Cys Arg Glu Cys Thr Met Pro Pro Leu Ser Phe Arg Ala Lys Asp
        35                  40                  45
Gly Cys
    50
```

<210> SEQ ID NO 33
<211> LENGTH: 89
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: NS1 Beta 14-15-16-17-18-19-C terminus

<400> SEQUENCE: 33

```
Met Lys Gly Pro Trp His Ser Glu Glu Leu Glu Ile Arg Phe Glu Glu
1               5                   10                  15
Cys Pro Gly Thr Lys Val His Val Glu Glu Thr Cys Gly Thr Arg Gly
            20                  25                  30
Pro Ser Leu Arg Ser Thr Thr Ala Ser Gly Arg Val Ile Glu Glu Trp
        35                  40                  45
Cys Cys Arg Glu Cys Thr Met Pro Pro Leu Ser Phe Arg Ala Lys Asp
    50                  55                  60
Gly Cys Trp Tyr Gly Met Glu Ile Arg Pro Arg Lys Glu Pro Glu Ser
65                  70                  75                  80
Asn Leu Val Arg Ser Met Val Thr Ala
                85
```

<210> SEQ ID NO 34
<211> LENGTH: 208
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:22

<400> SEQUENCE: 34

```
Met Asp Ile Asp Pro Tyr Lys Glu Phe Gly Ser Ser Tyr Gln Leu Leu
1               5                   10                  15
Asn Phe Leu Pro Leu Asp Phe Phe Pro Asp Leu Asn Ala Leu Val Asp
            20                  25                  30
Thr Ala Thr Ala Leu Tyr Glu Glu Glu Leu Thr Gly Arg Glu His Cys
        35                  40                  45
Ser Pro His His Thr Ala Ile Arg Gln Ala Leu Val Cys Trp Asp Glu
    50                  55                  60
Leu Thr Lys Leu Ile Ala Trp Met Ser Ser Asn Ile Gly Gly Gly Gly
65                  70                  75                  80
```

```
Thr Asp Val Gly Cys Ser Val Asp Phe Ser Lys Lys Glu Thr Arg Cys
                85                  90                  95

Gly Thr Gly Gly Gly Thr Ile Ile Val Asn His Val Asn Asp Thr
            100                 105                 110

Trp Gly Leu Lys Val Arg Gln Ser Leu Trp Phe His Leu Ser Cys Leu
            115                 120                 125

Thr Phe Gly Gln His Thr Val Gln Glu Phe Leu Val Ser Phe Gly Val
        130                 135                 140

Trp Ile Arg Thr Pro Ala Pro Tyr Arg Pro Pro Asn Ala Pro Ile Leu
145                 150                 155                 160

Ser Thr Leu Pro Glu His Thr Val Ile Arg Arg Arg Gly Gly Ala Arg
                165                 170                 175

Ala Ser Arg Ser Pro Arg Arg Arg Thr Pro Ser Pro Arg Arg Arg Arg
            180                 185                 190

Ser Gln Ser Pro Arg Arg Arg Ser Gln Ser Pro Ser Ala Asn Cys
        195                 200                 205
```

<210> SEQ ID NO 35
<211> LENGTH: 224
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:23

<400> SEQUENCE: 35

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly Gly
65                  70                  75                  80

Thr Asp Arg Tyr Lys Tyr His Pro Asp Ser Pro Arg Arg Leu Ala Ala
                85                  90                  95

Ala Val Lys Gln Ala Trp Glu Asp Gly Ile Cys Gly Ile Ser Ser Val
            100                 105                 110

Ser Arg Gly Gly Gly Gly Thr Ile Ile Val Asn His Val Asn Asp Thr
        115                 120                 125

Trp Gly Leu Lys Val Arg Gln Ser Leu Trp Phe His Leu Ser Cys Leu
        130                 135                 140

Thr Phe Gly Gln His Thr Val Gln Glu Phe Leu Val Ser Phe Gly Val
145                 150                 155                 160

Trp Ile Arg Thr Pro Ala Pro Tyr Arg Pro Pro Asn Ala Pro Ile Leu
                165                 170                 175

Ser Thr Leu Pro Glu His Thr Val Ile Arg Arg Arg Gly Gly Ala Arg
            180                 185                 190

Ala Ser Arg Ser Pro Arg Arg Arg Thr Pro Ser Pro Arg Arg Arg Arg
        195                 200                 205

Ser Gln Ser Pro Arg Arg Arg Ser Gln Ser Pro Ser Ala Asn Cys
    210                 215                 220
```

<210> SEQ ID NO 36
<211> LENGTH: 222
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:24

<400> SEQUENCE: 36

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
        50                  55                  60

Leu Thr Lys Leu Ile Ala Trp Met Ser Ser Asn Ile Gly Gly Gly Gly
65                  70                  75                  80

Thr Met Glu Asn Ile Met Trp Arg Ser Val Gly Glu Leu Asn Ala
                    85                  90                  95

Ile Leu Glu Glu Asn Gly Val Gln Leu Thr Val Val Gly Ser Val
                100                 105                 110

Gly Gly Gly Gly Thr Ile Ile Val Asn His Val Asn Asp Thr Trp Gly
            115                 120                 125

Leu Lys Val Arg Gln Ser Leu Trp Phe His Leu Ser Cys Leu Thr Phe
        130                 135                 140

Gly Gln His Thr Val Gln Glu Phe Leu Val Ser Phe Gly Val Trp Ile
145                 150                 155                 160

Arg Thr Pro Ala Pro Tyr Arg Pro Pro Asn Ala Pro Ile Leu Ser Thr
                    165                 170                 175

Leu Pro Glu His Thr Val Ile Arg Arg Arg Gly Gly Ala Arg Ala Ser
                180                 185                 190

Arg Ser Pro Arg Arg Arg Thr Pro Ser Pro Arg Arg Arg Arg Ser Gln
            195                 200                 205

Ser Pro Arg Arg Arg Arg Ser Gln Ser Pro Ser Ala Asn Cys
        210                 215                 220
```

<210> SEQ ID NO 37
<211> LENGTH: 280
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:25

<400> SEQUENCE: 37

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
```

```
                    50                  55                  60
Leu Thr Lys Leu Ile Ala Trp Met Ser Ser Asn Ile Gly Gly Gly
 65                  70                  75                  80

Thr Cys Gly Ile Ser Ser Val Ser Arg Met Glu Asn Ile Met Trp Arg
                 85                  90                  95

Ser Val Glu Gly Glu Leu Asn Ala Ile Leu Glu Asn Gly Val Gln
                100                 105                 110

Leu Thr Val Val Val Gly Ser Val Lys Asn Pro Met Trp Arg Gly Pro
             115                 120                 125

Gln Arg Leu Pro Val Pro Val Asn Glu Leu Pro His Gly Trp Lys Ala
     130                 135                 140

Trp Gly Lys Ser Tyr Phe Val Arg Ala Ala Lys Thr Asn Asn Ser Phe
145                 150                 155                 160

Val Val Asp Gly Asp Thr Leu Lys Glu Cys Gly Gly Gly Gly Thr Ile
                165                 170                 175

Ile Val Asn His Val Asn Asp Thr Trp Gly Leu Lys Val Arg Gln Ser
             180                 185                 190

Leu Trp Phe His Leu Ser Cys Leu Thr Phe Gly Gln His Thr Val Gln
         195                 200                 205

Glu Phe Leu Val Ser Phe Gly Val Trp Ile Arg Thr Pro Ala Pro Tyr
     210                 215                 220

Arg Pro Pro Asn Ala Pro Ile Leu Ser Thr Leu Pro Glu His Thr Val
225                 230                 235                 240

Ile Arg Arg Arg Gly Gly Ala Arg Ala Ser Arg Ser Pro Arg Arg Arg
                245                 250                 255

Thr Pro Ser Pro Arg Arg Arg Ser Gln Ser Pro Arg Arg Arg Arg
                260                 265                 270

Ser Gln Ser Pro Ser Ala Asn Cys
                275                 280

<210> SEQ ID NO 38
<211> LENGTH: 235
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:26

<400> SEQUENCE: 38

Met Asp Ile Asp Pro Tyr Lys Glu Phe Gly Ser Ser Tyr Gln Leu Leu
 1               5                  10                  15

Asn Phe Leu Pro Leu Asp Phe Phe Pro Asp Leu Asn Ala Leu Val Asp
             20                  25                  30

Thr Ala Thr Ala Leu Tyr Glu Glu Glu Leu Thr Gly Arg Glu His Cys
         35                  40                  45

Ser Pro His His Thr Ala Ile Arg Gln Ala Leu Val Cys Trp Asp Glu
     50                  55                  60

Leu Thr Lys Leu Ile Ala Trp Met Ser Ser Asn Ile Gly Gly Gly
 65                  70                  75                  80

Thr Lys Asn Pro Met Trp Arg Gly Pro Gln Arg Leu Pro Val Pro Val
                 85                  90                  95

Asn Glu Leu Pro His Gly Trp Lys Ala Trp Gly Lys Ser Tyr Phe Val
                100                 105                 110

Arg Ala Ala Lys Thr Asn Asn Ser Phe Val Val Asp Gly Gly Gly Gly
```

```
                115                 120                 125
Gly Thr Ile Ile Val Asn His Val Asn Asp Thr Trp Gly Leu Lys Val
            130                 135                 140

Arg Gln Ser Leu Trp Phe His Leu Ser Cys Leu Thr Phe Gly Gln His
145                 150                 155                 160

Thr Val Gln Glu Phe Leu Val Ser Phe Gly Val Trp Ile Arg Thr Pro
                165                 170                 175

Ala Pro Tyr Arg Pro Pro Asn Ala Pro Ile Leu Ser Thr Leu Pro Glu
            180                 185                 190

His Thr Val Ile Arg Arg Arg Gly Gly Ala Arg Ala Ser Arg Ser Pro
            195                 200                 205

Arg Arg Arg Thr Pro Ser Pro Arg Arg Arg Ser Gln Ser Pro Arg
210                 215                 220

Arg Arg Arg Ser Gln Ser Pro Ser Ala Asn Cys
225                 230                 235

<210> SEQ ID NO 39
<211> LENGTH: 232
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:27

<400> SEQUENCE: 39

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
            35                  40                  45

Ser Pro His His Thr Ala Ile Arg Gln Ala Leu Val Cys Trp Asp Glu
        50                  55                  60

Leu Thr Lys Leu Ile Ala Trp Met Ser Ser Asn Ile Gly Gly Gly Gly
65                  70                  75                  80

Thr Asp Thr Leu Lys Glu Cys Pro Leu Lys His Arg Ala Trp Asn Ser
                85                  90                  95

Phe Leu Val Glu Asp His Gly Phe Gly Val Phe His Thr Ser Val Trp
            100                 105                 110

Leu Lys Val Arg Glu Asp Tyr Ser Leu Glu Gly Gly Gly Gly Thr Ile
        115                 120                 125

Ile Val Asn His Val Asn Asp Thr Trp Gly Leu Lys Val Arg Gln Ser
    130                 135                 140

Leu Trp Phe His Leu Ser Cys Leu Thr Phe Gly Gln His Thr Val Gln
145                 150                 155                 160

Glu Phe Leu Val Ser Phe Gly Val Trp Ile Arg Thr Pro Ala Pro Tyr
                165                 170                 175

Arg Pro Pro Asn Ala Pro Ile Leu Ser Thr Leu Pro Glu His Thr Val
            180                 185                 190

Ile Arg Arg Arg Gly Gly Ala Arg Ala Ser Arg Ser Pro Arg Arg Arg
        195                 200                 205

Thr Pro Ser Pro Arg Arg Arg Ser Gln Ser Pro Arg Arg Arg Arg
    210                 215                 220

Ser Gln Ser Pro Ser Ala Asn Cys
```

-continued

```
225                 230

<210> SEQ ID NO 40
<211> LENGTH: 236
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:28

<400> SEQUENCE: 40

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly
65                  70                  75                  80

Thr Cys Asp Pro Ala Val Ile Gly Thr Ala Val Lys Gly Lys Glu Ala
                85                  90                  95

Val His Ser Asp Leu Gly Tyr Trp Ile Glu Ser Glu Lys Asn Asp Thr
            100                 105                 110

Trp Arg Leu Lys Arg Ala His Leu Ile Glu Met Lys Thr Cys Gly Gly
        115                 120                 125

Gly Gly Thr Ile Ile Val Asn His Val Asn Asp Thr Trp Gly Leu Lys
    130                 135                 140

Val Arg Gln Ser Leu Trp Phe His Leu Ser Cys Leu Thr Phe Gly Gln
145                 150                 155                 160

His Thr Val Gln Glu Phe Leu Val Ser Phe Gly Val Trp Ile Arg Thr
                165                 170                 175

Pro Ala Pro Tyr Arg Pro Pro Asn Ala Pro Ile Leu Ser Thr Leu Pro
            180                 185                 190

Glu His Thr Val Ile Arg Arg Gly Gly Ala Arg Ala Ser Arg Ser
        195                 200                 205

Pro Arg Arg Arg Thr Pro Ser Pro Arg Arg Arg Ser Gln Ser Pro
    210                 215                 220

Arg Arg Arg Arg Ser Gln Ser Pro Ser Ala Asn Cys
225                 230                 235

<210> SEQ ID NO 41
<211> LENGTH: 211
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:29

<400> SEQUENCE: 41

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30
```

```
Thr Ala Thr Ala Leu Tyr Glu Glu Glu Leu Thr Gly Arg Glu His Cys
         35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Gly Gly Gly Gly
 65                  70                  75                  80

Thr Gly Tyr Trp Ile Glu Ser Glu Lys Asn Asp Thr Trp Arg Leu Lys
                 85                  90                  95

Arg Ala His Leu Ile Gly Gly Gly Thr Ile Ile Val Asn His Val
             100                 105                 110

Asn Asp Thr Trp Gly Leu Lys Val Arg Gln Ser Leu Trp Phe His Leu
         115                 120                 125

Ser Cys Leu Thr Phe Gly Gln His Thr Val Gln Glu Phe Leu Val Ser
130                 135                 140

Phe Gly Val Trp Ile Arg Thr Pro Ala Pro Tyr Arg Pro Pro Asn Ala
145                 150                 155                 160

Pro Ile Leu Ser Thr Leu Pro Glu His Thr Val Ile Arg Arg Arg Gly
                165                 170                 175

Gly Ala Arg Ala Ser Arg Ser Pro Arg Arg Arg Thr Pro Ser Pro Arg
             180                 185                 190

Arg Arg Arg Ser Gln Ser Pro Arg Arg Arg Ser Gln Ser Pro Ser
         195                 200                 205

Ala Asn Cys
        210

<210> SEQ ID NO 42
<211> LENGTH: 254
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:30

<400> SEQUENCE: 42

Met Asp Ile Asp Pro Tyr Lys Glu Phe Gly Ser Ser Tyr Gln Leu Leu
 1               5                  10                  15

Asn Phe Leu Pro Leu Asp Phe Phe Pro Asp Leu Asn Ala Leu Val Asp
             20                  25                  30

Thr Ala Thr Ala Leu Tyr Glu Glu Glu Leu Thr Gly Arg Glu His Cys
         35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Gly Gly Gly Gly
 65                  70                  75                  80

Thr Arg Ala His Leu Ile Glu Met Lys Thr Cys Glu Trp Pro Lys Ser
                 85                  90                  95

His Thr Leu Trp Thr Asp Gly Ile Glu Glu Ser Asp Leu Ile Ile Pro
            100                 105                 110

Lys Ser Leu Ala Gly Pro Leu Ser His His Asn Thr Arg Glu Gly Tyr
         115                 120                 125

Arg Thr Gln Met Lys Gly Pro Trp His Ser Glu Glu Leu Glu Ile Arg
     130                 135                 140

Gly Gly Gly Gly Thr Ile Ile Val Asn His Val Asn Asp Thr Trp Gly
145                 150                 155                 160
```

```
Leu Lys Val Arg Gln Ser Leu Trp Phe His Leu Ser Cys Leu Thr Phe
            165                 170                 175
Gly Gln His Thr Val Gln Glu Phe Leu Val Ser Phe Gly Val Trp Ile
            180                 185                 190
Arg Thr Pro Ala Pro Tyr Arg Pro Pro Asn Ala Pro Ile Leu Ser Thr
            195                 200                 205
Leu Pro Glu His Thr Val Ile Arg Arg Arg Gly Gly Ala Arg Ala Ser
            210                 215                 220
Arg Ser Pro Arg Arg Arg Thr Pro Ser Pro Arg Arg Arg Arg Ser Gln
225                 230                 235                 240
Ser Pro Arg Arg Arg Arg Ser Gln Ser Pro Ser Ala Asn Cys
            245                 250

<210> SEQ ID NO 43
<211> LENGTH: 245
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:31

<400> SEQUENCE: 43

Met Asp Ile Asp Pro Tyr Lys Glu Phe Gly Ser Ser Tyr Gln Leu Leu
1               5                   10                  15
Asn Phe Leu Pro Leu Asp Phe Phe Pro Asp Leu Asn Ala Leu Val Asp
            20                  25                  30
Thr Ala Thr Ala Leu Tyr Glu Glu Leu Thr Gly Arg Glu His Cys
            35                  40                  45
Ser Pro His His Thr Ala Ile Arg Gln Ala Leu Val Cys Trp Asp Glu
    50                  55                  60
Leu Thr Lys Leu Ile Ala Trp Met Ser Ser Asn Ile Gly Gly Gly Gly
65                  70                  75                  80
Thr Leu Glu Ile Arg Phe Glu Cys Pro Gly Thr Lys Val His Val
                85                  90                  95
Glu Glu Thr Cys Gly Thr Arg Gly Pro Ser Leu Arg Ser Thr Thr Ala
            100                 105                 110
Ser Gly Arg Val Ile Glu Glu Trp Cys Cys Arg Glu Cys Thr Met Pro
            115                 120                 125
Pro Leu Ser Phe Arg Ala Lys Gly Gly Gly Thr Ile Ile Val Asn
            130                 135                 140
His Val Asn Asp Thr Trp Gly Leu Lys Val Arg Gln Ser Leu Trp Phe
145                 150                 155                 160
His Leu Ser Cys Leu Thr Phe Gly Gln His Thr Val Gln Glu Phe Leu
                165                 170                 175
Val Ser Phe Gly Val Trp Ile Arg Thr Pro Ala Pro Tyr Arg Pro Pro
            180                 185                 190
Asn Ala Pro Ile Leu Ser Thr Leu Pro Glu His Thr Val Ile Arg Arg
            195                 200                 205
Arg Gly Gly Ala Arg Ala Ser Arg Ser Pro Arg Arg Arg Thr Pro Ser
            210                 215                 220
Pro Arg Arg Arg Arg Ser Gln Ser Pro Arg Arg Arg Arg Ser Gln Ser
225                 230                 235                 240
Pro Ser Ala Asn Cys
            245
```

<210> SEQ ID NO 44
<211> LENGTH: 241
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:32

<400> SEQUENCE: 44

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly Gly
65                  70                  75                  80

Thr Cys Pro Gly Thr Lys Val His Val Glu Glu Thr Cys Gly Thr Arg
                85                  90                  95

Gly Pro Ser Leu Arg Ser Thr Thr Ala Ser Gly Arg Val Ile Glu Glu
            100                 105                 110

Trp Cys Cys Arg Glu Cys Thr Met Pro Pro Leu Ser Phe Arg Ala Lys
        115                 120                 125

Asp Gly Cys Gly Gly Gly Thr Ile Ile Val Asn His Val Asn Asp
    130                 135                 140

Thr Trp Gly Leu Lys Val Arg Gln Ser Leu Trp Phe His Leu Ser Cys
145                 150                 155                 160

Leu Thr Phe Gly Gln His Thr Val Gln Glu Phe Leu Val Ser Phe Gly
                165                 170                 175

Val Trp Ile Arg Thr Pro Ala Pro Tyr Arg Pro Asn Ala Pro Ile
            180                 185                 190

Leu Ser Thr Leu Pro Glu His Thr Val Ile Arg Arg Gly Gly Ala
        195                 200                 205

Arg Ala Ser Arg Ser Pro Arg Arg Arg Thr Pro Ser Pro Arg Arg Arg
    210                 215                 220

Arg Ser Gln Ser Pro Arg Arg Arg Ser Gln Ser Pro Ser Ala Asn
225                 230                 235                 240

Cys
```

<210> SEQ ID NO 45
<211> LENGTH: 280
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ. ID NO: 1) PLUS SEQ. ID NO:33

<400> SEQUENCE: 45

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30
```

```
Thr Ala Thr Ala Leu Tyr Glu Glu Leu Thr Gly Arg Glu His Cys
         35                  40                  45

Ser Pro His His Thr Ala Ile Arg Gln Ala Leu Val Cys Trp Asp Glu
 50                  55                  60

Leu Thr Lys Leu Ile Ala Trp Met Ser Ser Asn Ile Gly Gly Gly
 65                  70                  75                  80

Thr Met Lys Gly Pro Trp His Ser Glu Glu Leu Glu Ile Arg Phe Glu
             85                  90                  95

Glu Cys Pro Gly Thr Lys Val His Val Glu Glu Thr Cys Gly Thr Arg
            100                 105                 110

Gly Pro Ser Leu Arg Ser Thr Thr Ala Ser Gly Arg Val Ile Glu Glu
            115                 120                 125

Trp Cys Cys Arg Glu Cys Thr Met Pro Pro Leu Ser Phe Arg Ala Lys
130                 135                 140

Asp Gly Cys Trp Tyr Gly Met Glu Ile Arg Pro Arg Lys Glu Pro Glu
145                 150                 155                 160

Ser Asn Leu Val Arg Ser Met Val Thr Ala Gly Gly Gly Thr Ile
                165                 170                 175

Ile Val Asn His Val Asn Asp Thr Trp Gly Leu Lys Val Arg Gln Ser
                180                 185                 190

Leu Trp Phe His Leu Ser Cys Leu Thr Phe Gly Gln His Thr Val Gln
            195                 200                 205

Glu Phe Leu Val Ser Phe Gly Val Trp Ile Arg Thr Pro Ala Pro Tyr
            210                 215                 220

Arg Pro Pro Asn Ala Pro Ile Leu Ser Thr Leu Pro Glu His Thr Val
225                 230                 235                 240

Ile Arg Arg Arg Gly Gly Ala Arg Ala Ser Arg Ser Pro Arg Arg
                245                 250                 255

Thr Pro Ser Pro Arg Arg Arg Ser Gln Ser Pro Arg Arg Arg Arg
            260                 265                 270

Ser Gln Ser Pro Ser Ala Asn Cys
            275                 280

<210> SEQ ID NO 46
<211> LENGTH: 168
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: prM Furin Deficient

<400> SEQUENCE: 46

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn

-continued

```
Leu Pro Ser His Ser Thr Arg Lys Leu Gln Thr Arg Ser Gln Thr Trp
                100                 105                 110

Leu Glu Ser Arg Glu Tyr Thr Lys His Leu Ile Arg Val Glu Asn Trp
            115                 120                 125

Ile Phe Arg Asn Pro Gly Phe Ala Leu Ala Ala Ala Ile Ala Trp
        130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165

<210> SEQ ID NO 47
<211> LENGTH: 75
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: M full length

<400> SEQUENCE: 47

Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
        35                  40                  45

Ile Ala Trp Leu Leu Gly Ser Ser Thr Ser Gln Lys Val Ile Tyr Leu
    50                  55                  60

Val Met Ile Leu Leu Ile Ala Pro Ala Tyr Ser
65                  70                  75

<210> SEQ ID NO 48
<211> LENGTH: 359
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ. ID NO:46

<400> SEQUENCE: 48

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly
65                  70                  75                  80

Thr Ala Glu Val Thr Arg Arg Gly Ser Ala Tyr Tyr Met Tyr Leu Asp
            85                  90                  95

Arg Asn Asp Ala Gly Glu Ala Ile Ser Phe Pro Thr Thr Leu Gly Met
        100                 105                 110

Asn Lys Cys Tyr Ile Gln Ile Met Asp Leu Gly His Met Cys Asp Ala
    115                 120                 125
```

```
Thr Met Ser Tyr Glu Cys Pro Met Leu Asp Glu Gly Val Glu Pro Asp
    130                 135                 140

Asp Val Asp Cys Trp Cys Asn Thr Thr Ser Thr Trp Val Val Tyr Gly
145                 150                 155                 160

Thr Cys His His Lys Lys Gly Glu Ala Gly Ser Gly Gly Ala Val
            165                 170                 175

Thr Leu Pro Ser His Ser Thr Arg Lys Leu Gln Thr Arg Ser Gln Thr
        180                 185                 190

Trp Leu Glu Ser Arg Glu Tyr Thr Lys His Leu Ile Arg Val Glu Asn
        195                 200                 205

Trp Ile Phe Arg Asn Pro Gly Phe Ala Leu Ala Ala Ala Ile Ala
    210                 215                 220

Trp Leu Leu Gly Ser Ser Thr Ser Gln Lys Val Ile Tyr Leu Val Met
225                 230                 235                 240

Ile Leu Leu Ile Ala Pro Ala Tyr Ser Gly Gly Gly Thr Ile Ile
                245                 250                 255

Val Asn His Val Asn Asp Thr Trp Gly Leu Lys Val Arg Gln Ser Leu
            260                 265                 270

Trp Phe His Leu Ser Cys Leu Thr Phe Gly Gln His Thr Val Gln Glu
        275                 280                 285

Phe Leu Val Ser Phe Gly Val Trp Ile Arg Thr Pro Ala Pro Tyr Arg
    290                 295                 300

Pro Pro Asn Ala Pro Ile Leu Ser Thr Leu Pro Glu His Thr Val Ile
305                 310                 315                 320

Arg Arg Arg Gly Gly Ala Arg Ala Ser Arg Ser Pro Arg Arg Thr
                325                 330                 335

Pro Ser Pro Arg Arg Arg Arg Ser Gln Ser Pro Arg Arg Arg Arg Ser
                340                 345                 350

Gln Ser Pro Ser Ala Asn Cys
            355

<210> SEQ ID NO 49
<211> LENGTH: 266
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ. ID NO:47

<400> SEQUENCE: 49

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly Gly
65                  70                  75                  80

Thr Ala Val Thr Leu Pro Ser His Ser Thr Arg Lys Leu Gln Thr Arg
                85                  90                  95

Ser Gln Thr Trp Leu Glu Ser Arg Glu Tyr Thr Lys His Leu Ile Arg
            100                 105                 110
```

Val Glu Asn Trp Ile Phe Arg Asn Pro Gly Phe Ala Leu Ala Ala Ala
            115                 120                 125

Ala Ile Ala Trp Leu Leu Gly Ser Ser Thr Ser Gln Lys Val Ile Tyr
        130                 135                 140

Leu Val Met Ile Leu Leu Ile Ala Pro Ala Tyr Ser Gly Gly Gly Gly
145                 150                 155                 160

Thr Ile Ile Val Asn His Val Asn Asp Thr Trp Gly Leu Lys Val Arg
                165                 170                 175

Gln Ser Leu Trp Phe His Leu Ser Cys Leu Thr Phe Gly Gln His Thr
            180                 185                 190

Val Gln Glu Phe Leu Val Ser Phe Gly Val Trp Ile Arg Thr Pro Ala
        195                 200                 205

Pro Tyr Arg Pro Pro Asn Ala Pro Ile Leu Ser Thr Leu Pro Glu His
210                 215                 220

Thr Val Ile Arg Arg Gly Gly Ala Arg Ala Ser Arg Ser Pro Arg
225                 230                 235                 240

Arg Arg Thr Pro Ser Pro Arg Arg Arg Ser Gln Ser Pro Arg Arg
            245                 250                 255

Arg Arg Ser Gln Ser Pro Ser Ala Asn Cys
            260                 265

<210> SEQ ID NO 50
<211> LENGTH: 104
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: C full length

<400> SEQUENCE: 50

Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Gly His Gly Pro Ile Arg Met Val Leu
        35                  40                  45

Ala Ile Leu Ala Phe Leu Arg Phe Thr Ala Ile Lys Pro Ser Leu Gly
        50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg
            100

<210> SEQ ID NO 51
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: C alpha 2

<400> SEQUENCE: 51

Gly His Gly Pro Ile Arg Met Val Leu Ala Ile Leu Ala Phe Leu Arg

```
1               5                   10                  15
Phe Thr Ala Ile Lys Pro Ser Leu Gly
            20                  25

<210> SEQ ID NO 52
<211> LENGTH: 295
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID  NO:50

<400> SEQUENCE: 52

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly Gly
65                  70                  75                  80

Thr Met Lys Asn Pro Lys Lys Ser Gly Gly Phe Arg Ile Val Asn
                85                  90                  95

Met Leu Lys Arg Gly Val Ala Arg Val Ser Pro Phe Gly Leu Lys
            100                 105                 110

Arg Leu Pro Ala Gly Leu Leu Leu Gly His Gly Pro Ile Arg Met Val
        115                 120                 125

Leu Ala Ile Leu Ala Phe Leu Arg Phe Thr Ala Ile Lys Pro Ser Leu
    130                 135                 140

Gly Leu Ile Asn Arg Trp Gly Ser Val Gly Lys Lys Glu Ala Met Glu
145                 150                 155                 160

Thr Ile Lys Lys Phe Lys Lys Asp Leu Ala Ala Met Leu Arg Ile Ile
                165                 170                 175

Asn Ala Arg Lys Glu Lys Lys Arg Gly Gly Gly Gly Thr Ile Ile
            180                 185                 190

Val Asn His Val Asn Asp Thr Trp Gly Leu Lys Val Arg Gln Ser Leu
        195                 200                 205

Trp Phe His Leu Ser Cys Leu Thr Phe Gly Gln His Thr Val Gln Glu
    210                 215                 220

Phe Leu Val Ser Phe Gly Val Trp Ile Arg Thr Pro Ala Pro Tyr Arg
225                 230                 235                 240

Pro Pro Asn Ala Pro Ile Leu Ser Thr Leu Pro Glu His Thr Val Ile
                245                 250                 255

Arg Arg Arg Gly Gly Ala Arg Ala Ser Arg Ser Pro Arg Arg Thr
            260                 265                 270

Pro Ser Pro Arg Arg Arg Ser Gln Ser Pro Arg Arg Arg Ser
        275                 280                 285

Gln Ser Pro Ser Ala Asn Cys
    290                 295

<210> SEQ ID NO 53
<211> LENGTH: 216
<212> TYPE: PRT
```

<210> SEQ ID NO 53 (implied continuation)

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: WHcAg (SEQ ID NO: 1) PLUS SEQ ID NO:51

<400> SEQUENCE: 53
```

```
Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Gly Gly Gly Gly
65                  70                  75                  80

Thr Gly His Gly Pro Ile Arg Met Val Leu Ala Ile Leu Ala Phe Leu
                85                  90                  95

Arg Phe Thr Ala Ile Lys Pro Ser Leu Gly Gly Gly Gly Gly Thr Ile
            100                 105                 110

Ile Val Asn His Val Asn Asp Thr Trp Gly Leu Lys Val Arg Gln Ser
        115                 120                 125

Leu Trp Phe His Leu Ser Cys Leu Thr Phe Gly Gln His Thr Val Gln
    130                 135                 140

Glu Phe Leu Val Ser Phe Gly Val Trp Ile Arg Thr Pro Ala Pro Tyr
145                 150                 155                 160

Arg Pro Pro Asn Ala Pro Ile Leu Ser Thr Leu Pro Glu His Thr Val
                165                 170                 175

Ile Arg Arg Arg Gly Gly Ala Arg Ala Ser Arg Ser Pro Arg Arg Arg
            180                 185                 190

Thr Pro Ser Pro Arg Arg Arg Ser Gln Ser Pro Arg Arg Arg
        195                 200                 205

Ser Gln Ser Pro Ser Ala Asn Cys
    210                 215
```

```
<210> SEQ ID NO 54
<211> LENGTH: 564
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WOODCHUCK HEPATITIS CORE ANTIGEN (WHCAG)

<400> SEQUENCE: 54
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcac ttctgaacaa    240
gttagaacta tcatcgttaa ccacgttaac gacacttggg gtttgaaggt tagacaatct    300
ttgtggttcc acttgtcttg tttgactttc ggtcaacaca ctgttcaaga attcttggtt    360
tctttcggtg tttggatcag aactccagct ccatacagac accaaaacgc tccaatcttg    420
tctactttgc cagaacacac tgttatcaga agaagaggtg gtgctagagc ttctagatct    480
```

```
ccaagaagaa gaactccatc tccaagaaga agaagatctc aatctccaag aagaagaaga    540
tctcaatctc catctgctaa ctgt                                          564
```

<210> SEQ ID NO 55
<211> LENGTH: 408
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: Envelope domain 3 full length

<400> SEQUENCE: 55

```
cacttgaagt gtagattgaa gatggacaag ttgagattga agggtgtttc ttactctttg    60
tgtactgctg ctttcacttt cactaagatc ccagctgaaa ctttgcacgg tactgttact   120
gttgaagttc aatacgctgg tactgacggt ccatgtaagg ttccagctca aatggctgtt   180
gacatgcaaa ctttgactcc agttggtaga ttgatcactg ctaacccagt tatcactgaa   240
tctactgaaa actctaagat gatgttggaa ttggacccac cattcggtga ctcttacatc   300
gttatcggtg ttggtgaaaa agagatcact caccactggc acagatctgg ttctactatc   360
ggtaaggctt tcgaagctac tgttagaggt gctaagagaa tggctgtt                408
```

<210> SEQ ID NO 56
<211> LENGTH: 240
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: Envelope domain 3 (EDIII) G loop-truncated

<400> SEQUENCE: 56

```
gctttcactt tcactaagat cccagctgaa actttgcacg gtactgttac tgttgaattg    60
caatacgctg gtactgacgg tccatgtaag gttccagctc aaatggctgt tgacatgcaa   120
actttgactc cagttggtag attgatcact gctaacccag ttatcactga atctactgaa   180
aactctaaga tgatgttgga attggaccca ccattcggtg actcttacat cgttatcggt   240
```

<210> SEQ ID NO 57
<211> LENGTH: 69
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: Envelope domain 3, A-B loop

<400> SEQUENCE: 57

```
gctttcactt tcactaagat cccagctgaa actttgcacg gtactgttac tgttgaattg    60
caatacgct                                                           69
```

<210> SEQ ID NO 58
<211> LENGTH: 87
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE

```
<223> OTHER INFORMATION: Envelope domain 3, CXCDDX loop

<400> SEQUENCE: 58
ccatgtaagg ttccagctca a

```
<210> SEQ ID NO 63
<211> LENGTH: 183
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: Envelope domain 2 sequence B-D

<400> SEQUENCE: 63
gaagcttcta tctctgacat ggcttctgac tctagatgtc caactcaagg tgaagcttac    60
ttggacaagc aatctgacac tcaatacgtt tgtaagagaa ctttggttga cagaggttgg   120
ggtaacggtt gtggtttgtt cggtaagggt tctttggtta cttgtgctaa gttcgcttgt   180
tct                                                                 183

<210> SEQ ID NO 64
<211> LENGTH: 246
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: Envelope domain 1 glycan loop

<400> SEQUENCE: 64
atgactggta agtctatcca accagaaaac ttggaataca gaatcatgtt gtctgttcac    60
ggttctcaac actctggtat gatcgttaac gacactggtc acgaaactga cgaaaacaga   120
gctaaggttg aaatcactcc aaactctcca agagctgaag ctactttggg tggtttcggt   180
tctttgggtt tggactgtga accagaaact ggtttggact ctctgacttt gtactacttg   240
actatg                                                              246

<210> SEQ ID NO 65
<211> LENGTH: 981
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:55

<400> SEQUENCE: 65
atggacatcg acccatacaa ggaattcggt tcttcttacc aattgttgaa cttcttgcca    60
ttggacttct tcccagactt gaacgctttg gttgacactg ctactgcttt gtacgaagaa   120
gaattgactg gtagagaaca ctgttctcca caccacactg ctatcagaca gctttggtt   180 tgttgggacg aattgactaa gttgatcgct tggatgtctt ctaacatcgg tggtggtggt   240
actcacttga gtgtagatt gaagatggac aagttgagat tgaagggtgt ttcttactct   300
ttgtgtactg ctgctttcac tttcactaag atcccagctg aaactttgca cggtactgtt   360
actgttgaag ttcaatacgc tggtactgac ggtccatgta aggttccagc tcaaatggct   420
gttgacatgc aaactttgac tccagttggt agattgatca ctgctaaccc agttatcact   480
gaatctactg aaaactctaa gatgatgttg gaattggacc accattcggt tgactcttac   540
atcgttatcg tgttggtga aaagaagatc actcaccact ggcacagatc tggttctact   600
atcggtaagg ctttcgaagc tactgttaga ggtgctaaga gaatggctgt tggtggtggt   660
```

```
ggtactatca tcgttaacca cgttaacgac acttggggtt tgaaggttag acaatctttg    720
tggttccact tgtcttgttt gactttcggt caacacactg ttcaagaatt cttggtttct    780
ttcggtgttt ggatcagaac tccagctcca tacagaccac caaacgctcc aatcttgtct    840
actttgccag aacacactgt tatcagaaga gaggtggtg ctagagcttc tagatctcca     900
agaagaagaa ctccatctcc aagaagaaga agatctcaat ctccaagaag aagaagatct    960
caatctccat ctgctaactg t                                              981
```

<210> SEQ ID NO 66
<211> LENGTH: 786
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:56

<400> SEQUENCE: 66

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct ggatgtcttc taacatcgc tttcactttc     240 actaagatcc cagctgaaac tttgcacggt actgttactg ttgaattgca atacgctggt    300
actgacggtc catgtaaggt tccagctcaa atggctgttg acatgcaaac tttgactcca    360
gttggtagat tgatcactgc taacccagtt atcactgaat ctactgaaaa ctctaagatg    420
atgttggaat tggacccacc attcggtgac tcttacatcg ttatcggtac tatcatcgtt    480
aaccacgtta acgacacttg gggtttgaag gttagacaat cttttgtggtt ccacttgtct    540 tgtttgactt tcggtcaaca cactgttcaa gaattcttgg tttctttcgg tgtttggatc    600
agaactccag ctccatacag accaccaaac gctccaatct tgtctacttt gccagaacac    660
actgttatca gaagaagagg tggtgctaga gcttctagat ctccaagaag aagaactcca    720
tctccaagaa gaagaagatc tcaatctcca agaagaagaa gatctcaatc tccatctgct    780
aactgt                                                               786
```

<210> SEQ ID NO 67
<211> LENGTH: 615
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:57

<400> SEQUENCE: 67

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct ggatgtcttc taacatcgc tttcactttc     240 actaagatcc cagctgaaac tttgcacggt actgttactg ttgaattgca atacgctact    300
atcatcgtta accacgttaa cgacacttgg ggtttgaagg ttagacaatc tttgtggttc    360
```

```
cacttgtctt gtttgacttt cggtcaacac actgttcaag aattcttggt ttctttcggt    420
gtttggatca gaactccagc tccatacaga ccaccaaacg ctccaatctt gtctactttg    480
ccagaacaca ctgttatcag aagaagaggt ggtgctagag cttctagatc tccaagaaga    540
agaactccat ctccaagaag aagagatct caatctccaa gaagaagaag atctcaatct    600
ccatctgcta actgt                                                    615
```

<210> SEQ ID NO 68
<211> LENGTH: 633
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:58

<400> SEQUENCE: 68

```
atggacatcg acccatacaa ggaattcggt tcttcttacc aattgttgaa cttcttgcca    60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatccc atgtaaggtt    240
ccagctcaaa tggctgttga catgcaaact ttgactccag ttggtagatt gatcactgct    300
aacccagtta tcactactat catcgttaac cacgttaacg acacttgggg tttgaaggtt    360
agacaatctt gtggttcca cttgtcttgt ttgactttcg gtcaacacac tgttcaagaa    420
ttcttggttt ctttcggtgt ttggatcaga actccagctc catacagacc accaaacgct    480
ccaatcttgt ctactttgcc agaacacact gttatcagaa gaagaggtgg tgctagagct    540
tctagatctc caagaagaag aactccatct ccaagaagaa gagatctca atctccaaga    600 agaagaagat ctcaatctcc atctgctaac tgt                                633
```

<210> SEQ ID NO 69
<211> LENGTH: 618
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:59

<400> SEQUENCE: 69

```
atggacatcg acccatacaa ggaattcggt tcttcttacc aattgttgaa cttcttgcca    60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcag attgatcact    240
gctaacccag ttatcactga atctactgaa aactctaaga tgatgttgga attggaccca    300
actatcatcg ttaaccacgt taacgacact tggggtttga aggttagaca atctttgtgg    360
ttccacttgt cttgtttgac tttcggtcaa cacactgttc aagaattctt ggtttctttc    420
ggtgtttgga tcagaactcc agctccatac agaccaccaa acgctccaat cttgtctact    480
ttgccagaac acactgttat cagaagaaga ggtggtgcta gagcttctag atctccaaga    540
```
agaagaactc catctccaag aagaagaaga tctcaatctc caagaagaag aagatctcaa      600
tctccatctg ctaactgt                                                    618

<210> SEQ ID NO 70
<211> LENGTH: 606
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:60

<400> SEQUENCE: 70
atggacatcg acccatacaa ggaattcggt tcttcttacc aattgttgaa cttcttgcca       60
ttggacttct tcccagactt gaacgctttg gttgacactg ctactgcttt gtacgaagaa      120
gaattgactg gtagagaaca ctgttctcca caccacactg ctatcagaca agctttggtt      180
tgttgggacg aattgactaa gttgatcgct tggatgtctt ctaacatcgg tgactcttac      240
atcgttatcg gtgttggtga aagaagatc actcaccact ggcacagaac tatcatcgtt      300
aaccacgtta acgacacttg ggggtttgaag gttagacaat ctttgtggtt ccacttgtct      360
tgtttgactt tcggtcaaca cactgttcaa gaattcttgg tttctttcgg tgtttggatc      420
agaactccag ctccatacag accaccaaac gctccaatct tgtctacttt gccagaacac      480
actgttatca agaagagg tggtgctaga gcttctagat ctccaagaag aagaactcca      540
tctccaagaa gaagagatc tcaatctcca agaagaagaa gatctcaatc tccatctgct      600
aactgt                                                                606

<210> SEQ ID NO 71
<211> LENGTH: 600
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:61

<400> SEQUENCE: 71
atggacatcg acccatacaa ggaattcggt tcttcttacc aattgttgaa cttcttgcca       60
ttggacttct tcccagactt gaacgctttg gttgacactg ctactgcttt gtacgaagaa      120
gaattgactg gtagagaaca ctgttctcca caccacactg ctatcagaca agctttggtt      180
tgttgggacg aattgactaa gttgatcgct tggatgtctt ctaacatcgg tggtactgac      240
agaggttggg gtaacggttg tggtttgttc ggtaagggtg gtactatcat cgttaaccac      300
gttaacgaca cttgggggttt gaaggttaga caatctttgt ggttccactt gtcttgtttg      360
actttcggtc aacacactgt tcaagaattc ttggtttctt tcggtgtttg gatcagaact      420
ccagctccat acagaccacc aaacgctcca atcttgtcta ctttgccaga acacactgtt      480
atcagaagaa gaggtggtgc tagagcttct agatctccaa gaagaagaac tccatctcca      540
agaagaagaa gatctcaatc tccaagaaga agaagatctc aatctccatc tgctaactgt      600

<210> SEQ ID NO 72
<211> LENGTH: 834
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:62

<400> SEQUENCE: 72
atggacatcg acccatacaa ggaattcggt tcttcttacc aattgttgaa cttcttgcca      60
ttggacttct tcccagactt gaacgctttg gttgacactg ctactgcttt gtacgaagaa     120
gaattgactg gtagagaaca ctgttctcca caccacactg ctatcagaca agctttggtt     180
tgttgggacg aattgactaa gttgatcgct tggatgtctt ctaacatcgg tggtactact     240
actgtttcta acatggctga agttagatct tactgttacg aagcttctat ctctgacatg     300
gcttctgact ctagatgtcc aactcaaggt gaagcttact tggacaagca atctgacact     360
caatacgttt gtaagagaac tttggttgac agaggttggg gtaacggttg gtttgttc      420 ggtaagggtt ctttggttac ttgtgctaag ttcgcttgtt ctaagaagat gactggtaag     480
tctatccaac cagaaaactt ggaatacaga ggtggtacta tcatcgttaa ccacgttaac     540
gacacttggg gtttgaaggt tagacaatct tgtggttcc acttgtcttg tttgactttc      600
ggtcaacaca ctgttcaaga attcttggtt ctttcggtg tttggatcag aactccagct      660
ccatacagac accaaacgc tccaatcttg tctactttgc cagaacacac tgttatcaga     720
agaagaggtg gtgctagagc ttctagatct ccaagaagaa gaactccatc tccaagaaga     780
agaagatctc aatctccaag aagaagaaga tctcaatctc catctgctaa ctgt           834

<210> SEQ ID NO 73
<211> LENGTH: 741
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:63

<400> SEQUENCE: 73
atggacatcg acccatacaa ggaattcggt tcttcttacc aattgttgaa cttcttgcca      60
ttggacttct tcccagactt gaacgctttg gttgacactg ctactgcttt gtacgaagaa     120
gaattgactg gtagagaaca ctgttctcca caccacactg ctatcagaca agctttggtt     180
tgttgggacg aattgactaa gttgatcgct tggatgtctt ctaacatcgg tggtgaagct     240
tctatctctg acatggcttc tgactctaga tgtccaactc aaggtgaagc ttacttggac     300
aagcaatctg acactcaata cgtttgtaag agaactttgg ttgacagagg ttggggtaac     360
ggttgtggtt tgttcggtaa gggttctttg gttacttgtg ctaagttcgc ttgttctggt     420
ggtactatca tcgttaacca cgttaacgac acttggggt tgaaggttag acaatctttg      480
tggttccact tgtcttgttt gactttcggt caacacactg ttcaagaatt cttggtttct     540
ttcggtgttt ggatcagaac tccagctcca tacagaccac caaacgctcc aatcttgtct     600
actttgccag aacacactgt tatcagaaga agaggtggtg ctagagcttc tagatctcca     660
agaagaagaa ctccatctcc aagaagaaga agatctcaat ctccaagaag aagaagatct     720
caatctccat ctgctaactg t                                               741

<210> SEQ ID NO 74
```

```
<211> LENGTH: 804
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg POLYNUCLEOTIDE SEQUENCE (SEQ ID NO: 54)
      PLUS SEQ ID NO:64

<400> SEQUENCE: 74
atggacatcg acccatacaa ggaattcggt tcttcttacc aattgttgaa cttcttgcca      60
ttggacttct tcccagactt gaacgctttg gttgacactg ctactgcttt gtacgaagaa     120
gaattgactg gtagagaaca ctgttctcca caccacactg ctatcagaca agctttggtt     180
tgttgggacg aattgactaa gttgatcgct ggatgtcttc taacatcggt ggtatgact     240 ggtaagtcta tccaaccaga aaacttggaa tacagaatca tgttgtctgt tcacggttct     300
caacactctg gtatgatcgt taacgacact ggtcacgaaa ctgacgaaaa cagagctaag     360
gttgaaatca ctccaaactc tccaagagct gaagctactt gggtggtttt cggttctttg     420
ggtttggact gtgaaccaag aactggtttg gacttctctg acttgtacta cttgactatg     480
ggtggtacta tcatcgttaa ccacgttaac gacacttggg gtttgaaggt tagacaatct     540
ttgtggttcc acttgtcttg tttgactttc ggtcaacaca ctgttcaaga attcttggtt     600
tctttcggtg tttggatcag aactccagct ccatacagac accaaaacgc tccaatcttg     660
tctactttgc cagaacacac tgttatcaga agaagaggtg gtgctagagc ttctagatct     720
ccaagaagaa gaactccatc tccaagaaga agaagatctc aatctccaag aagaagaaga     780
tctcaatctc catctgctaa ctgt                                            804

<210> SEQ ID NO 75
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 1-2

<400> SEQUENCE: 75
gacgttggtt gttctgttga cttctctaag aaggaaacta gatgtggtac t               51

<210> SEQ ID NO 76
<211> LENGTH: 99
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 3-4

<400> SEQUENCE: 76
gacagataca agtaccaccc agactctcca agaagattgg ctgctgctgt taagcaagct      60
tgggaagacg gtatctgtgg tatctcttct gtttctaga                             99

<210> SEQ ID NO 77
<211> LENGTH: 93
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: MISC_FEATURE
<223> OTHER INFORMATION: NS1 Alpha 2-Beta 5

<400> SEQUENCE: 77
atggaaaaca tcatgtggag atctgttgaa ggtgaattga acgctatctt ggaagaaaac      60
ggtgttcaat tgactgttgt tgttggttct gtt                                  93

<210> SEQ ID NO 78
<211> LENGTH: 270
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 4-5-6

<400> SEQUENCE: 78
tgtggtatct cttctgtttc tagaatggaa aacatcatgt ggagatctgt tgaaggtgaa      60
ttgaacgcta tcttggaaga aaacggtgtt caattgactg ttgttgttgg ttctgttaag     120
aacccaatgt ggagaggtcc acaaagattg ccagttccag ttaacgaatt gccacacggt     180
tggaaggctt ggggtaagtc ttacttcgtt agagctgcta agactaacaa ctctttcgtt     240
gttgacggtg acactttgaa ggaatgtgtt                                     270

<210> SEQ ID NO 79
<211> LENGTH: 132
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Inter. Loop-Beta 6

<400> SEQUENCE: 79
aagaacccaa tgtggagagg tccacaaaga ttgccagttc cagttaacga attgccacac      60
ggttggaagg cttggggtaa gtcttacttc gttagagctg ctaagactaa caactctttc     120
gttgttgacg gt                                                        132

<210> SEQ ID NO 80
<211> LENGTH: 123
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 7-8-9

<400> SEQUENCE: 80
gacactttga aggaatgtcc attgaagcac agagcttgga actctttctt ggttgaagac      60
cacggtttcg gtgttttcca cacttctgtt tggttgaagg ttagagaaga ctactctttg     120
gaa                                                                  123

<210> SEQ ID NO 81
<211> LENGTH: 135
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: MISC_FEATURE
<223> OTHER INFORMATION: NS1 Beta 10-11-12-13

<400> SEQUENCE: 81
tgtgacccag ctgttatcgg tactgctgtt aagggtaagg aagctgttca ctctgacttg    60
ggttactgga tcgaatctga aaagaacgac acttggagat tgaagagagc tcacttgatc   120
gaaatgaaga cttgt                                                    135

<210> SEQ ID NO 82
<211> LENGTH: 60
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 12-13

<400> SEQUENCE: 82
ggttactgga tcgaatctga aaagaacgac acttggagat tgaagagagc tcacttgatc    60

<210> SEQ ID NO 83
<211> LENGTH: 189
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Spaghetti Loop-Beta 14

<400> SEQUENCE: 83
agagctcact tgatcgaaat gaagacttgt gaatggccaa agtctcacac tttgtggact    60
gacggtatcg aagaatctga cttgatcatc ccaaagtctt tggctggtcc attgtctcac   120
cacaacacta gagaaggtta cagaactcaa atgaagggtc catggcactc tgaagaattg   180
gaaatcaga                                                           189

<210> SEQ ID NO 84
<211> LENGTH: 162
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 14-15-16-17

<400> SEQUENCE: 84
ttggaaatca gattcgaaga atgtccaggt actaaggttc acgttgaaga aacttgtggt    60
actagaggtc catctttgag atctactact gcttctggta gagttatcga agaatggtgt   120
tgtagagaat gtactatgcc accattgtct ttcagagcta ag                      162

<210> SEQ ID NO 85
<211> LENGTH: 150
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 15-16-17-18

<400> SEQUENCE: 85
```

```
tgtccaggta ctaaggttca cgttgaagaa acttgtggta ctagaggtcc atctttgaga    60
tctactactg cttctggtag agttatcgaa gaatggtgtt gtagagaatg tactatgcca   120
ccattgtctt tcagagctaa ggacggttgt                                    150
```

<210> SEQ ID NO 86
<211> LENGTH: 267
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: NS1 Beta 14-15-16-17-18-19-C-term.

<400> SEQUENCE: 86

```
atgaagggtc catggcactc tgaagaattg gaaatcagat tcgaagaatg tccaggtact    60
aaggttcacg ttgaagaaac ttgtggtact agaggtccat ctttgagatc tactactgct   120
tctggtagag ttatcgaaga tggtgttgt agagaatgta ctatgccacc attgtctttc   180
agagctaagg acggttgttg gtacggtatg gaaatcagac caagaaagga accagaatct   240
aacttggtta gatctatggt tactgct                                       267
```

<210> SEQ ID NO 87
<211> LENGTH: 624
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 75

<400> SEQUENCE: 87

```
atggacatcg acccatacaa ggaattcggt tcttcttacc aattgttgaa cttcttgcca    60
ttggacttct tcccagactt gaacgctttg gttgacactg ctactgcttt gtacgaagaa   120
gaattgactg gtagagaaca ctgttctcca caccacactg ctatcagaca agctttggtt   180
tgttgggacg aattgactaa gttgatcgct tggatgtctt ctaacatcgg tggtggtggt   240
actgacgttg ttgttctgt tgacttctct aagaaggaaa ctagatgtgg tactggtggt   300
ggtggtacta tcatcgttaa ccacgttaac gacacttggg gtttgaaggt tagacaatct   360 tgtggttcc acttgtcttg tttgactttc ggtcaacaca ctgttcaaga attcttggtt   420
tctttcggtg tttggatcag aactccagct ccatacagac caccaaacgc tccaatcttg   480
tctactttgc cagaacacac tgttatcaga agaagaggtg gtgctagagc ttctagatct   540
ccaagaagaa gaactccatc tccaagaaga agaagatctc aatctccaag aagaagaaga   600
tctcaatctc catctgctaa ctgt                                          624
```

<210> SEQ ID NO 88
<211> LENGTH: 672
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 76

<400> SEQUENCE: 88

```
atggacatcg acccatacaa ggaattcggt tcttcttacc aattgttgaa cttcttgcca    60
```

```
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actgacagat acaagtacca cccagactct ccaagaagat ggctgctgc  gttaagcaa     300 gcttgggaag acggtatctg tggtatctct tctgtttcta gaggtggtgg tggtactatc    360
atcgttaacc acgttaacga cacttggggt tgaaggttta caaatctttt gtggttccac    420 tgtcttgtt tgactttcgg tcaacacact gttcaagaat tcttggtttc tttcggtgtt    480
tggatcagaa ctccagctcc atacagacca ccaaacgctc aatcttgtc tactttgcca     540 gaacacactg ttatcagaag aagaggtggt gctagagctt ctagatctcc aagaagaaga    600
actccatctc caagaagaag aagatctcaa tctccaagaa gaagaagatc tcaatctcca    660
tctgctaact gt                                                        672

<210> SEQ ID NO 89
<211> LENGTH: 666
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 77

<400> SEQUENCE: 89
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actatggaaa acatcatgtg gagatctgtt gaaggtgaat tgaacgctat cttggaagaa    300
aacggtgttc aattgactgt tgttgttggt tctgttggtg tggtggtac  tatcatcgtt    360 aaccacgtta acgacacttg gggtttgaag gttagacaat cttgtggtt ccacttgtct    420 tgtttgactt tcggtcaaca cactgttcaa gaattcttgg tttcttcgg tgtttggatc     480 agaactccag ctccatacag accaccaaac gctccaatct gtctactttt gccagaacac    540
actgttatca agaagagg tggtgctaga gcttctagat ctccaagaag aagaactcca     600
tctccaagaa gaagaagatc tcaatctcca agaagaagaa gatctcaatc tccatctgct    660
aactgt                                                               666

<210> SEQ ID NO 90
<211> LENGTH: 840
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 78

<400> SEQUENCE: 90
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
```

```
acttgtggta tctcttctgt ttctagaatg gaaaacatca tgtggagatc tgttgaaggt      300
gaattgaacg ctatcttgga agaaaacggt gttcaattga ctgttgttgt tggttctgtt      360
aagaacccaa tgtggagagg tccacaaaga ttgccagttc cagttaacga attgccacac      420
ggttggaagg cttggggtaa gtcttacttc gttagagctg ctaagactaa caactctttc      480
gttgttgacg gtgacacttt gaaggaatgt ggtggtggtg gtactatcat cgttaaccac      540
gttaacgaca cttggggttt gaaggttaga caatctttgt ggttccactt gtcttgtttg      600
actttcggtc aacacactgt tcaagaattc ttggtttctt tcggtgtttg gatcagaact      660
ccagctccat acagaccacc aaacgctcca atcttgtcta ctttgccaga acacactgtt      720
atcagaagaa gaggtggtgc tagagcttct agatctccaa gaagaagaac tccatctcca      780
agaagaagaa gatctcaatc tccaagaaga agaagatctc aatctccatc tgctaactgt      840
```

<210> SEQ ID NO 91
<211> LENGTH: 705
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 79

<400> SEQUENCE: 91

```
atggacatcg acccatacaa ggaattcggt tcttcttacc aattgttgaa cttcttgcca       60
ttggacttct tcccagactt gaacgctttg gttgacactg ctactgcttt gtacgaagaa      120
gaattgactg gtagagaaca ctgttctcca caccacactg ctatcagaca agctttggtt      180
tgttgggacg aattgactaa gttgatcgct tggatgtctt ctaacatcgg tggtggtggt      240
actaagaacc caatgtggag aggtccacaa agattgccag ttccagttaa cgaattgcca      300
cacggttgga aggcttgggg taagtcttac ttcgttagag ctgctaagac taacaactct      360
ttcgttgttg acggtggtgg tggtggtact atcatcgtta accacgttaa cgacacttgg      420
ggtttgaagg ttagacaatc tttgtggttc acttgtcttg ttttgacttt cggtcaacac      480
actgttcaag aattcttggt ttctttcggt gtttggatca gaactccagc tccatacaga      540
ccaccaaacg ctccaatctt gtctactttg ccagaacaca ctgttatcag aagaagaggt      600
ggtgctagag cttctagatc tccaagaaga agaactccat ctccaagaag aagagatct      660 caatctccaa gaagaagaag atctcaatct ccatctgcta actgt                      705
```

<210> SEQ ID NO 92
<211> LENGTH: 696
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 80

<400> SEQUENCE: 92

```
atggacatcg acccatacaa ggaattcggt tcttcttacc aattgttgaa cttcttgcca       60
ttggacttct tcccagactt gaacgctttg gttgacactg ctactgcttt gtacgaagaa      120
gaattgactg gtagagaaca ctgttctcca caccacactg ctatcagaca agctttggtt      180
tgttgggacg aattgactaa gttgatcgct tggatgtctt ctaacatcgg tggtggtggt      240
```

```
actgacactt tgaaggaatg tccattgaag cacagagctt ggaactcttt cttggttgaa    300
gaccacggtt tcggtgtttt ccacacttct gtttggttga aggttagaga agactactct    360
ttggaaggtg gtggtggtac tatcatcgtt aaccacgtta acgacacttg gggtttgaag    420
gttagacaat ctttgtggtt ccacttgtct gtttgactt tcggtcaaca cactgttcaa     480
gaattcttgg tttctttcgg tgtttggatc agaactccag ctccatacag accaccaaac   540
gctccaatct tgtctacttt gccagaacac actgttatca agaagaagag tggtgctaga    600
gcttctagat ctccaagaag aagaactcca tctccaagaa gaagaagatc tcaatctcca    660
agaagaagaa gatctcaatc tccatctgct aactgt                              696
```

<210> SEQ ID NO 93
<211> LENGTH: 708
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 81

<400> SEQUENCE: 93

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt   180
tgttgggacg aattgactaa gttgatcgct tggatgtctt ctaacatcgg tggtggtggt    240
acttgtgacc cagctgttat cggtactgct gttaagggta aggaagctgt tcactctgac    300
ttgggttact ggatcgaatc tgaaaagaac gacacttgga gattgaagag agctcacttg    360
atcgaaatga gacttgtgg tggtggtggt actatcatcg ttaaccacgt taacgacact    420
tggggtttga aggttagaca atctttgtgg ttccacttgt cttgtttgac tttcggtcaa    480
cacactgttc aagaattctt ggtttctttc ggtgtttgga tcagaactcc agctccatac   540
agaccaccaa acgctccaat cttgtctact ttgccagaac acactgttat cagaagaaga    600
ggtggtgcta gagcttctag atctccaaga agaagaactc catctccaag aagaagaaga    660
tctcaatctc caagaagaag aagatctcaa tctccatctg ctaactgt                 708
```

<210> SEQ ID NO 94
<211> LENGTH: 633
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 82

<400> SEQUENCE: 94

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actggttact ggatcgaatc tgaaaagaac gacacttgga gattgaagag agctcacttg    300
atcggtggtg gtggtactat catcgttaac cacgttaacg acacttgggg tttgaaggtt    360
agacaatctt tgtggttcca cttgtcttgt ttgactttcg gtcaacacac tgttcaagaa    420
```

```
ttcttggttt ctttcggtgt ttggatcaga actccagctc catacagacc accaaacgct    480
ccaatcttgt ctactttgcc agaacacact gttatcagaa gaagaggtgg tgctagagct    540
tctagatctc caagaagaag aactccatct ccaagaagaa gaagatctca atctccaaga    600
agaagaagat ctcaatctcc atctgctaac tgt                                 633
```

<210> SEQ ID NO 95
<211> LENGTH: 762
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 83

<400> SEQUENCE: 95

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actagagctc acttgatcga aatgaagact tgtgaatggc aaagtctca cactttgtgg    300 actgacggta tcgaagaatc tgacttgatc atcccaaagt ctttggctgg tccattgtct    360
caccacaaca ctagagaagg ttacagaact caaatgaagg tccatggca ctctgaagaa    420 ttggaaatca gaggtggtgg tggtactatc atcgttaacc acgttaacga cactgggggt    480
ttgaaggtta gacaatcttt gtggttccac ttgtcttgtt tgactttcgg tcaacacact    540
gttcaagaat tcttggtttc tttcggtgtt tggatcagaa ctccagctcc atacagacca    600
ccaaacgctc caatcttgtc tactttgcca gaacacactg ttatcagaag agaggtggt    660 gctagagctt ctagatctcc aagaagaaga actccatctc aagaagaag aagatctcaa    720 tctccaagaa gaagaagatc tcaatctcca tctgctaact gt                       762
```

<210> SEQ ID NO 96
<211> LENGTH: 735
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 84

<400> SEQUENCE: 96

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actttggaaa tcagattcga agaatgtcca ggtactaagg ttcacgttga agaaacttgt    300
ggtactagag gtccatcttt gagatctact actgcttctg gtagagttat cgaagaatgg    360
tgttgtagag aatgtactat gccaccattg tctttcagag ctaagggtgg tggtggtact    420
atcatcgtta accacgttaa cgacacttgg ggtttgaagg ttagacaatc tttgtggttc    480
cacttgtctt gtttgacttt cggtcaacac actgttcaag aattcttggt ttctttcggt    540
```

```
gtttggatca gaactccagc tccatacaga ccaccaaacg ctccaatctt gtctactttg    600
ccagaacaca ctgttatcag aagaagaggt ggtgctagag cttctagatc tccaagaaga    660
agaactccat ctccaagaag aagaagatct caatctccaa gaagaagaag atctcaatct    720
ccatctgcta actgt                                                     735

<210> SEQ ID NO 97
<211> LENGTH: 723
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 85

<400> SEQUENCE: 97
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
acttgtccag gtactaaggt tcacgttgaa gaaacttgtg gtactagagg tccatctttg    300
agatctacta ctgcttctgg tagagttatc gaagaatggt gttgtagaga atgtactatg    360
ccaccattgt ctttcagagc taaggacggt tgtggtggtg gtggtactat catcgttaac    420
cacgttaacg acacttgggg tttgaaggtt agacaatctt gtggttcca cttgtcttgt    480 ttgactttcg gtcaacacac tgttcaagaa ttcttggttt ctttcggtgt ttggatcaga    540
actccagctc catacagacc accaaacgct ccaatcttgt ctactttgcc agaacacact    600
gttatcagaa gaagaggtgg tgctagagct tctagatctc aagaagaag aactccatct    660 ccaagaagaa gaagatctca atctccaaga agaagaagat ctcaatctcc atctgctaac    720
tgt                                                                  723

<210> SEQ ID NO 98
<211> LENGTH: 840
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 54) PLUS SEQ ID NO: 86

<400> SEQUENCE: 98
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actatgaagg gtccatggca ctctgaagaa ttggaaatca gattcgaaga atgtccaggt    300
actaaggttc acgttgaaga aacttgtggt actagaggtc catctttgag atctactact    360
gcttctggta gagttatcga agaatggtgt tgtagagaat gtactatgcc accattgtct    420
ttcagagcta aggacggttg ttggtacggt atggaaatca gaccaagaaa ggaaccagaa    480
tctaacttgg ttagatctat ggttactgct ggtggtggtg gtactatcat cgttaaccac    540
gttaacgaca cttggggttt gaaggttaga caatctttgt ggttccactt gtcttgtttg    600
```

```
actttcggtc aacacactgt tcaagaattc ttggtttctt tcggtgtttg gatcagaact    660
ccagctccat acagaccacc aaacgctcca atcttgtcta ctttgccaga acacactgtt    720
atcagaagaa gaggtggtgc tagagcttct agatctccaa gaagaagaac tccatctcca    780
agaagaagaa gatctcaatc tccaagaaga agaagatctc aatctccatc tgctaactgt    840
```

<210> SEQ ID NO 99
<211> LENGTH: 504
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: prM Furin Deficient

<400> SEQUENCE: 99

```
gctgaagtta ctagaagagg ttctgcttac tacatgtact tggacagaaa cgacgctggt     60
gaagctatct ctttcccaac tactttgggt atgaacaagt gttacatcca atcatggac    120 ttgggtcaca tgtgtgacgc tactatgtct tacgaatgtc caatgttgga cgaaggtgtt    180
gaaccagacg acgttgactg ttggtgtaac actacttcta cttgggttgt ttacggtact    240
tgtcaccaca agaagggtga agctggtggt tctggtggtg ctgttacttt gccatctcac    300
tctactagaa agttgcaaac tagatctcaa acttggttgg aatctagaga atacactaag    360
cacttgatca gagttgaaaa ctggatcttc agaaacccag ttcgctttt ggctgctgct    420 gctatcgctt ggttgttggg ttcttctact tctcaaaagg ttatctactt ggttatgatc    480
ttgttgatcg ctccagctta ctct                                           504
```

<210> SEQ ID NO 100
<211> LENGTH: 225
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: M full length

<400> SEQUENCE: 100

```
gctgttactt tgccatctca ctctactaga aagttgcaaa ctagatctca aacttggttg     60
gaatctagag aatacactaa gcacttgatc agagttgaaa actggatctt cagaaaccca    120 gtttcgctt tggctgctgc tgctatcgct tggttgttgg gttcttctac ttctcaaaag    180
gttatctact tggttatgat cttgttgatc gctccagctt actct                    225
```

<210> SEQ ID NO 101
<211> LENGTH: 1077
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 62) PLUS SEQ ID NO:99

<400> SEQUENCE: 101

```
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
```

```
tgttgggacg aattgactaa gttgatcgct tggatgtctt ctaacatcgg tggtggtggt      240
actgctgaag ttactagaag aggttctgct tactacatgt acttggacag aaacgacgct      300
ggtgaagcta tctctttccc aactactttg ggtatgaaca agtgttacat ccaaatcatg      360
gacttgggtc acatgtgtga cgctactatg tcttacgaat gtccaatgtt ggacgaaggt      420
gttgaaccag acgacgttga ctgttggtgt aacactactt ctacttgggt tgtttacggt      480
acttgtcacc acaagaaggg tgaagctggt ggttctggtg gtgctgttac tttgccatct      540
cactctacta gaaagttgca aactagatct caaacttggt tggaatctag agaatacact      600
aagcacttga tcagagttga aaactggatc ttcagaaacc caggtttcgc tttggctgct      660
gctgctatcg cttggttgtt gggttcttct acttctcaaa aggttatcta cttggttatg      720
atcttgttga tcgctccagc ttactctggt ggtggtggta ctatcatcgt taaccacgtt      780
aacgacactt ggggtttgaa ggttagacaa tctttgtggt tccacttgtc ttgtttgact      840
ttcggtcaac acactgttca agaattcttg gtttctttcg tgtttggat cagaactcca      900 gctccataca gaccaccaaa cgctccaatc ttgtctactt tgccagaaca cactgttatc      960
agaagaagag gtggtgctag agcttctaga tctccaagaa gaagaactcc atctccaaga     1020
agaagaagat ctcaatctcc aagaagaaga agatctcaat ctccatctgc taactgt       1077

<210> SEQ ID NO 102
<211> LENGTH: 798
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 62) PLUS SEQ ID NO: 100

<400> SEQUENCE: 102
atggacatcg acccatacaa ggaattcggt tcttcttacc aattgttgaa cttcttgcca       60
ttggacttct tcccagactt gaacgctttg gttgacactg ctactgcttt gtacgaagaa      120
gaattgactg gtagagaaca ctgttctcca caccacactg ctatcagaca gcttttggtt      180
tgttgggacg aattgactaa gttgatcgct tggatgtctt ctaacatcgg tggtggtggt      240
actgctgtta ctttgccatc tcactctact agaaagttgc aaactagatc tcaaacttgg      300
ttggaatcta gagaatacac taagcacttg atcagagttg aaaactggat cttcagaaac      360
ccaggtttcg ctttggctgc tgctgctatc gcttggttgt tgggttcttc tacttctcaa      420
aaggttatct acttggttat gatcttgttg atcgctccag cttactctgg tggtggtggt      480
actatcatcg ttaaccacgt taacgacact tggggtttga aggttagaca atctttgtgg      540
ttccacttgt cttgtttgac tttcggtcaa cacactgttc aagaattctt ggtttctttc      600
ggtgtttgga tcagaactcc agctccatac agaccaccaa acgctccaat cttgtctact      660
ttgccagaac acactgttat cagaagaaga ggtggtgcta gagcttctag atctccaaga      720
agaagaactc catctccaag aagaagaaga tctcaatctc caagaagaag aagatctcaa      780
tctccatctg ctaactgt                                                    798

<210> SEQ ID NO 103
<211> LENGTH: 312
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: MISC_FEATURE
<223> OTHER INFORMATION: C full length

<400> SEQUENCE: 103
atgaagaacc caaagaagaa gtctggtggt tcagaatcg ttaacatgtt gaagagaggt      60
gttgctagag tttctccatt cggtggtttg aagagattgc cagctggttt gttgttgggt    120
cacggtccaa tcagaatggt tttggctatc ttggctttct tgagattcac tgctatcaag    180
ccatctttgg gtttgatcaa cagatggggt tctgttggta agaaggaagc tatggaaact    240
atcaagaagt tcaagaagga cttggctgct atgttgagaa tcatcaacgc tagaaaggaa    300
aagaagagaa ga                                                        312

<210> SEQ ID NO 104
<211> LENGTH: 75
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: C alpha 2

<400> SEQUENCE: 104
ggtcacggtc caatcagaat ggttttggct atcttggctt tcttgagatt cactgctatc     60
aagccatctt tgggt                                                      75

<210> SEQ ID NO 105
<211> LENGTH: 885
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 62) PLUS SEQ ID NO:103

<400> SEQUENCE: 105
atggacatcg acccatacaa ggaattcggt tcttcttacc aattgttgaa cttcttgcca     60
ttggacttct tcccagactt gaacgctttg gttgacactg ctactgcttt gtacgaagaa    120
gaattgactg gtagagaaca ctgttctcca caccacactg ctatcagaca agctttggtt    180
tgttgggacg aattgactaa gttgatcgct tggatgtctt ctaacatcgg tggtggtggt    240
actatgaaga acccaaagaa gaagtctggt ggtttcagaa tcgttaacat gttgaagaga    300
ggtgttgcta gagtttctcc attcggtggt ttgaagagat gccagctgg tttgttgttg    360 ggtcacggtc caatcagaat ggttttggct atcttggctt tcttgagatt cactgctatc    420
aagccatctt tgggtttgat caacagatgg ggttctgttg gtaagaagga agctatggaa    480
actatcaaga gttcaagaa ggacttggct gctatgttga gaatcatcaa cgctagaaag    540
gaaaagaaga gaagaggtgg tggtggtact atcatcgtta accacgttaa cgacacttgg    600
ggtttgaagg ttagacaatc tttgtggttc cacttgtctt gtttgacttt cggtcaacac    660
actgttcaag aattcttggt ttctttcggt gtttggatca gaactccagc tccatacaga    720
ccaccaaacg ctccaatctt gtctactttg ccagaacaca ctgttatcag aagaagaggt    780
ggtgctagag cttctagatc tccaagaaga agaactccat ctccaagaag aagaagatct    840
caatctccaa gaagaagaag atctcaatct ccatctgcta actgt                    885
```

```
<210> SEQ ID NO 106
<211> LENGTH: 648
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: MISC_FEATURE
<223> OTHER INFORMATION: WHcAg (SEQ ID NO: 62) PLUS SEQ ID NO:104

<400> SEQUENCE: 106
atggacatcg acccatacaa ggaattcggt tcttcttacc aattgttgaa cttcttgcca      60
ttggacttct tcccagactt gaacgctttg gttgacactg ctactgcttt gtacgaagaa     120
gaattgactg gtagagaaca ctgttctcca caccacactg ctatcagaca agctttggtt     180
tgttgggacg aattgactaa gttgatcgct tggatgtctt ctaacatcgg tggtggtggt     240
actggtcacg gtccaatcag aatggttttg gctatcttgg ctttcttgag attcactgct     300
atcaagccat ctttgggtgg tggtggtggt actatcatcg ttaaccacgt taacgacact     360
tggggtttga aggttagaca atctttgtgg ttccacttgt cttgtttgac tttcggtcaa     420
cacactgttc aagaattctt ggtttctttc ggtgtttgga tcagaactcc agctccatac     480
agaccaccaa acgctccaat cttgtctact ttgccagaac acactgttat cagaagaaga     540
ggtggtgcta gagcttctag atctccaaga agaagaactc catctccaag aagaagaaga     600
tctcaatctc aagaagaag aagatctcaa tctccatctg ctaactgt                   648
```